(12) United States Patent
Grinstaff et al.

(10) Patent No.: US 10,866,230 B2
(45) Date of Patent: Dec. 15, 2020

(54) FIBER COATED NANOPORES

(71) Applicant: Trustees of Boston University, Boston, MA (US)

(72) Inventors: Mark Grinstaff, Brookline, MA (US); Amit Meller, Brookline, MA (US); Joseph Hersey, Cambridge, MA (US); Allison Squires, Allston, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 726 days.

(21) Appl. No.: 14/895,714

(22) PCT Filed: May 30, 2014

(86) PCT No.: PCT/US2014/040333
§ 371 (c)(1),
(2) Date: Dec. 3, 2015

(87) PCT Pub. No.: WO2014/197329
PCT Pub. Date: Dec. 11, 2014

(65) Prior Publication Data
US 2016/0169864 A1    Jun. 16, 2016

Related U.S. Application Data

(60) Provisional application No. 61/830,334, filed on Jun. 3, 2013.

(51) Int. Cl.
*C12Q 1/6825* (2018.01)
*G01N 33/487* (2006.01)
(Continued)

(52) U.S. Cl.
CPC ....... *G01N 33/48721* (2013.01); *B05D 1/007* (2013.01); *C08J 7/0427* (2020.01);
(Continued)

(58) Field of Classification Search
None
See application file for complete search history.

(56) References Cited

U.S. PATENT DOCUMENTS 9,121,843 B2 * 9/2015 Meller ................ B82Y 15/00
9,903,820 B2 * 2/2018 Meller ................ B82Y 15/00
(Continued)

FOREIGN PATENT DOCUMENTS

WO    2005/017025 A2    2/2005
WO    2005/061373 A1    7/2005
(Continued)

OTHER PUBLICATIONS

The defintion of "cover" as evidenced by the online dictionary at Merian-Webster.com [retrieved on Apr. 8, 2020]. Retrieved from the Internet: <URL: www.merriam-webster.com/dictionary/cover>.*

*Primary Examiner* — Robert T. Crow
(74) *Attorney, Agent, or Firm* — Nixon Peabody LLP; Ronald I. Eisenstein; Ravinderjit Braich

(57) ABSTRACT

Provided herein are compositions, compounds, processes, and methods of use of 3D porous coating(s) on or near a nanopore(s) for analysis or detection of charged polymers such as nucleic acids, proteins, protein-nucleic acid complexes, small molecule-biological complexes, polymer-biological complexes, and/or polyelectrolytes.

7 Claims, 26 Drawing Sheets

(51) Int. Cl.
*C08J 7/04* (2020.01)
*B05D 1/00* (2006.01)
*G01N 27/447* (2006.01)

(52) U.S. Cl.
CPC ..... *C12Q 1/6825* (2013.01); *G01N 27/44747* (2013.01); *G01N 27/44791* (2013.01); *C08J 2309/02* (2013.01); *C08J 2477/02* (2013.01)

(56) References Cited

U.S. PATENT DOCUMENTS

| | | | | |
|---|---|---|---|---|
| 2002/0182627 | A1* | 12/2002 | Wang | B01L 3/502761 435/6.11 |
| 2004/0241436 | A1* | 12/2004 | Hsieh | D01D 5/0007 428/361 |
| 2008/0195211 | A1* | 8/2008 | Lin | A61F 2/30942 623/17.16 |
| 2008/0206101 | A1* | 8/2008 | Huang | B01L 3/5027 422/68.1 |
| 2011/0053284 | A1 | 3/2011 | Meller et al. | |
| 2011/0172785 | A1* | 7/2011 | Wolinsky | A61K 9/0024 623/23.72 |
| 2011/0207168 | A1* | 8/2011 | Kornev | D06M 10/025 435/34 |
| 2011/0294159 | A1* | 12/2011 | Potember | C12N 11/06 435/41 |
| 2012/0135225 | A1* | 5/2012 | Colas | A61K 9/7084 428/332 |

FOREIGN PATENT DOCUMENTS

| | | |
|---|---|---|
| WO | 2006/137891 A2 | 12/2006 |
| WO | 2011/130312 A1 | 10/2011 |
| WO | WO 2013/013038 A2 * 1/2013 | ............ A61K 47/48 |

* cited by examiner

PARALLEL FABRICATION ~1 MIN ELECTROSPINNING

CURRENT VERSUS VOLTAGE CURVES MEASURED FOR AN UNCOATED NANOPORE (BLUE) AND TWO NP-NFM DEVICES (PCL ONLY, GREEN; 70:30 PCL:PGC, RED). THE IDENTICAL CONDUCTANCE FOR ALL CONDITIONS INDICATES THAT THE NFM COATING DOES NOT ALTER THE ELECTRICAL PROPERTIES OF THE NANOPORE.

FIBER COATED NANOPORES

CROSS-REFERENCE TO RELATED APPLICATIONS

This application is a 35 U.S.C. § 371 National Phase Entry Application of International Application No. PCT/US14/40333 filed May 30, 2014, which claims benefit under 35 U.S.C. § 119(e) of U.S. Provisional Application No. 61/830,334, filed Jun. 3, 2013, the contents of which are incorporated herein by reference in their entireties.

GOVERNMENT SUPPORT

This invention was made with government support under Grant Nos. HG005871 and CA 149561 awarded by the National Institutes of Health. The Government has certain rights in the invention.

TECHNICAL FIELD

Provided herein are compositions, compounds, processes, and methods of use of 3D porous coating(s) on or near a nanopore(s) for analysis or detection of biologics such as nucleic acids, proteins, protein-nucleic acid complexes, small molecule-biological complexes, and/or polymer-biological complexes.

BACKGROUND

In 1994, Berzrukov, Vodyanoy, and Parsegian showed that a biological nanopore can be used as a Coulter counter to count individual molecules. In 1996, in a landmark paper by Kasianowicz, Brandin, Branton, and Deamer (KBBD), [Kasianowicz, L J, Brandin, E, Branton, D. & Deamer, D. W. Characterization of individual polynucleotide molecules using a membrane channel, Proc. Nat. Acad. Sci. USA 93, 13770-13773 (1996)] was proposed for ultrafast single-molecule sequencing of single-stranded (ss) DNA molecules using nanopore ionic conductance as a sensing mechanism. Since then several groups have explored the α-hemolysin protein pore as a possible candidate for achieving this objective.

SUMMARY

The invention is based, at least in part, on the discovery that: 1) membranes or thin solid-state, polymeric, lipid, or solid-like films containing nanopores can be coated with fibers, gels, or other compositions to create a 3D porous structure above or below the membrane or both; 2) one or many nanopores in a given membrane can be coated to create a multiplexed system; 3) the coated nanopore alters the rate at which a biologic transits or translocates through the nanopore compared to a bare membrane; 4) the coating can be modified or derivatized to change its hydrophilicity/hydrophobicity; 5) the coating can be modified or derivatized to introduce one or more targeting moiety that captures or binds an analyte for subsequent translocation through the nanopore; and 6) the act of translocating through the nanopore enables identification of the biologic as a change in electrical conductivity, fluid flow, refractive index, as measured by either electrical or optical means or both. One aspect of this invention is the use of the coated nanopores for detecting a specific nucleic acid sequence (e.g., DNA, RNA, mRNA, miRNA, etc) or protein (e.g., hemoglobin, insulin, antibody, etc). A further aspect of this invention is the use of the coated nanopores for sequencing nucleic acids or proteins. An additional aspect of this invention is the use of the coated nanopores to size nucleic acids or proteins for genomic, transcriptomic, or proteomic analysis. Another aspect of the coating is the use of stimuli responsive materials (heat, light, pH, redox, enzymatic, magnetic, etc.) to affect the properties of the coating. Provided herein are compositions, compounds, processes, and methods of use of 3D porous coated nanopores for analysis or detection of biologics. The 3D coating provides a high surface area for interaction with the biologic.

BRIEF DESCRIPTION OF THE DRAWINGS

FIG. 1A is a schematic diagram of the experiment illustrating biotinylated fluorescein binding the avidin coated mesh. FIG. 1B shows a confocal microscopy image of a mesh coated in $^{1}/_{10,000}$ vs. $^{1}/_{100}$ equivalents avidin to carboxylic acid on the mesh surface. FIG. 1C is the fluorescence intensity increase with increasing amounts of avidin bound to the mesh surface. An adsorption control is shown (red square) which highlights the need for EDC coupling to covalently link the avidin to the fiber surface. FIG. 1D is a biotin-fluorescein titration curve to quantify the avidin loading on the $^{1}/_{250}$ equivalent mesh surface. The fluorescent signal begins to drop when there is no longer enough biotin-fluorescein to bind all of the biotin binding sites.

FIG. 9A A 4 ul droplet is placed on the mesh and measured according to the angle formed at the interface of the droplet with the surface. FIG. 9B Contact angle as a function of mesh composition. Please note that FIG. 9B presents the same data as shown in FIG. 4A (now presented as FIG. 24A) of the priority provisional application.

FIG. 14A depicts sample translocation events for the same nanopore, bare (blue) and coated (red, 7:3 PCL:PGC-C18). Scale bar at right, Iopen=2.7 nA. 1000 bp DNA, 300 mV, 250 kHz, sample events low-pass filtered at 10 kHz. FIG. 14B depicts event diagrams for the corresponding full data sets and histograms of translocation time for same bare and coated pore with exponential decay to characterize translocation time. Coated nanopore requires a double exponential decay fit to accurately capture the distribution.

FIG. 17A depicts an event diagram for five lengths of dsDNA (0.5, 1, 5, 10, and 20 kbp) translocating through a 6 nm nanopore coated with 7:3 PCL:PGC-C18. Ib is normalized for clarity. FIG. 17B depicts a characteristic translocation time τ for each DNA length (error bar: τ±95% fit confidence interval). Dotted line is a guide to the eye.

FIG. 18A depicts an event diagram for translocation of 1 kbp, 5 kbp, and 10 kbp DNA in a bare 6 nm diameter nanopore at 500 mV. FIG. 18B depicts a relative τ for 1, 5, and 10 kbp in the 7:3 PCL:PGC-C18 coated nanopore, normalized by this bare pore data. Although a slight increase in this retardation factor is observed with increasing length, there is little or no increase within the fit error (error bars for 1 kbp are smaller than marker).

DETAILED DESCRIPTION

Figure 1A:
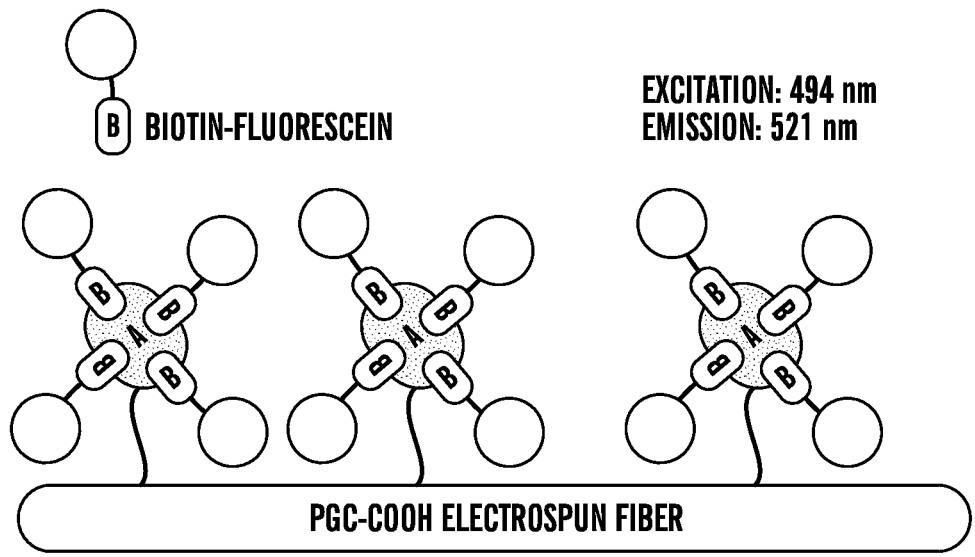
FIGS. 1A-1D demonstrates that the avidin functionalized electrospun mesh can be characterized with biotinylated fluorescein.
Figure 1B:
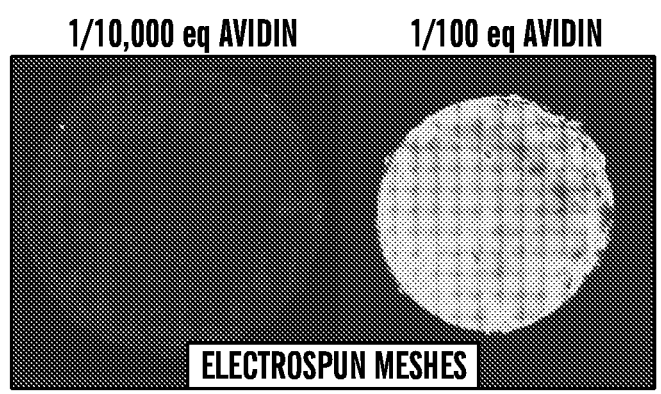
Figure 1D:
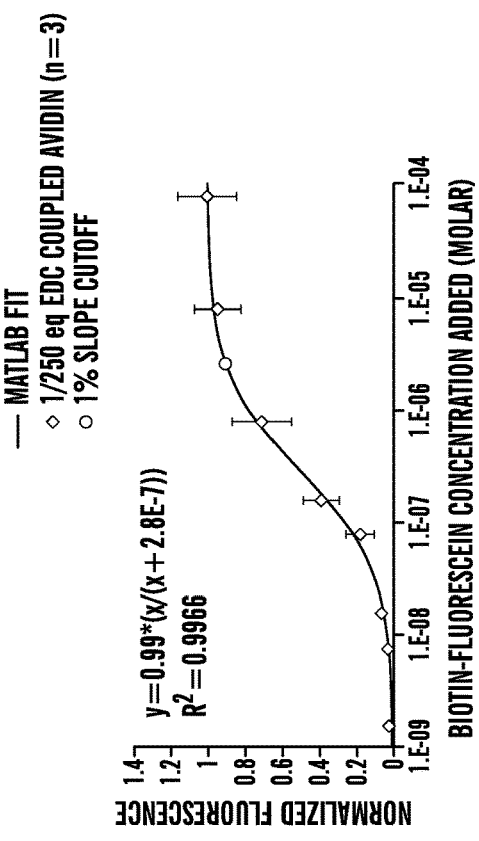
Figure 1C:
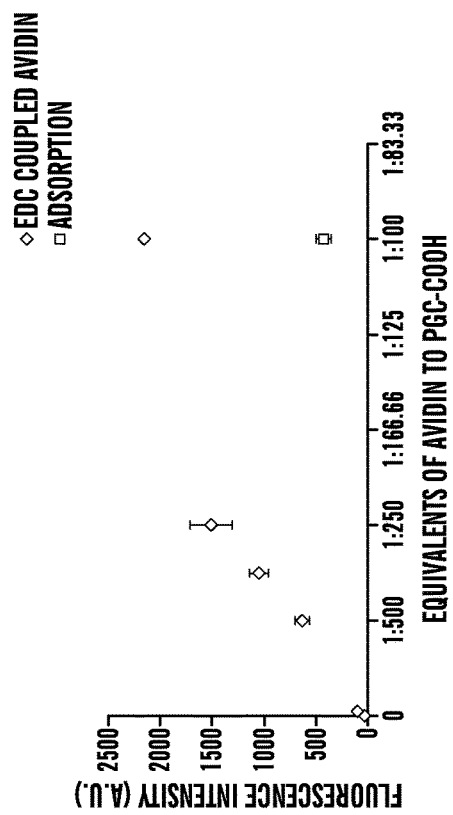
Figure 2:
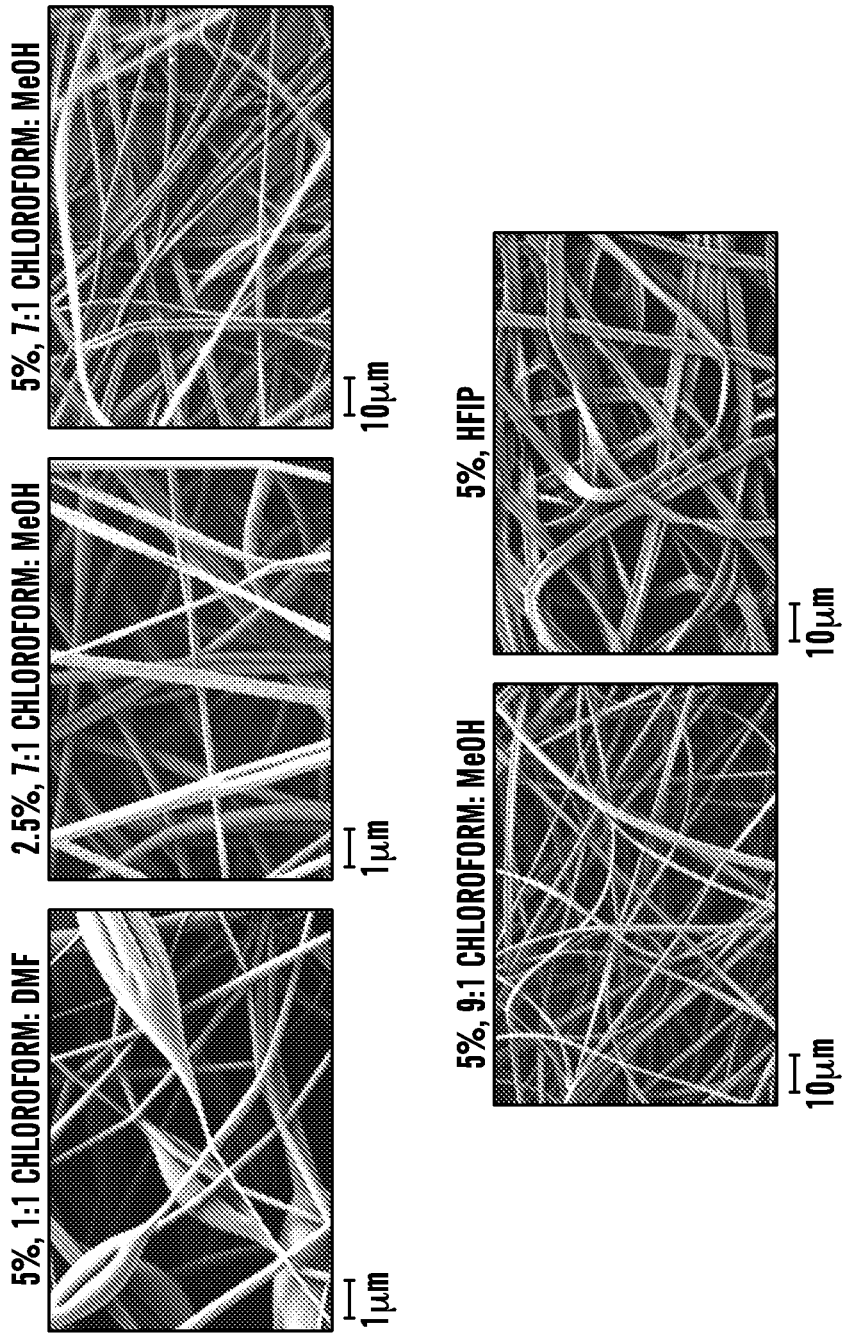
FIG. 2 depicts scanning electron microscopy of poly (oxanorbornene-dicarboxamine-butyl) electrospun meshes fabricated using different solvent systems.
Figure 3:
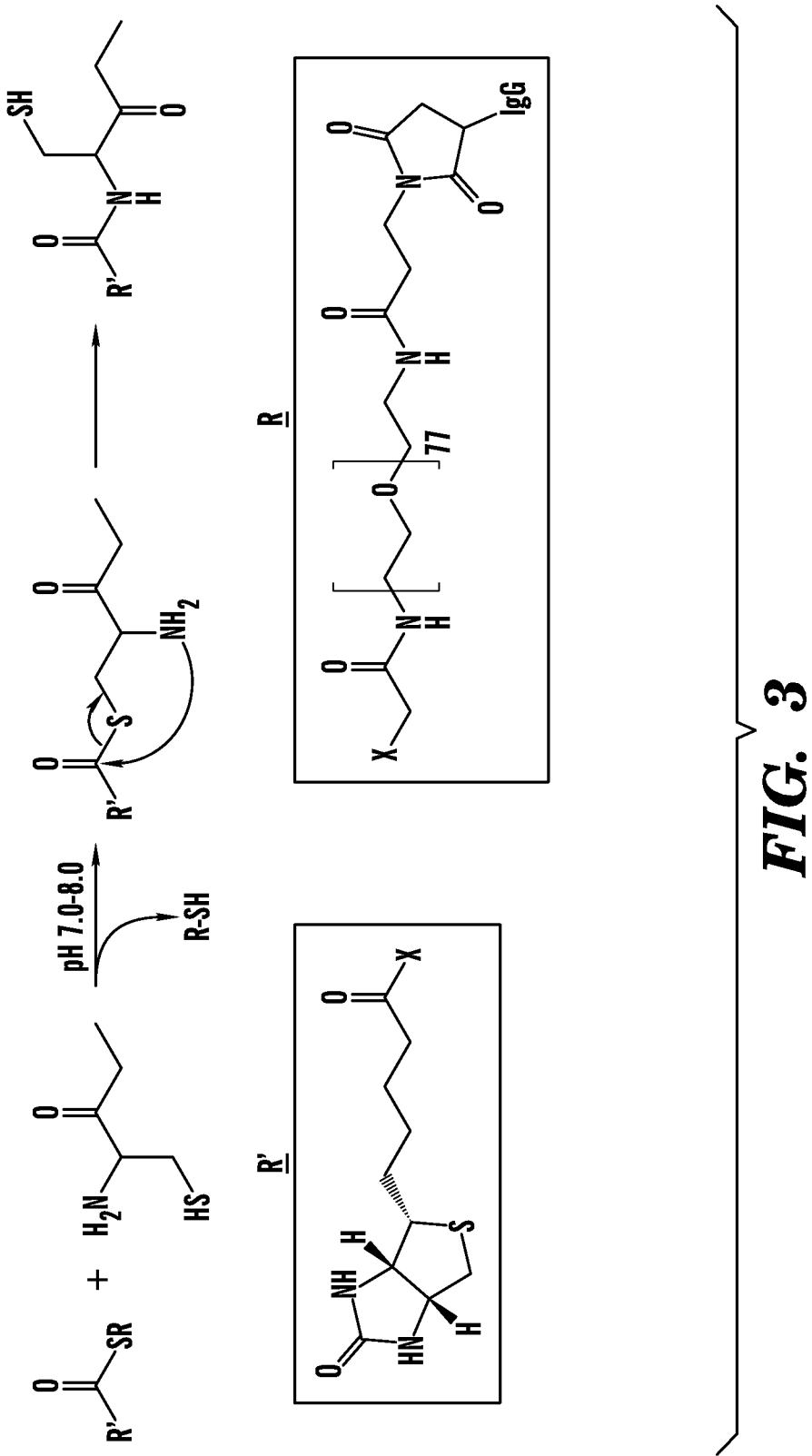
FIG. 3 depicts the native chemical ligation chemistry utilized as a stimulus for the stimuli responsive separation of biotin and antibody (IgG).

In one aspect, the disclosure provides an article comprising: (i) a substrate having a first surface and as second surface; (ii) at least one nanopore extending through the substrate, thus forming a channel connecting from the first surface to the second surface of the substrate, wherein the nanopore has a first opening that opens to the first surface of the substrate and a second opening that opens to the second surface of the substrate; and (iii) a porous coating on at least one of the first or second surface of the substrate. The substrate can be configured to include more than one nanopore, or an array of nanopores. Each individual nanopore can be enclosed in an individual chamber and such individual chambers can be arranged in an array format. Without wishing to be bound by a theory, the porous coating can alter the rate at which a molecule transits or translocates through the nanopore compared to when no porous coating is present.

In some embodiments of the various aspects disclosed herein, the substrate is a membrane or thin solid-state, polymeric, lipid, or solid-like film.

Nanopores have been drilled in a range of membrane materials, including but, not limited to, polymers, glass, silicon dioxide, and graphene. Thus, without limitations, the substrate can comprise any suitable material. Further, the substrate can be of a pure substance, a mixture or a composite. For example, the substrate can comprise a semiconductor material, polymer material, lipid, quartz, glass, and the like. In some embodiments, the substrate can be made of, for example, glass, Si, $SiO_2$, $SiN_4$, quartz, alumina, nitrindes, metals, polymers, or any combinations thereof. In some embodiments, the substrate comprises an insulating material. Exemplary insulating materials include, but are not limited to, SiN, $SiO_2$, $Al_2O_3$, $TiO_2$, $BaTiO_3$, $PbTiO_3$, and the like. In some embodiments, the substrate can comprise a semiconductor material, such as, but not limited to, silicon (Si), SiN, germanium (Ge), GaAs, GaN, and the like. A preferred material is SiN.

The substrate can be of any desired thickness. In some embodiments of the various aspects disclosed herein, thickness of the substrate can range from about 5 nm to about 1000 nm.

In some embodiments, the substrate is electrically insulating, i.e., is an electrical insulator.

Generally, the substrate comprises an opening defining a nanopore of a suitable size. The substrate comprises a first surface and a second surface. The first and the second surfaces can be arranged substantially parallel to one another. The nanopore forms a passage through the substrate from the first surface to the second surface. Thus, the nanopore has a first opening on the first surface of the substrate and a second opening on the second surface of the substrate. The openings defining the nanopore can be of any suitable shape, but are typically approximately circular.

The substrate is referred to herein as having a "first" and "second" surface. Such references are merely for the purposes of explaining and illustrating the invention and various embodiments thereof. These references are not intended to imply any particular orientation in use, and are not intended to limit the invention in any other manner.

The substrate comprising the one or more nanopores can divide a volume into two separate compartments, each of which can contain different types and/or concentrations of analytes. One or more nanopore(s) is the only passage between these two compartments. When electrodes are placed in each compartment and a voltage is applied, an electric field develops across the nanopore. The applied electric field acts as a force on charged molecules and ions inside the nanopore. Inventors have discovered inter alia that nanopore in a substrate coated with a porous coating have the same conductivity as a those in lacking that porous coating but translocation dynamics are dependent upon the properties of the applied porous coating. The inventors have discovered that characteristic translocation time for porous coating depends upon hydrophobicity of the coating. By optimizing the hydrophobicity of the coating, inventors demonstrated a retardation factor for the porous coating as compared to translocation through a bare nanopore from ~2 to more than two orders of magnitude.

As used herein, the term "nanopore" refers to a nanometer sized opening in the substrate, i.e., pores have a pore size in the nanometer range. The nanopore extends through the substrate and forms a channel connecting the first surface to the second surface, wherein the nanopore has a first opening that opens to the first surface of the substrate and a second opening that opens to the second surface of the membrane As used herein, the term "pore size" refers to a diameter or an effective diameter of the cross-sections of the pores. The term "pore size" can also refer to an average diameter or an average effective diameter of the cross-sections of the pores, based on the measurements of a plurality of pores. The effective diameter of a cross-section that is not circular equals the diameter of a circular cross-section that has the same cross-sectional area as that of the non-circular cross-section. As used herein a "nanopore" includes a nanometer opening in solid state, polymeric, lipid, or alpha-hemolysin structure containing pores of 2 to 10000 nm in diameter.

It will be understood by one of ordinary skill in the art that pores can exhibit a distribution of sizes around the indicated "size." Unless otherwise stated, the term "size" as used herein refers to the mode of a size distribution of pores, i.e., the value that occurs most frequently in the size distribution. The pore size distribution of the nanopores can range from about 2 nm to about 10,000 nm. In some embodiments of the various aspects disclosed herein, the nanopore diameter can range from about 5 nm to about 1000 nm, from 5 nm to about 500 nm. In some embodiments, the nanopore diameter can range from about 2 nm to about 50 nm. In one embodiment, the nanopore diameter can range from about 5 nm to about 20 nm. In one particular embodiment, the nanopore diameter is about 5 nm. A preferred nanopore size is between 4 and 10 nm.

As the nanopores are nanometers to micrometers in width, it is possible that many thousands of them can be created on a single substrate such as a silicon micro-chip semiconductor wafer. Accordingly, a single substrate can hold hundreds or thousands of nanopores to simultaneously detect many different biological and/or chemical materials.

It is not intended that the term "nanopore" be limited to circular geometries, as openings having multi-sided geometries are also suitable for providing a nanopore. Thus, nanopores, as used herein, are not limited to cylindrical surface geometries and/or circular cross-sections. A nanopore in the various embodiments of the various aspects disclosed herein can have a cylindrical or non-cylindrical surface geometry and/or a circular or non-circular cross-section. In some embodiments, the nanopore has a cylindrical surface geometry or cross-section.

The nanopore can, optionally, taper from the first surface of the substrate to the second surface of the substrate. In other words, the nanopore can have a diameter at the first surface of the substrate that is smaller or larger than the diameter of the nanopore at the second surface of the substrate. In some embodiments, the nanopore has a diameter at the first surface of the substrate that is substantially similar to the diameter at the second surface of the substrate.

While the porous coating is discussed as being a single layer, it is to be understood that the porous coating layer can comprise more than one (e.g., one, two, three, four, five, six, seven, eight, nine, ten or more layers). Further, description of porous coating as disclosed herein can apply to each of the individual layers of the coating. Moreover, when two or more layers are present in the porous coating, all the layers can be same, all different, or some same and some different. The differences can be based on the components of the layers, thickness of the layers, porosity of the layers, chemical properties, e.g., hydrophobicity or hydrophilicity of the layers, and the like.

The porous coating can comprise any suitable material through which a molecule of interest, for example, a target molecule or analyte molecule, can pass, but which will reduce the translocation speed of the molecule passing through the nanopore as compared to the translocation speed of the molecule through the nanopore in the absence of the porous coating. Without limitations, the porous coating material can be hydrophilic, hydrophobic, anionic, cationic, or any combinations thereof.

The porous coating can be in the form of gels, hydrogels, fibers, nanofibers, nanoparticles, meshes, mats, 3D-scaffolds, and the like. In some embodiments, the porous coating is a non-woven mesh or mat. In some embodiments, the porous coating comprises electrospun fibers. As used herein, the term "hydrogel" refers to a three-dimensional polymeric structure that is insoluble in water but which is capable of absorbing and retaining large quantities of water to form a stable, often soft and pliable, structure. In some embodiments, water can penetrate in between the polymer chains of the polymer network, subsequently causing swelling and the formation of a hydrogel.

In some embodiments, the coating layer comprises two (e.g., two, three, four, five, six, seven, eight, nine, ten or more) different materials. Without wishing to be bound by a theory, ratio of the different materials can be varied to optimize one or more desired properties of the porous coating. Ratio between any two different materials can range from 99:1 to 1:99.

In some embodiments of the various aspects disclosed herein, the porous coating layer comprises an oligomeric or polymeric material. For example, the porous coating layer can be composed of a linear, comb, branched, or dendritic oligomer or polymer.

In some embodiments, the porous coating material comprises a reactive functional group. As used herein, the term "reactive functional group" refers to a functional group that allows covalent linkage of a molecule of interest to the porous coating, for example, linking of a targeting moiety to the porous coating layer. Targeting moieties are described in more detail elsewhere in the disclosure. Exemplary reactive functional groups include, but are not limited to, hydroxyls or alcohols, amines, azides, alkynes, alkenes, NHS, MAL, thiols, thials, sulfinos, acids, carboxylic acids, and the like.

In some embodiments, the porous coating comprises an oligomer or polymer represented by one of the following formulas:

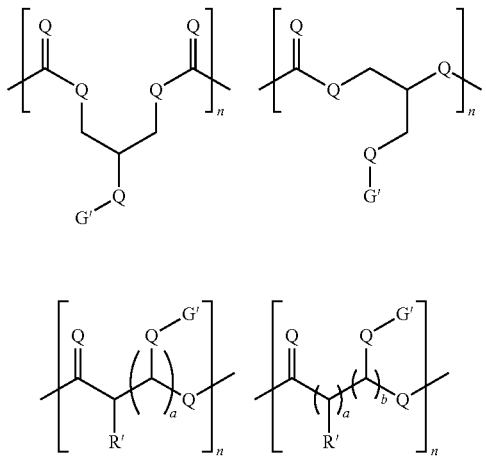

-continued

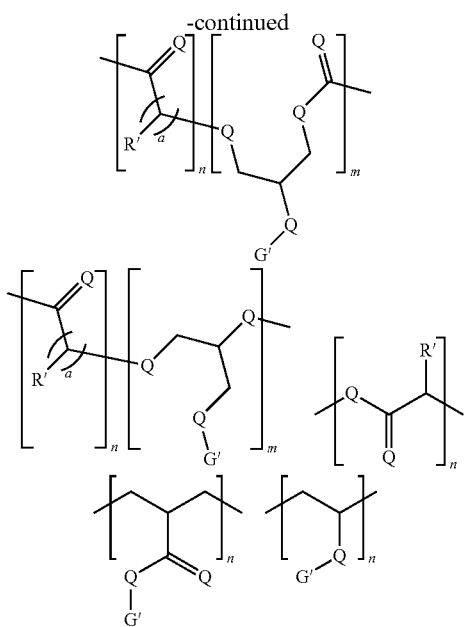

wherein:
each Q is independently selected from O, S, Se, and NH;
Q' is independently selected from O, S, Se, or NH;
G' is each independently selected from the following structures:

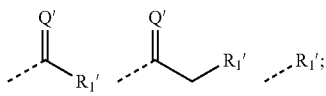

$R'_1$ is selected from among a hydrogen, straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R'_1$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or $R'_1$ is selected from among a photocrosslinkable or ionically crosslinkable group;

$R'_2$ is selected from among hydrogen, a straight or branched alkyl, cycloalkyl, aryl, olefin, silyl, alkylsilyl, arylsilyl, alkylaryl, fluorocarbon, or arylalkyl chain of 1-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

m, n, a, or b are each independently selected from an integer of 1-1000;

each polymeric terminal group is selected from among amines, thiols, amides, phosphates, sulphates, hydroxides, metals, alkanes, alkenes and alkynes.

In the various aspects disclosed herein, the oligomer or polymer represented by one of the above-noted formulas can be a linear, comb, branched, or dendritic oligomer or polymer. The oligomer or polymer represented by one of the above-noted formulas can also comprise one or more reactive functional groups.

In some embodiments of the various aspects disclosed herein, the porous coating layer comprises poly(caprolactone). In some embodiments, the porous coating layer comprises poly(ε-caprolactone) (PCL).

The porous coating layer can comprise modified or unmodified poly(glycerol-co-ε-caprolactone) co-polymer. In the modified poly(glycerol-co-ε-caprolactone) co-polymer, the free hydroxyl group in the glycerol monomer can be modified with hydrophobic, hydrophilic, cationic and/or anion groups. Without limitations, modifications of the poly(glycerol-co-ε-caprolactone) co-polymer can be varied to optimize one or more desired properties of the co-polymer and consequently those of the porous coating. Desired properties can include, but are not limited to, hydrophobicity, hydrophilicity, ion density, cationic charge, anion charge, and the like.

In the modified or unmodified poly(glycerol-co-ε-caprolactone) co-polymer ratio of caprolactone monomers to glycerol monomers can range from about 100:1 to about 1:100. For example, ratio of caprolactone monomers to glycerol monomers can be from about 90:10 to about 90:10. In some embodiments, ratio of caprolactone monomers to glycerol monomers can be from 95:5 to about 55:45. In some embodiments, ratio of caprolactone monomers to glycerol monomers can be about 90:10, about 80:20, about 70:30, about 60:40, or about 50:50. Without limitations, either the caprolactone or the glycerol monomers can be present in a higher amount than the other.

In some embodiments of the various aspects disclosed herein, the porous coating comprises one or more of the following oligomers or polymers:

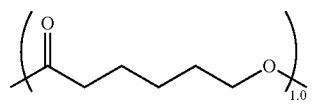

CL-CG-100-0

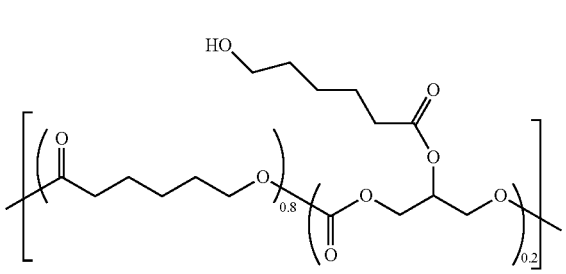

CL-CG-80-20-C6-OH

-continued

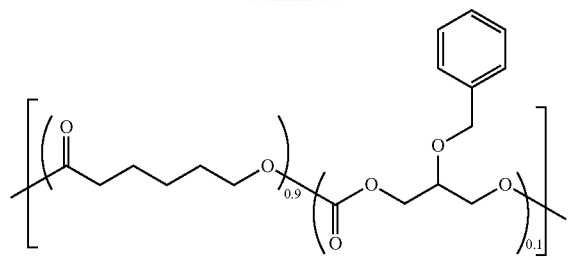

CL-CG-90-10-Bn

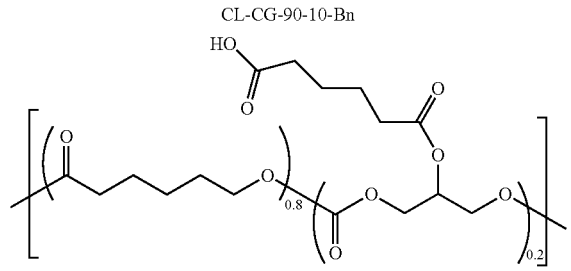

CL-CG-80-20-C5-COOH

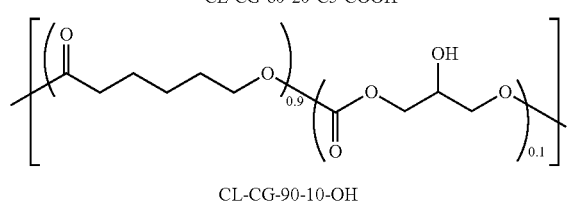

CL-CG-90-10-OH

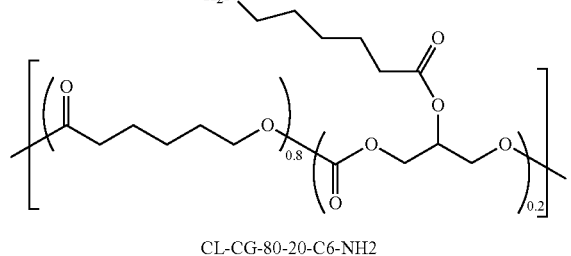

CL-CG-80-20-C6-NH2

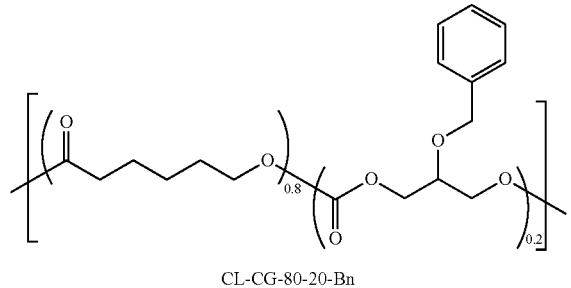

CL-CG-80-20-Bn

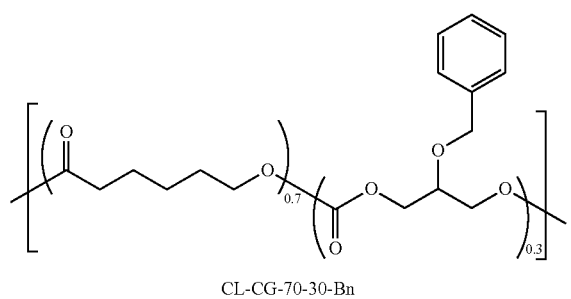

CL-CG-70-30-Bn

-continued

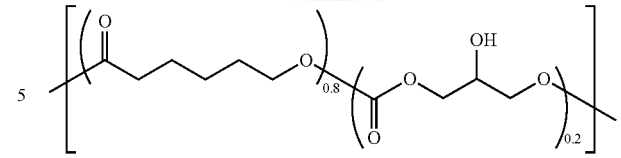

CL-CG-80-20-OH

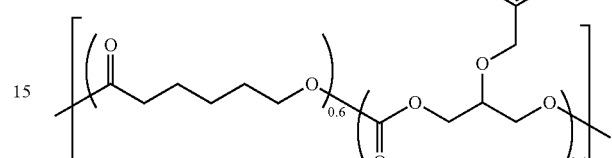

CL-CG-60-40-Bn

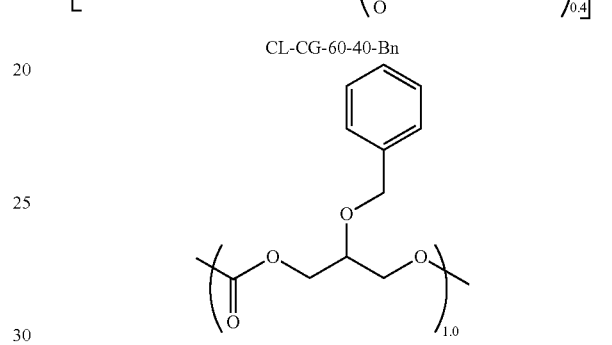

CL-CG-0-100-Bn

Ratio between two different oligomers and/or polymers in the coating can range from about 1000:1 to about 1:1000. In some embodiments of the various aspect disclosed herein, the ratio between two different oligomers and/or polymers can range from about 500:1 to about 1:500, from about 250:1 to about 1:250, or from about 100:1 to about 1:100. In some embodiments, the ratio between two different oligomers and/or polymers can range from about 95:5 to about 45:55. In some embodiments of the various aspects disclosed herein, the ratio between two different oligomers and/or polymers can be about 90:10, about 70:30, or about 50:50.

Exemplary modified or unmodified poly(glycerol-co-ε-caprolactone) co-polymers amenable for use in the porous coating layer are described, for example, in U.S. Pat. No. 7,671,095, content of which is incorporated herein by reference in its entirety.

The porous coating layer can comprise two (e.g., two, three, four, five, six, seven, eight, nine, ten or more) different oligomers or polymers. For example, the porous coating can comprise poly(ε-caprolactone) and the modified or unmodified poly(glycerol-co-ε-caprolactone) co-polymer. Without limitations, the poly(ε-caprolactone) and the modified or unmodified poly(glycerol-co-ε-caprolactone) co-polymer can be present in any desired ratio in the porous coating. For example, ratio of poly(ε-caprolactone) to the modified or unmodified poly(glycerol-co-ε-caprolactone) co-polymer can range from about 1000:1 to about 1:1000. In some embodiments of the various aspect disclosed herein, the ratio of poly(ε-caprolactone) to the modified or unmodified poly(glycerol-co-ε-caprolactone) co-polymer can range from about 500:1 to about 1:500, from about 250:1 to about 1:250, from about 100:1 to about 1:100. In some embodiments, the ratio of poly(ε-caprolactone) to the modified or unmodified poly(glycerol-co-ε-caprolactone) co-polymer can range from about 95:5 to about 45:55. Either the poly(ε-caprolactone) or the modified or unmodified poly(glycerol-co-ε-caprolactone) co-polymer can be present in a higher amount than the other. The preferred ratios for PCL: PGC (modified with a stearic acid) are 9:1 and 8:2.

In some embodiments of the various aspects disclosed herein, ratio of poly(ε-caprolactone) to the modified or unmodified poly(glycerol-co-ε-caprolactone) co-polymer is about 90:10, about 70:30, or about 50:50.

A ratio described in the disclosure can be based on weight, mole or volume. For example, ratio can be weight/weight, mole/mole or volume/volume.

In some embodiments, the modified poly(glycerol-co-ε-caprolactone) co-polymer is functionalized or modified with a lipid. For example, a lipid can be linked to a hydroxyl group of a glycerol monomer in the PGC. A lipid for functionalizing or modifying poly(glycerol-co-ε-caprolactone) co-polymer can be selected from the group consisting of fatty acids, fatty alcohols, glycerolipids (e.g., monoglycerides, diglycerides, and triglycerides), phospholipids, glycerophospholipids, sphingolipids, sterol lipids, prenol lipids, saccharolipids, polyketides, and any combination thereof. In some embodiments, the lipid can be selected from the group consisting of 1,3-Propanediol Dicaprylate/Dicaprate; 10-undecenoic acid; 1-dotriacontanol; 1-heptacosanol; 1-nonacosanol; 2-ethyl hexanol; Androstanes; Arachidic acid; Arachidonic acid; arachidyl alcohol; Behenic acid; behenyl alcohol; mono-diglyceride capric fatty acid emulsifier CAPMUL® MCM C10; Capric acid; capric alcohol; capryl alcohol; Caprylic acid; Caprylic/Capric Acid Ester of Saturated Fatty Alcohol C12-C18; Caprylic/Capric Triglyceride; Caprylic/Capric Triglyceride; Ceramide phosphorylcholine (Sphingomyelin, SPH); Ceramide phosphorylethanolamine (Sphingomyelin, Cer-PE); Ceramide phosphorylglycerol; Ceroplastic acid; Cerotic acid; Cerotic acid; ceryl alcohol; Cetearyl alcohol; Ceteth-10; cetyl alcohol; Cholanes; Cholestanes; cholesterol; cis-11-eicosenoic acid; cis-11-octadecenoic acid; cis-13-docosenoic acid; cluytyl alcohol; coenzyme Q10 (CoQ10); Dihomo-γ-linolenic; Docosahexaenoic acid; egg lecithin; Eicosapentaenoic acid; Eicosenoic acid; Elaidic acid; elaidolinolenyl alcohol; elaidolinoleyl alcohol; elaidyl alcohol; Erucic acid; erucyl alcohol; Estranes; Ethylene glycol distearate (EGDS); Geddic acid; geddyl alcohol; glycerol distearate (type I) EP (Precirol ATO 5); Glycerol Tricaprylate/Caprate; Glycerol Tricaprylate/Caprate (CAPTEX® 355 EP/NF); glyceryl monocaprylate (CAPMUL® MCM C8 EP); Glyceryl Triacetate; Glyceryl Tricaprylate; Glyceryl Tricaprylate/Caprate/Laurate; Glyceryl Tricaprylate/Tricaprate; glyceryl tripalmitate (Tripalmitin); Henatriacontylic acid; Heneicosyl alcohol; Heneicosylic acid; Heptacosylic acid; Heptadecanoic acid; Heptadecyl alcohol; Hexatriacontylic acid; isostearic acid; isostearyl alcohol; Lacceroic acid; Lauric acid; Lauryl alcohol; Lignoceric acid; lignoceryl alcohol; Linoelaidic acid; Linoleic acid; linolenyl alcohol; linoleyl alcohol; Margaric acid; Mead; Melissic acid; melissyl alcohol; Montanic acid; montanyl alcohol; myricyl alcohol; Myristic acid; Myristoleic acid; Myristyl alcohol; neodecanoic acid; neoheptanoic acid; neononanoic acid; Nervonic; Nonacosylic acid; Nonadecyl alcohol; Nonadecylic acid; Nonadecylic acid; Oleic acid; oleyl alcohol; Palmitic acid; Palmitoleic acid; palmitoleyl alcohol; Pelargonic acid; pelargonic alcohol; Pentacosylic acid; Pentadecyl alcohol; Pentadecylic acid; Phosphatidic acid (phosphatidate, PA); Phosphatidylcholine (lecithin, PC); Phosphatidylethanolamine (cephalin, PE); Phosphatidylinositol (PI); Phosphatidylinositol bisphosphate (PIP2); Phosphatidylinositol phosphate (PIP); Phosphatidylinositol triphosphate (PIP3); Phosphatidylserine (PS); polyglyceryl-6-distearate; Pregnanes; Propylene Glycol Dicaprate; Propylene Glycol Dicaprylocaprate; Propylene Glycol Dicaprylocaprate; Psyllic acid; recinoleaic acid; recinoleyl alcohol; Sapienic acid; soy lecithin; Stearic acid; Stearidonic; stearyl alcohol; Tricosylic acid; Tridecyl alcohol; Tridecylic acid; Triolein; Undecyl alcohol; undecylenic acid; Undecylic acid; Vaccenic acid; α-Linolenic acid; γ-Linolenic acid; a fatty acid salt of 10-undecenoic acid, adapalene, arachidic acid, arachidonic acid, behenic acid, butyric acid, capric acid, caprylic acid, cerotic acid, cis-11-eicosenoic acid, cis-11-octadecenoic acid, cis-13-docosenoic acid, docosahexaenoic acid, eicosapentaenoic acid, elaidic acid, erucic acid, heneicosylic acid, heptacosylic acid, heptadecanoic acid, isostearic acid, lauric acid, lignoceric acid, linoelaidic acid, linoleic acid, montanic acid, myristic acid, myristoleic acid, neodecanoic acid, neoheptanoic acid, neononanoic acid, nonadecylic acid, oleic acid, palmitic acid, palmitoleic acid, pelargonic acid, pentacosylic acid, pentadecylic acid, recinoleaic acid (e.g. zinc recinoleate), sapienic acid, stearic acid, tricosylic acid, tridecylic acid, undecylenic acid, undecylic acid, vaccenic acid, valeric acid, α-linolenic acid, or γ-linolenic acid; paraffin; and any combinations thereof.

In some embodiments, the lipid can be functionalized to provide an anionic or cationic functional group on the modified PGC. For example, the lipid can be modified to comprise an amino group, a hydroxyl group, a thiol group, a carbocyclic acid group, and the like.

In some embodiments, the modified poly(glycerol-co-ε-caprolactone) co-polymer comprises an aryl or heteroaryl group linked to a hydroxyl group of a glycerol monomer in the PGC. The linkage can be via a linker. In one embodiment, the modified poly(glycerol-co-ε-caprolactone) co-polymer comprises an optionally substituted benzyl group to a hydroxyl group of a glycerol monomer in the PGC. The poly(glycerol-co-ε-caprolactone) functionalized with a stearic acid is a preferred composition.

In some embodiments, the porous coating comprises collagen or polyacrylamide. In some embodiments, the porous coating is gel or hydrogel and comprises collagen or polyacrylamide.

The thickness and porosity of the porous coating can be selected according to the desired degree of reduction of the translocation speed of target molecules to be detected. Generally, the porous coating has a thickness sufficient to reduce the translocation speed of an analyte molecule (e.g., nucleic acid or protein) passing through the nanopore as compared to the translocation speed in the absence of the porous coating, but not so thick as to prevent translocation of the analyte molecule. For example, the thickness of the porous coating can range from nm to hundreds of micrometers. In some embodiments, the porous coating layer has a thickness of about 1 nm to about 1000 nm.

In some embodiments, the porous coating covers one or both openings of the nanopore.

Additional molecules or components can be present in the porous coating layer. For example, additional components present in the porous coating layer can modulate the interaction of the analyte molecules with the coating. Such additional molecules or components can be covalently or non-covalently liked to the coating.

In embodiments of the various aspects disclosed herein, the coating layer further comprises a denaturation agent. As used herein, the term "denaturation agent" means a compound or composition that inhibits or reduces binding of the analyte molecule to the coating or a targeting entity present in the coating. Exemplary denaturation agents include, but are not limited to, guanidinium chloride, urea, trichloroacetic acid, sulfosalicylic acid, and the like.

Without limitations, the denaturation agent can be encapsulated in the porous coating or covalently linked with the porous coating. For example, the denaturation agent can be present in the porous coating without being covalently linked to another component of the coating or the denaturation agent can be linked to another component of the porous coating. In some embodiments, the denaturation agent is covalently linked to an oligomer/polymer of the porous coating. In some embodiments, the denaturation agent is covalently linked to an oligomer/polymer of the porous coating via a linker.

In some embodiments, the porous coating can include a target binding moiety or analyte binding moiety. As used herein, a "target binding moiety" means a molecule that binds or interacts with an analyte molecule or an analyte capture probe. Generally, the target binding moiety has enhanced or specific binding affinity for a selected analyte or analyte capture probe.

In some embodiments, the porous coating comprises two or more (e.g., three, four, five, six, seven, eight, nine, ten or more) different target binding moieties for capturing different analytes. Without wishing to be bound by a theory, this can allow analysis of multiple analytes in a multiplex format.

In some embodiments, the target binding moiety binds to a capture probe which binds to the analyte. As used herein, the term "capture probe" refers to a molecule that binds or interacts with an analyte molecule and the target binding moiety binds or interacts with the capture probe.

Without limitations, the target binding moiety can be encapsulated in the porous coating or covalently linked with the porous coating. For example, the target binding moiety can be present in the porous coating without being covalently linked to another component of the coating or the target binding moiety can be linked to another component of the porous coating. In some embodiments, the target binding moiety is covalently linked to an oligomer/polymer of the porous coating. In some embodiments, the target binding moiety is covalently linked to an oligomer/polymer of the porous coating via a linker.

Without limitations, the target binding moiety or the capture probe can comprise a wide variety of molecules. Such molecules can include naturally occurring molecules, or recombinant or synthetic molecules. In some embodiments of the various aspects disclosed herein, the target binding moiety and/or the capture probe is selected from the group consisting of antibodies, Fab fragments, scFv, aptamers, nucleic acids, proteins, peptides, other appropriate affinity molecule, and any combinations thereof.

In some embodiments of the various aspects disclosed herein, the target binding moiety and/or the capture probe is a nucleic acid. In some embodiments, the target binding moiety and/or the capture probe is a single stranded oligonucleotide. For example, a single stranded oligonucleotide having a nucleotide sequence substantially complementary to nucleic acid analyte molecule of interest.

When the two components (such as target binding moiety and porous coating, or denaturation agent and porous coating) are covalently linked together, they can be linked together via a linker. As used herein, the term "linker" means an organic moiety that connects two parts of a compound. Linkers typically comprise a direct bond or an atom such as oxygen or sulfur, a unit such as NH, C(O), C(O)NH, SO, $SO_2$, $SO_2NH$ or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), $SO_2$, NH, C(O). The terms linker and spacer are used interchangeably herein. The linker can comprise any combinations of the above. Accordingly, in some embodiments, the linker can comprise hydrocarbons, amino acids, peptides, polyethylene glycol of various lengths, cyclodextrins, and derivatives and any combinations thereof.

In some embodiments, the linker can be a branched linker. The branch point of the branched linker can be at least trivalent, but can be a tetravalent, pentavalent or hexavalent atom, or a group presenting such multiple valencies. In some embodiments, the branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In some embodiments, the branch point is glycerol or derivative thereof, and normal chain sugars such as monosaccharides and polysaccharides. A branched linker can be used to connect two or more (e.g., 2, 3, 4, 5, 6, 7, 8, 9, 10 or more) molecules of interest (which can be same or different) to one affinity ligand; two or more (e.g., 2, 3, 4, 5, 6, 7, 8, 9, 10 or more) affinity ligands (which can be same or different) to one molecule of interest; or two or more (e.g., 2, 3, 4, 5, 6, 7, 8, 9, 10 or more) molecules of interest (which can be same or different) to two or more (e.g., 2, 3, 4, 5, 6, 7, 8, 9, 10 or more) affinity ligands (which can be same or different).

In some embodiments, the linker comprises at least one cleavable linking group. A cleavable linking group is one which is sufficiently stable, but which can be cleaved to release the two parts the linker is holding together. In a preferred embodiment, the cleavable linking group is cleaved at least 10 times or more, preferably at least 100 times faster in the target system or under a first reference condition (which can, e.g., be selected to mimic or represent conditions for binding of analyte molecule to targeting moiety) than under a second reference condition (which can, e.g., be selected to mimic or represent conditions for releasing the analyte molecule from the targeting moiety or releasing the analyte molecule from the targeting moiety.

Cleavable linking groups are susceptible to cleavage agents, e.g., pH, light, redox potential or the presence of degradative molecules. Examples of such degradative agents include: redox agents which are selected for particular substrates or which have no substrate specificity, including, e.g., oxidative or reductive enzymes or reductive agents such as mercaptans that can degrade a redox cleavable linking group by reduction; esterases; amidases; endosomes or agents that can create an acidic environment, e.g., those that result in a pH of five or lower; enzymes that can hydrolyze or degrade an acid cleavable linking group by acting as a general acid, peptidases (which can be substrate specific) and proteases, and phosphatases. The cleavable linking group can comprise esters, peptides, carbamates, acid-labile, reduction-labile, oxidation-labile, disulfides, thiolesters, and modifications thereof. A preferred example are thiolester linkages which are cleaved via a thioester-thiol exchange reaction.

A linker can include a cleavable linking group that is cleavable by a particular enzyme. The type of cleavable linking group incorporated into a linker can depend on the cell to be targeted. In some embodiments, cleavable linking group is cleaved at least 1.25, 1.5, 1.75, 2, 3, 4, 5, 10, 25, 50, or 100 times faster in the presence of the enzyme as compared to in the absence of the enzyme. In some embodiments, the cleavable linking group is cleaved by less than 90%, 80%, 70%, 60%, 50%, 40%, 30%, 20%, 10%, 5%, or 1% in the absence of the enzyme as compared to in the presence of the enzyme.

Exemplary cleavable linking groups include, but are not limited to, redox cleavable linking groups (e.g., —S—S— and —C(R)$_2$—S—S—, wherein R is H or $C_1$-$C_6$ alkyl and at least one R is $C_1$-$C_6$ alkyl such as $CH_3$ or $CH_2CH_3$); phosphate-based cleavable linking groups (e.g., —O—P(O)(OR)—O—, —O—P(S)(OR)—O—, —O—P(S)(SR)—O—, —S—P(O)(OR)—O—, —O—P(O)(OR)—S—, —S—P(O)(OR)—S—, —O—P(S)(ORk)-S—, —S—P(S)(OR)—O—, —O—P(O)(R)—O—, —O—P(S)(R)—O—, —S—P(O)(R)—O—, —S—P(S)(R)—O—, —S—P(O)(R)—S—, —O—P(S)(R)—S—, —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, and —O—P(S)(H)—S—, wherein R is optionally substituted linear or branched $C_1$-$C_{10}$ alkyl); acid cleavable linking groups (e.g., hydrazones, esters, and esters of amino acids, —C=NN— and —OC(O)—); ester-based cleavable linking groups (e.g., —C(O)O—); peptide-based cleavable linking groups, (e.g., linking groups that are cleaved by enzymes such as peptidases and proteases in cells, e.g., —NHCHR$^A$C(O)NHCHR$^B$C(O)—, where R$^A$ and R$^B$ are the R groups of the two adjacent amino acids). A peptide based cleavable linking group comprises two or more amino acids. In some embodiments, the peptide-based cleavage linkage comprises the amino acid sequence that is the substrate for a peptidase or a protease found in cells.

In some embodiments, an acid cleavable linking group is cleaveable in an acidic environment with a pH of about 6.5 or lower (e.g., about 6.0 5.5, 5.0, or lower), or by agents such as enzymes that can act as a general acid. In some embodiments, the linker comprises an acid labile group, e.g., hydrazone or carbamate.

In addition to covalent linkages, two parts of a compound can be linked together by an affinity binding pair. The term "affinity binding pair" or "binding pair" refers to first and second molecules that specifically bind to each other. One member of the binding pair is conjugated with first part to be linked while the second member is conjugated with the second part to be linked. As used herein, the term "specific binding" refers to binding of the first member of the binding pair to the second member of the binding pair with greater affinity and specificity than to other molecules.

Exemplary binding pairs include any haptenic or antigenic compound in combination with a corresponding antibody or binding portion or fragment thereof (e.g., digoxigenin and anti-digoxigenin; mouse immunoglobulin and goat antimouse immunoglobulin) and nonimmunological binding pairs (e.g., biotin-avidin, biotin-streptavidin, biotin-neutravidin, hormone [e.g., thyroxine and cortisol-hormone binding protein, receptor-receptor agonist, receptor-receptor antagonist (e.g., acetylcholine receptor-acetylcholine or an analog thereof), IgG-protein A, IgG-protein G, IgG-synthesized protein AG, lectin-carbohydrate, enzyme-enzyme cofactor, enzyme-enzyme inhibitor, and complementary oligonucleoitde pairs capable of forming nucleic acid duplexes), and the like. The binding pair can also include a first molecule which is negatively charged and a second molecule which is positively charged.

One example of using binding pair conjugation is the biotin-avidin, biotin-streptavidin or biotin-neutravidin conjugation. In this approach, one of the molecule or the peptide is biotinylated and the other is conjugated with avidin or streptavidin. Many commercial kits are also available for biotinylating molecules, such as proteins.

Another example of using binding pair conjugation is the biotin-sandwich method. See, e.g., example Davis et al., Proc. Natl. Acad. Sci. USA, 103: 8155-60 (2006). The two molecules to be conjugated together are biotinylated and then conjugated together using at least one tetravalent avidin-like molecule (e.g., avidin, streptavidin, or neutravidin) as a linker.

The disclosure also provides a method of preparing the article comprising the substrate comprising a nanopore and a porous coating on at least one surface of the substrate. Generally, the method comprises preparing a substrate with a nanopore and depositing or polymerizing the porous coating on at least one surface (e.g., the first surface, the second surface, or both the first and second surfaces) of the substrate. In some embodiments, the method comprises: (i) forming an opening defining a nanopore in a substrate; and (ii) forming porous coating layer on at least one surface (e.g., the first surface, the second surface, or both the first and second surfaces) of the substrate.

The nanopore can be formed in the substrate by any suitable method, such as by using a laser drill or by an etching method or the like. When the nanopore is to have a tapered shape, a selective etching method is particularly suitable. In some embodiments, the nanopore can be formed using a TEM, a SEM, ort the like. In some embodiments, the nanopore can be formed using an electron beam, a focused ion beam, a neutron beam, an alpha-ray, a beta-ray, an X-ray, a γ-ray, or the like, which is emitted from a TEM, a SEM, or the like.

In some embodiments, nanopores can be manufactured by Focused Ion Beam (FIB) drilling on a variety of substrates such as glass and polymeric materials. See, for example, Storm A. J. et al., *Nature Materials* 2003), 2, 537-540 and Siwy, Z. & Fulinski, A. *Phys. Rev. Lett.* (2002), 89, 198103-198106, contents of both which are incorporated herein by reference in their entireties. The fabrication method using FIB on polymeric and glass substrates is identical to the fabrication technique when using FIB on carbon or semiconductor substrates. Fabrication of nanopores using carbon and semiconductors (e.g., silicon) can be undertaken by FIB or electrochemical etching. See, for example, Li, J. et al., *Nature* (2001), 412, 166-169 and Saleh, O. A. et al., '*Nano Letters* (2003), 3, 37-38, 2003, contents of both of which are incorporated herein by reference in their entireties.

The porous coating can be deposited on the substrate in any manner suitable for forming a thin film, such as by a coating or depositing method. Methods of coating or depositing thin films on the surface of a substrate are known in the art. For example, material of the porous coating, e.g., an oligomer/polymer, can be deposited on the substrate surface by electrospinning, electrospraying, ultrasonic spraying the porous coating material near or on the surface of the nanopore.

In some embodiments, the porous coating material can be polymerized or gelled on the surface of the substrate. For example, a composition comprising polymerizable monomers, i.e. a polymerizable composition, can be coated or layered on the substrate surface and the monomers can be polymerized using any means available to one skill in the art for polymerization. For example, monomers can be polymerized using radical polymerization, cationic polymerization, anionic polymerization, reversible addition-fragmentation chain transfer (RAFT) polymerization, atom-transfer radical (ATR) polymerization, or any combinations thereof. In some embodiments, polymerization can occur spontaneously after forming the coating layer on the surface. In some embodiments, the polymerization or gelling can be via mixing, heat, light or chemical induction.

In some embodiments, polymerization can be initiated using a light source. The light source can emit light radially or non-radially. Useful light sources include, but are not limited to, lamps, fiber optics devices, lasers, etc. . . . . For initiation polymerization, light can be applied for a period of seconds to several minutes or hours. For example, the light can be applied for about 10 seconds to about 5 minutes. The light source can allow variation of the wavelength of light and/or the intensity of the light. Light of any wavelength can be used based on the monomers utilized. For example, polymerization can be initiated using UV light (200-500 nm). In certain embodiments, long UV rays can be used. In other embodiments, short UV rays can be used. In some embodiments, polymerization can be initiated using visible light (400-800 nm). In certain embodiments, polymerization can be initiated using blue light (420-500 nm). In certain embodiments, polymerization can be initiated using green light (500-575 nm). In some embodiments, polymerization can be initiated using IR light (800-2500 nm). The output of light can be controlled to provide greater control over the polymerization reaction. Control over the reaction in turn results in control over the characteristics and/or properties of the resulting polymer. In certain embodiments, the intensity of light ranges from about 500 to about $10^6$ μW/cm$^2$. In some embodiments, the intensity of light is about 4000, about 5000, about 6000, about 7000, about 8000, or about 9000 μW/cm$^2$. In some embodiments, the intensity of light is about 200,000-500,000 μW/cm$^2$.

When a light source is used for initiation the polymerization, the composition can further comprise one or a combination of two or more photo-initiators. Photo-initiators produce reactive free radical species that initiate the crosslinking and/or polymerization of monomers upon exposure to light. Any photo-initiator can be used in the crosslinking and/or polymerization reaction. Photoinitiated polymerizations and photo-initiators are discussed in detail in Rabek, Mechanisms of Photophysical Processes and Photochemical Reactions in Polymers, New York: Wiley & Sons, 1987; Fouassier, Photoinitiation, Photopolymerization, and Photocuring, Cincinnati, Ohio: Hanser/Gardner; Fisher et al., 2001, Annu. Rev. Mater. Res., 31:171. A photo-initiator can be designed to produce free radicals at any wavelength of light. For example, a photo-initiator can be designed to work using UV light (200-500 nm). In some embodiments, a photo-initiator is designed to work using visible light (400-800 nm). In certain embodiments, a photo-initiator is designed to work using blue light (420-500 nm). In certain embodiments, a photo-initiator is designed to work using green light (500-575 nm). In some embodiments, the photo-initiator is designed to work using IR light (800-2500 nm).

In some embodiments, the photo-initiator can be a peroxide (e.g., ROOR'), a ketone (e.g., RCOR'), an azo compound (e.g., compounds with a —N=N— group), an acylphosphineoxide, a sulfur-containing compound, a quinone. Exemplary photo-initiators include, but are not limited to, acetophenone; anisoin; anthraquinone; anthraquinone-2-sulfonic acid, sodium salt monohydrate; (benzene) tricarbonylchromium; 4-(boc-aminomethyl)phenyl isothiocyanate; benzin; benzoin; benzoin ethyl ether; benzoin isobutyl ether; benzoin methyl ether; benzoic acid; benzophenyl-hydroxycyclohexyl phenyl ketone; 3,3',4,4'-benzophenonetetracarboxylic dianhydride; 4-benzoylbiphenyl; 2-benzyl-2-(dimethylamino)-4'-morpholinobutyrophenone; 4,4'-bis(diefhylamino)benzophenone; 4,4'-bis(dimethylamino) benzophenone; Michler's ketone; camphorquinone; 2-chlorothioxanthen-9-one; 5-dibenzosuberenone; (cumene) cyclopentadienyliron(II) hexafluorophosphate; dibenzosuberenone; 2,2-diefhoxyacetophenone; 4,4'-dihydroxybenzophenone; 2,2-dimethoxy2-phenylacetophenone; 4-(dimethylamino)benzophenone; 4,4'-dimethylbenzyl; 2,5-dimethylbenzophenone; 3,4-dimethylbenzophenone; diphenyl(2,4,6-trimethylbenzoyl)phosphine oxide; 2-hydroxy-2-methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methybenzoylformate; 2-methyl-4'-(methylthio)-2-morpholinopropiophenone; 9,10-phenanthrenequinone; 4'-phenoxyacetophenone; thioxanthen-9-one; triarylsulfonium hexafluoroantimonate salts; triarylsulfonium hexafluorophosphate salts; 3-mercapto-1-propanol; 11-mercapto-1-undecanol; 1-mercapto-2-propanol; 3-mercapto-2-butanol; hydrogen peroxide; benzoyl peroxide; 4,4'-dimethoxybenzoin; 2,2-dimethoxy-2-phenylacetophenone; dibenzoyl disulphides; diphenyldithiocarbonate; 2,2'-azobisisobutyronitrile (AIBN); camphorquinone (CQ); eosin; dimethylaminobenzoate (DMAB); dimethoxy-2-phenyl-acetophenone (DMPA); Quanta-cure ITX photosensitizer (Biddle Sawyer); Irgacure 907 (Ciba Geigy); Irgacure 2959 (CIBA Geigy); Irgacure 651 (Ciba Geigy); Darocur 2959 (Ciba Geigy); ethyl-4-N,N-dimethylaminobenzoate (4EDMAB); 1-[-(4-benzoylphenylsulfanyl)phenyl]-2-methyl-2-(4-methylphenylsulfonyl)propan1-one; 1-hydroxy-cyclohexyl-phenyl-ketone; 2,4,6trimethylbenzoyldiphenylphosphine oxide; diphenyl(2,4,6trimethylbenzoyl)phosphine; 2-ethylhexyl-4 dimethylaminobenzoate; 2-hydroxy-2-methyl-1-phenyl-1 propanone; 65% (oligo[2-hydroxy-2-methyl-1-[4-(1methyl-vinyl)phenyl]propanone] and 35% propoxylated glyceryl triacrylate; benzil dimethyl ketal; benzophenone; blend of benzophenone and a-hydroxy-cyclohexyl-phenylketone; blend of Esacure KIP150 and Esacure TZT; blend of Esacure KIP150 and Esacure TZT; blend of Esacure KIP150 and TPGDA; blend of phosphine oxide, Esacure KIP150 and Esacure TZT; difunctional a-hydroxy ketone; ethyl 4-(dimethylamino)benzoate; isopropyl thioxanthone; 2-hydroxy-2methyl-phenylpropanone; 2,4,6,-trimethylbenzoyldipheny 1 phosphine oxide; 2,4,6-trimethyl benzophenone; liquid-blend of 4-methylbenzophenone and benzophenone; oligo (2-hydroxy-2 methyl-1-(4(1-methylvinyl)phenyl)propanone; oligo(2-hydroxy-2-methyl-1-4(1-methylvinyl) phenyl propanone and 2-hydroxy-2-methyl-1-phenyl-1-propanone (monomeric); oligo(2-hydroxy-2-methyl-1-4(1-methylvinyl)phenyl propanone and 2-hydroxy-2-methyl-1-phenyl-1propanone (polymeric); 4-methylbenzophenone; trimethylbenzophenone and methylbenzophenone; and water emulsion of 2,4,6-trimethylbenzoylphosphine oxide, alpha hydroxyketone, trimethylbenzophenone, and 4-methyl benzophenone. In certain embodiments, the photo-initiator is acetophenone; diphenyl(2,4,6-trimethylbenzoyl)phosphine oxide; 4,4'-dimethoxybenzoin; anthraquinone; anthraquinone-2-sulfonic acid; benzene-chromium(O) tricarbonyl; 4-(boc-aminomethyl)phenyl isothiocyanate; benzil; benzoin; benzoin ethyl ether; benzoin isobutyl ether; benzoin methyl ether; benzophenone; benzoic acid; benzophenone/1 hydroxycyclohexyl phenyl ketone, 50/50 blend; benzophenone-3,3',4,4'-tetracarboxylic dianhydride; 4-benzoylbiphenyl; 2-benzyl-2-(dimethyl amino)-4' morpholinobutyrophenone; 4,4'-bis(diethylamino) benzophenone; Michler's ketone; (+)-camphorquinone; 2-chlorothioxanthen-9-one; 5-dibenzosuberenone; 2,2-diethoxyacetophenone; 4,4'-dihydroxybenzophenone; 2,2dimethoxy-2-phenylacetophenone; 4-(dimethylamino)benzophenone; 4,4'-dimethylbenzil; 3,4dimethylbenzophenone; diphenyl (2,4,6-trimethylbenzoyl) phosphine oxide/2-hydroxy methylpropiophenone; 4'-ethoxyacetophenone; 2-ethylanthraquinone; ferrocene; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; methyl benzoylformate; 2-methyl-4'-(methylthio)-2-morpholinopropiophenone; 9,10-phenanthrenequinone; 4'-phenoxyacetophenone; thioxanthen-9-one; triarylsulfonium hexafluorophosphate salts; 3-mercapto-1-propanol; 11-mercapto-1-undecanol; 1-mercapto-2-propanol; and 3-mercapto-2-butanol, all of which are commercially available from Sigma-Aldrich. In certain embodiments, the free radical initiator is selected from the group consisting of benzophenone, benzyl dimethyl ketal, 2-hydroxy-2-methyl-phenylpropanone; 2,4,6-trimethylbenzoyldiphenyl phosphine oxide; 2,4,6-trimethyl benzophenone; oligo(2-hydroxy-2-methyl-1 (4-(1-methylvinyl)phenyl)propanone and 4-methylbenzophenone. In some embodiments, the photo-initiator is dimethoxy-2-phenyl-acetophenone (DMPA), a titanocene, 2-hydroxy-1-(4(hydroxyethoxy)phenyl)-2-methyl-1-propanone, Igracure. In some embodiments, the initiator is 2-hydroxy-1-(4-(hydroxyethoxy) phenyl)-2-methyl-1-propanone (Irgacure 2959, CIBA Chemicals).

An initiator of a cationic or anionic crosslinking and/or polymerization process can be used. Generally, any chromophore or a compound having a plurality of conjugated pi bonds that can be excited by light and can promote an electron from a ground state to an excited state, thus rendering the electron capable of being transferred (either directly or indirectly with the use of a coinitiator, as described below) can be used as an initiator for the polymerization process. Exemplary photo-initiators of cationic crosslinking and/or polymerization include, but are not limited to, titanium tetrachloride, vanadium tetrachloride, bis(cyclopentadienyl)titanium dichloride, ferrocene, cyclopentadienyl manganese tricarbonyl, manganese decacarbonyl, diazonium salts, diaryliodonium salts (e.g., 3,3'-dinitrodiphenyliodonium hexafluoroarsenate, diphenyliodonium fluoroborate, 4-methoxydiphenyliodonium fluoroborate) and triarylsulfonium salts.

In general, photo-initiators are utilized at concentrations ranging between approximately 0.0005% w/v and 5.0% w/v. For example, photo-initiators can be utilized at concentrations of about 0.005% w/v, about 0.01% w/v, about 0.025% w/v, about 0.05% w/v, about 0.075% w/v, about 0.1% w/w, about 0.125% w/v, about 0.25% w/v, about 0.5% w/v, about 0.75% w/v, about 1% w/v, about 1.125% w/v, about 1.25% w/v, about 1.5% w/v, about 1.75% w/v, about 2% w/v, about 2.125% w/v, about 2.25% w/v, about 2.5% w/v, about 2.75% w/v, about 3% w/v, about 3.125% w/v, about 3.25% w/v, about 3.5% w/v, about 3.75% w/v, about 4% w/v, about 4.125% w/v, about 4.25% w/v, about 4.5% w/v, about 4.75% w/v, about 5% w/v or higher, although high concentrations of photo-initiators can be toxic to cells.

In some embodiments, the polymerizable composition further comprises a co-initiator. In some embodiments, the co-initiator is an amine. In some embodiments, a co-initiator is exogenously added. In some embodiments, a co-initiator is not exogenously added, as a reactant molecule already participating in the polymerization serves a secondary role of co-initiator. In some embodiments, the co-initiator is selected from the group consisting of triethanolamine, N-methyl-N,N-diethanolamine, N-ethyl-N,N-diethanolamine, an ester of dimethylaminobenzoic acid, 2,6-diisopropyl-N,N-dimethylaniline, 2-benzyl-2-(dimethylamino)-4'-morpholinobutyrophenone, carbon tetrabromide, [4-[(2-hydroxytetradecyl)oxy]phenyl]phenyliodonium hexafluoroantimonate, Ethylenediamine-N,N,N',N'-tetra(2-propanol), 1,4-dimethylpiperazine, Tribenzylamine, diazabicyclo[2,2,2]octane, N-phenyldiethanolamine, allylthiourea, 4-(Dimethylamino)benzaldehyde, 2,6-Diisopropyl-N, N-dimethylaniline, 7-(Diethylamino)-4-methylcoumarine, 2-Mercaptobenzimidazol, and any combinations thereof.

Without limitations, a monomer in the polymerization can serve the role of co-initiator (e.g. an amine-containing monomer), and the primary photoinitiator can also serve the role of its own co-initiator (e.g. if the photoinitiator contains an amine, one molecule gets excited by light, and another molecule's amine takes part in co-initiation).

In some embodiments, the polymerizable composition further comprises an accelerant, e.g., a polymerization accelerant. As used herein, an "accelerator" for a polymerization reaction refers to a compound that can assist the polymerization of polymerizable material following initiation of the reaction. Generally, an accelerator will promote completion of the polymerization reaction and/or increase the rate that the polymerizable material becomes incorporated into a polymerized product. Compounds with an N-vinyl group can serve as accelerants in the compositions, polymers, and methods disclosed herein. In some embodiments, accelerant is N-vinyl pyrrolidone. Other exemplary accelerants are described in, for example, PCT Publication No. WO2005054304 and PCT Application No. PCT/US2004/038053 (Biocompatible polymerization accelerators), contents of both of which are incorporated herein by reference in their entireties.

Similar to photo-initiators, accelerants are utilized at concentrations ranging between approximately 0.005% w/v and 5.0% w/v. For example, accelerant can be utilized at concentrations of about 0.005% w/v, about 0.01% w/v, about 0.025% w/v, about 0.05% w/v, about 0.075% w/v, about 0.1% w/w, about 0.125% w/v, about 0.25% w/v, about 0.5% w/v, about 0.75% w/v, about 1% w/v, about 1.125% w/v, about 1.25% w/v, about 1.5% w/v, about 1.75% w/v, about 2% w/v, about 2.125% w/v, about 2.25% w/v, about 2.5% w/v, about 2.75% w/v, about 3% w/v, about 3.125% w/v, about 3.25% w/v, about 3.5% w/v, about 3.75% w/v, about 4% w/v, about 4.125% w/v, about 4.25% w/v, about 4.5% w/v, about 4.75% w/v, about 5% w/v or higher, although high concentrations of accelerant can be toxic to cells. In some embodiments, accelerant can be utilized at concentrations of about 0.05% w/v to about 5% w/v. Generally, the concentration of the accelerant should be kept to a minimum if the accelerant exhibits toxicity.

Methods of Use

Nanopores have emerged in recent years as versatile single-molecule detectors. The sensing principle is based on transient interruptions in the ion-current of an electrolyte, induced by the entry, transport, and exit of a particular analyte from the pore. A distinguishing feature of nanopores is that they can be used to analyze not only small molecules, but also long biopolymers, such as DNA and RNA, with resolution on the order of the nanopore length (several nm). A well-studied system involves the lipid-embedded α-hemolysin (α-HL) protein pore, which can accommodate various types of biopolymers. α-HL has been used extensively to discriminate between DNA and RNA sequences, to study DNA unzipping kinetics, orientation of entry, DNA-protein interactions, and peptide transport. An important outcome of these studies has been the realization that threaded biopolymer dynamics is governed by the biopolymer's interactions with the nanopore walls. This notion has been utilized for the detection of small molecules, metal-ions, and the discrimination of enantiomer drugs, by employing molecular biology methods to modify the α-HL nanopore. However, the range of sensing applications using α-HL is limited by its fixed dimensions and the delicate nature of a lipid membrane.

Nanopores incorporated in thin solid-state inorganic membranes are highly promising materials, since the nanopore volume can be reduced to a few nm in all dimensions, on par with biological membrane channels. In addition, the planar geometry permits high-resolution fabrication and characterization. Further, the fabrication of high-density nanopore arrays is possible, setting the stage for high-throughput bimolecular analysis, in particular ultra-fast DNA or protein sequencing.

Coated nanopores in thin solid-state inorganic membranes enable a broad range of nanopore sensing applications. Because a variety of coatings may be used, as suitable for each sensing application, the detection mechanism is not limited to electrical detection only. Optical detection mechanisms can be preferable for certain embodiments. The present technology is highly scalable, with both optically- and electrically-addressable nanopore array assemblies enabling detection over a surface area. Without limitations, by controlling the properties of the porous coating, the characteristics of the nanopore can be refined for a variety of applications.

Electrical detection mechanisms rely on ion current sensing. Ion current sensing for individual nanopores and nanopore arrays typically uses a potassium chloride or other electrolyte solution (salt solution). A substrate comprising a nanopore separates two reservoirs of ionic solution. When voltage is applied across the two reservoirs, the potential drop almost entirely occurs at the nanopore. Therefore the ionic conductance or resistance between the two reservoirs is also the conductance or resistance of the nanopore. The nanopore conductance transiently drops when a molecule (e.g. DNA or protein) enters and exits the nanopore, allowing its detection. By analyzing the transient conductance spikes, the properties of biopolymers (size, charge, structure) can be investigated. This detection scheme can be parallelized using an array of nanopores with individual electrodes situated at each chamber. The individual electrodes are then uniquely addressable using techniques well-known in the semiconductor industry.

Optical detection schemes are also effective in chemically-modified nanopore sensors. Nanopore surfaces may be chemically functionalized with fluorescent molecules. In this mode of sensing, a voltage is used to drive molecules through the nanopores, while a microscope is used to sense light output from each nanopore in the membrane. The nanopore (or array of nanopores) is assembled in a cell containing a transparent window allowing optical probing of the membrane, while fluorescent molecules are detected as they occupy the pore. In various applications, creating chemically-modified nanopores entails introducing fluorescent molecules only at the pore (as opposed to over an area of the membrane) by performing two complementary reactions at opposite sides of the membrane. The size of each pore in the array can be either uniform or varying (for example, a gradient of size and shape across a portion of the membrane). The location of each pore in the array is specified during the fabrication process so that each pore has a known location. Alternately, the pores can be optically detected using fluorescent molecules. The spacing between pores is chosen so that optical probing would have sufficient resolution to address each pore (e.g., approximately 500 nm spacing between adjacent pores).

Accordingly, the disclosure also provides a method of detecting the presence, or identity, or a physical characteristic (for example, but not limited to, length, sequence, interaction with a second molecule) of an analyte molecule. As used herein, the term "analyte" is a broad term and is used in its ordinary sense and refers, without limitation, to any compound or composition the identity, presence or concentration of which is sought in a sample. For example, an analyte can be a nucleic acid, an amino acid, peptide, protein, growth factor, saccharide, or a molecule produced by a cell. In some embodiments of the various aspects disclosed herein, the analyte includes a biopolymer. Exemplary biopolymers include, but are not limited to, single-stranded DNA, double-stranded DNA, RNA, a nucleic acid polypeptide, a protein, a peptide, and the like.

According to some embodiments of the various aspects disclosed herein, a method for characterizing an analyte includes receiving the analyte through the nanopore, and detecting variations in current flow through nanopore. The variations in current correspond to translocation of the analyte through the nanopore. For example, the inventors have discovered that single-stranded nucleic acids have different translocation dynamics through the nanopore than double-stranded nucleic acids of same length. Thus, the coated nanopore substrate disclosed herein can be used to distinguish between single-stranded and double-stranded nucleic acids. Further, the coated nanopore substrate disclosed herein can be used to determine interactions of different molecules with each other, for example, nucleic acid/nucleic acid interactions, nucleic acid/protein interactions, protein/protein interactions and the like. In some embodiments, the nanopore current varies with length of the analyte, e.g., length of a nucleic acid or protein analyte.

Methods of using nanopores for characterizing analytes are well known in the art. For example, the use of nanopores in single-molecule detection is described, for example, in Kasianowicz et al., *Proc Nat Acad Sci* (1996), 93:13770-13773; Akeson et al., *Biophys. J* (1999), 77: 3227-3233; and Meller et al., *Proc Nat Acad Sci* (2000), 97: 1079-1084, contents of all of which are herein incorporated by reference in their entireties.

Nanopore detection techniques have been used for biomolecule detection. For example, various nanopore sequencing methods have been proposed. In 1994, Bezrukov, Vodyanoy and Parsegian showed that one can use a biological nanopore as a Coulter counter to count individual molecules (*Counting polymers moving through a single ion channel*, Nature 370, 279-281 (1994) incorporated, herein, by reference). In 1996, Kasianowicz, Brandin, Branton and Deamer proposed an ambitious idea for ultrafast single-molecule sequencing of single-stranded DNA molecules using nanopore ionic conductance as a sensing mechanism (*Characterization of individual polynucleotide molecules using a membrane channel*, Proc. Nat. Acad. Sci. USA 93 13770-13773 (1996), incorporated herein by reference). Since then, several groups have explored the potential of α-hemolysin protein pore as a possible candidate for achieving this objective. (See, for example: Akeson, M, Branton, D, Kasianowicz J, Brandin E and Deamer D, (1999) Biophys. J. 77: 3227-3233; Meller A, Nivon L, Brandin E, Golovchenko J, Branton D, (2000) *Proc Nat Acad Sci* 97: 1079-1084; Braha, O.; Gu, L. Q.; Zhou, L.; Lu, X.; Cheley, S.; Bayley, H. *Nat. Biotech.* 2000; Meller A. Nivon L, and Branton, D. (2001) *Phys. Rev. Lett.* 86:3435-3438; Meller A, and Branton D. (2002) *Electrophoresis,* 23:2583-2591; Bates M, Burns M, and Meller A (2003) *Biophys. J.* 84:2366-2372; Zwolak M, Di Ventra M (2007). *Rev Mod Phys* 80:141-165, each of which is herein incorporated by reference in its entirety.) The methods seek to effectively determine the order in which nucleotides occur on a DNA strand (or RNA). The theory behind nanopore sequencing concerns observed behavior when the nanopore is immersed in a conducting fluid and a potential (voltage) is applied across it. Under these conditions an electrical current that results from the conduction of ions through the nanopore can be observed. The amount of current which flows is sensitive to the size of the nanopore. When a biomolecule passes through the nanopore, it will typically create a change in the magnitude of the current flowing through the nanopore. Electronic sensing techniques are used to detect the ion current variations, thereby sensing the presence of the biomolecules U.S. Pat. No. 6,428,959, the entire contents of which are herein incorporated by reference, describes methods for determining the presence of double-stranded nucleic acids in a sample. In the methods described, nucleic acids present in a fluid sample are translocated through a nanopore, e.g., by application of an electric field to the fluid sample. The current amplitude through the nanopore is monitored during the translocation process and changes in the amplitude are related to the passage of single- or double-stranded molecules through the nanopore. Those methods find use in a variety of applications in which the detection of the presence of double-stranded nucleic acids in a sample is desired.

Without limitations, the article comprising the porous coating coated substrate disclosed herein can be used for, but is not limited to, to sequence nucleic acids; to sequence proteins; to detect a nucleic acid sequence; to detect a protein to detect a protein to nucleic acid interaction(s); to detect protein to protein interaction(s); to detect nucleic acid to nucleic acid interaction(s); to determine the length of a nucleic acid sequence, e.g., for genomic or transcriptomic analysis for DNA or RNA, respectively; to determine the length of an amino acid sequence for proteomic analysis; or any combinations thereof.

According to some embodiments, the disclosure provides a method for identifying an analyte using a porous coating coated substrate disclosed herein. The method comprising exposing the coated substrate to a solution comprising the analyte of interest, wherein the porous coating comprises a analyte binding moiety; allowing the analyte to bind with the analyte binding moiety; optionally washing any unbound analyte; releasing the bound analyte from the analyte binding moiety; and detecting variation in current flow through the nanopore, wherein the variation in current correspond to translocation of the analyte through the nanopore. Any method or reagent available to one of skill in the art for releasing two bound molecules from each other can be used. Some examples include, but are not limited to, changes in pH, addition of thiols, change in ionic strength, heating, enzymatic degradation, chemical treatments, and the like. Alternatively, a reporter species can be measured which is directly related to the analyte of interest.

In some embodiments, the analyte is a nucleic acid. Thus, in some embodiments, the disclosure provides a method for identifying a nucleic acid sequence using a porous coating coated substrate disclosed herein. The method comprising exposing the coated substrate to a solution comprising the nucleic acid of interest, wherein the porous coating comprises a nucleic acid binding moiety, for example an oligonucleotide comprising a nucleotide sequence substantially complimentary to at least part of the nucleotide sequence of the nucleic acid of interest; allowing the nucleic acid of interest to bind with the nucleic acid binding moiety; optionally washing any unbound nucleic acid of interest; releasing the nucleic acid of interest from the nucleic acid binding moiety; and detecting variation in current flow through the nanopore, wherein the variation in current correspond to translocation of the nucleic acid analyte through the nanopore.

According to still some embodiments, the disclosure provides a method for identifying an analyte using a porous coating coated substrate disclosed herein. The method comprising exposing the coated substrate to a solution comprising the analyte of interest, wherein the porous coating comprises a target binding moiety; allowing the analyte to bind with the target binding moiety; optionally washing any unbound analyte; releasing the analyte/target binding moiety as a complex; and detecting variation in current flow through the nanopore, wherein the variation in current correspond to translocation of the analyte/target binding moiety complex through the nanopore. Any method or reagent available to one of skill in the art for releasing two bound molecules from each other can be used. Some examples include, but are not limited to, changes in pH, addition of thiols, change in ionic strength, heating, enzymatic degradation, chemical treatments, and the like. Without wishing to be bound by a theory, translocation time and/or dynamics for analyte/target binding moiety complex are different from the translocation time and/or dynamics of unbound analyte and the target binding moiety.

When the target binding moiety is linked to the porous coating via a linker comprising a cleavable group, the analyte/target binding moiety complex can be released by exposing the substrate to a condition under which the cleavable group is cleaved.

In some embodiments, the analyte is a nucleic acid and the method comprises: exposing the coated substrate to a solution comprising the nucleic acid of interest, wherein the porous coating comprises a nucleic acid binding moiety, for example an oligonucleotide comprising a nucleotide sequence substantially complimentary to at least part of the nucleotide sequence of the nucleic acid of interest; allowing the nucleic acid of interest to bind with the nucleic acid binding moiety; optionally washing any unbound nucleic acid of interest; releasing the nucleic acid and the nucleic acid binding moiety as a complex from the porous coating interest; and detecting variation in current flow through the nanopore, wherein the variation in current correspond to translocation of the nucleic acid bound to the nucleic acid binding moiety through the nanopore. As noted elsewhere, inventors have discovered that translocation time and/or dynamics of double stranded nucleic acids are different from those of single-stranded nucleic acids. Thus, a nucleic acid has translocation time and/or dynamics, i.e., variations in current, that are different when the nucleic acid is bound to a nucleic acid binding moiety compared to when not bound to a nucleic acid binding moiety.

In some other embodiments, the method comprises: preparing an analyte/capture probe complex; exposing the coated substrate to a solution comprising the analyte/capture probe complex; allowing the capture probe in the analyte/capture probe complex to bind with the porous coating; optionally washing any unbound analyte/capture probe complex; releasing the analyte from the porous coating bound analyte/capture probe complex; and detecting variation in current flow through the nanopore, wherein the variation in current correspond to translocation of the analyte through the nanopore. In some embodiments, the capture probe comprises a reactive functional group for linking the capture probe to the porous coating. In some embodiments, the porous coating comprises a reactive function group for binding the capture probe.

In some other embodiments, the method comprises: preparing a nucleic acid/capture probe, wherein the capture probe is a nucleic acid binding moiety, for example an oligonucleotide comprising a nucleotide sequence substantially complimentary to at least part of the nucleotide sequence of the nucleic acid of interest; exposing the coated substrate to a solution comprising the nucleic acid/capture probe complex; allowing the capture probe in the complex to bind with the porous coating; optionally washing any unbound nucleic acid/capture probe complex; releasing the nucleic acid from the porous coating bound nucleic acid/capture probe complex; and detecting variation in current flow through the nanopore, wherein the variation in current flow correspond to translocation of the nucleic acid through the nanopore. In some embodiments, the capture probe is an nucleic acid.

In some embodiments, the method comprises: preparing an analyte/capture probe complex; exposing the coated substrate to a solution comprising the analyte/capture probe complex, wherein the porous coating comprises a target binding moiety that binds or interacts with the analyte/capture probe complex; allowing the analyte/capture probe complex to bind with the target binding moiety in the porous coating; optionally washing any unbound analyte/capture probe complex; releasing the analyte from the target binding moiety bound analyte/capture probe complex; and detecting variation in current flow through the nanopore, wherein the variation in current correspond to translocation of the analyte through the nanopore.

In some embodiments of the various aspects disclosed herein, the porous coating comprises two or more (e.g., three, four, five, six, seven, eight, nine, ten or more) different target binding moieties for capturing different analytes. Without wishing to be bound by a theory, this can allow analysis of multiple analytes in a multiplex format. Analyte characterization methods using substrates comprising porous coating with more than one target binding moieties can be used for analysis of multiple analytes in multiplex format. For example, bound analytes and/or analyte/capture probe complexes can be released in a sequential manner thereby allowing characterization of multiple analytes.

The disclosure also provides a method for sizing the length of an analyte. Generally, the method comprises: exposing the coated substrate to a solution comprising the analyte of interest; and detecting variation in current flow through the nanopore, wherein the variation in current correspond to length of the analyte.

In one embodiment of this, the analyte is a nucleic acid (single-stranded or double-stranded) and the method comprises: exposing the coated substrate to a solution comprising the nucleic acid; and detecting variation in current flow through the nanopore, wherein the variation in current corresponds to length of the nucleic acid.

In another embodiment, the analyte is a protein and the method comprises: exposing the coated substrate to a solution comprising the protein; and detecting variation in current flow through the nanopore, wherein the variation in current corresponds to length of the nucleic acid.

The inventors have also discovered that, in addition to detecting DNA and proteins, the substrate comprising the 3D porous coating can also be used for detecting synthetic polyelectrolytes like PAA (polyacrylic acid). This is useful as PAA is used as a scale inhibitor in the oil industry to improve oil recovery. Determining the amount of scale inhibitor is useful—this is a simple and sensitive way to do it. Thus, the above disclosed methods for identifying/characterizing analytes, such as nucleic acids and proteins, can also be used for detection/characterization of polyelectrolytes, including but not limited to, anionic polyelectrolytes and/cationic polyelectrolytes.

Embodiments of the various aspects disclosed herein can also be described by one or more of the following numbered paragraphs:

1. An article comprising: (i) a substrate having a first surface and as second surface; (ii) at least one nanopore extending through the substrate, thus forming a channel connecting from the first surface to the second surface of the substrate, wherein the nanopore has a first opening that opens to the first surface of the substrate and a second opening that opens to the second surface of the substrate; and (iii) a porous coating on at least one of the first or second surface of the substrate.
2. The article of paragraph 1, wherein the article comprises a 3D porous coating on both the first surface and the second surface of the substrate.
3. The article of paragraph 1 or 2, wherein the 3D porous coating covers at least one of the first opening or the second opening of the at least one nanopore.
4. The article of any of paragraphs 1-3, wherein the 3D porous coating covers both the first opening and the second opening of said at least one nanopore
5. The article of any of paragraphs 1-4, wherein the substrate is a membrane or thin solid-state, polymeric, lipid, or solid-like film.
6. The article of any of paragraphs 1-5, wherein the substrate comprises Si, $SiO_2$, $SiN_4$, quartz, alumina, nitrides, metals, polymers, or any combinations thereof.
7. The article of any of paragraphs 1-6, wherein the nanopore opening is from about 2 nm to about 10,000 nm.
8. The article of any of paragraphs 1-7, wherein the 3D porous coating comprises nanofibers or nanoparticles.
9. The article of any of paragraphs 1-8, wherein the 3D porous coating comprises an electrospun polymer.

10. The article of any of paragraphs 1-9, wherein the 3D porous coating comprises an electrosprayed or ultrasonically sprayed polymer.
11. The article of any of paragraphs 1-10, wherein the 3D porous coating is a gel or hydrogel.
12. The article of any of paragraphs 1-11, wherein the 3D porous coating comprises collagen or polyacrylamide.
13. The article of any of paragraphs 1-12, wherein the 3D porous coating further comprises a target binding moiety.
14. The article of any of paragraphs 1-13, wherein the target binding moiety is selected from the group consisting of antibodies, Fab fragments, scFv, aptamers, nucleic acids, proteins, peptides, other affinity molecule, and any combinations thereof.
15. The article of any of paragraphs 1-14, wherein the target binding moiety binds to or interacts with a nucleic acid.
16. The article of any of paragraphs 1-15, wherein the target binding moiety is a nucleic acid.
17. The article of any of paragraphs 1-16, wherein the nucleic acid is single-stranded DNA, double-stranded DNA, RNA, mRNA, miRNA, or pre-miRNA.
18. The article of any of paragraphs 1-17, wherein the target binding moiety binds to or interacts with a protein.
19. The article of any of paragraphs 1-18, wherein the target binding moiety is selected from antibodies, Fab fragments, scFv, and aptamers.
20. The article of any of paragraphs 1-19, wherein the targeting moiety is covalently linked to the 3D porous coating.
21. The article of any of paragraphs 1-20, wherein the 3D porous coating further comprises a denaturing agent.
22. The article of any of paragraphs 1-21, wherein the denaturing agent is selected from the group consisting of guanidinium chloride, urea, trichloroacetic acid, sulfosalicylic acid, and any combinations thereof
23. The article of any of paragraphs 1-22, wherein the 3D porous coating comprises a linear, comb, branched, or dendritic oligomer or polymer.
24. The article of any of paragraphs 1-23, wherein the oligomer or polymer further comprises a reactive functional group.
25. The article of any of paragraphs 1-24, wherein the reactive group is selected from the group consisting of hydroxyl, alcohols, amines, azides, alkynes, alkenes, NHS, MAL, thiols, thials, sulfinos, acids, carboxylic acids, and any combinations thereof.
26. The article of any of paragraphs 1-25, wherein the 3D porous coating comprises an oligomer or polymer represented by one or more of the following formulas:

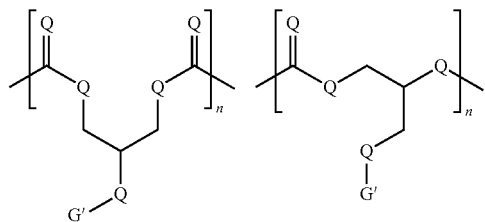

-continued

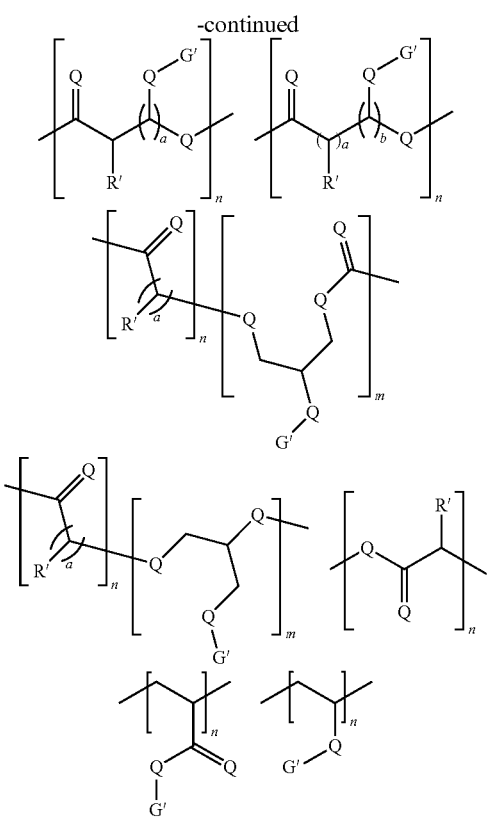

wherein:

each Q' is independently selected from O, S, Se, or NH;
each G' is independently selected from the following structures:

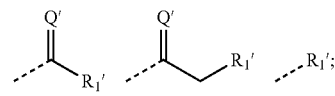

$R'_1$ is selected from among a hydrogen, straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or $R'_1$ is selected from among poly(ethylene glycol), poly (ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or $R'_1$ is selected from among a photocrosslinkable or ionically crosslinkable group;

$R'_2$ is selected from among hydrogen, a straight or branched alkyl, cycloalkyl, aryl, olefin, silyl, alkylsilyl, arylsilyl, alkylaryl, fluorocarbon, or arylalkyl chain of 1-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

m, n, a, or b are each independently selected from an integer of 1-1000;

each polymeric terminal group is selected from among amines, thiols, amides, phosphates, sulphates, hydroxides, metals, alkanes, alkenes and alkynes.

27. The article of any of paragraphs 1-26, wherein the 3D porous coating comprises poly (ε-caprolactone).
28. The article of any of paragraphs 1-27, wherein the 3D porous coating comprises a copolymer comprising caprolactone monomers.
29. The article of any of paragraphs 1-28, wherein the copolymer is a modified or unmodified poly(glycerol-co-ε-caprolactone) co-polymer.
30. The article of any of paragraphs 1-29, wherein the poly(glycerol-co-ε-caprolactone) co-polymer is modified to comprise at least one group selected from lipids, hydrophobic groups, hydrophilic groups, cationic groups, anion groups, and any combinations thereof.
31. The article of any of paragraphs 1-30, wherein the 3D porous coating comprises at least one oligomer or polymer selected from the group consisting of:

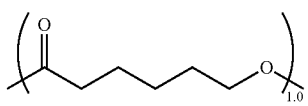

CL-CG-100-0

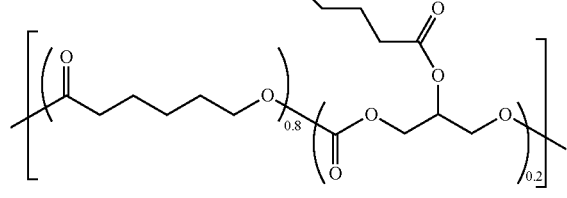

CL-CG-80-20-C6-OH

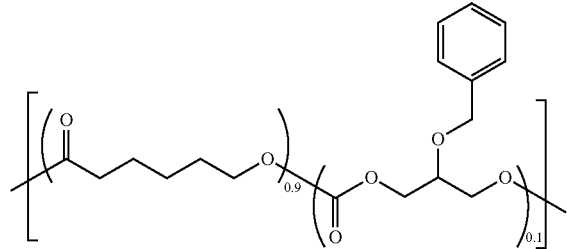

CL-CG-90-10-Bn

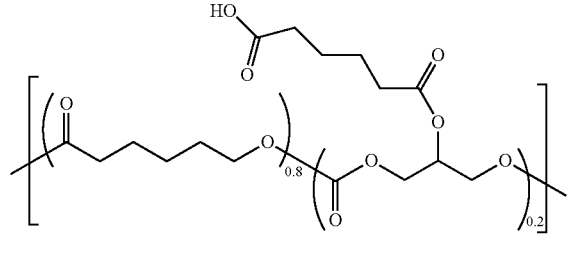

CL-CG-80-20-C5-COOH

-continued

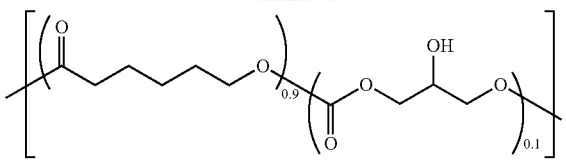

CL-CG-90-10-OH

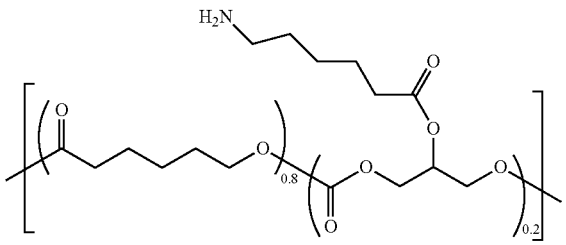

CL-CG-80-20-C6-NH2

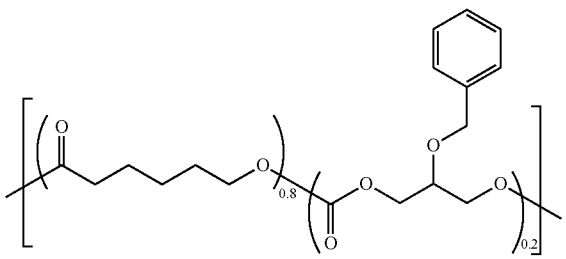

CL-CG-80-20-Bn

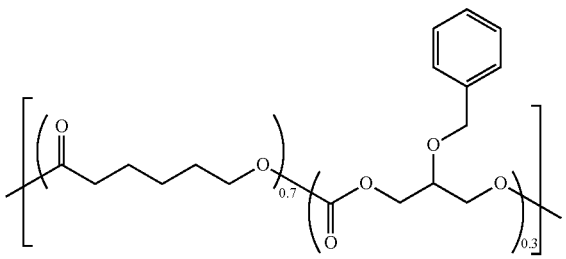

CL-CG-70-30-Bn

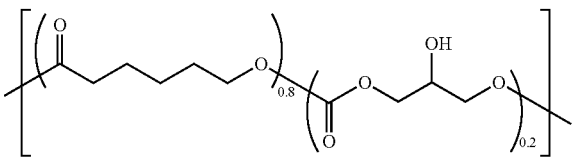

CL-CG-80-20-OH

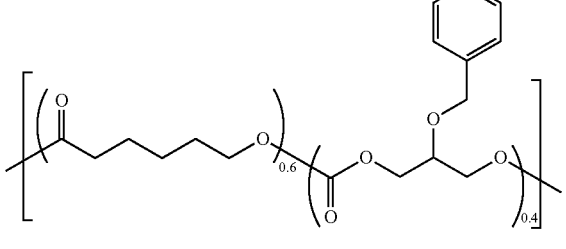

CL-CG-60-40-Bn

-continued

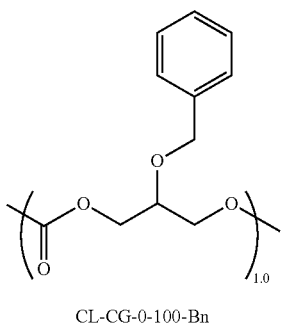

CL-CG-0-100-Bn and any combinations thereof.

32. The article of any of paragraphs 1-31, wherein the polymer is a linear, comb, branched, or dendritic oligomer or polymer represented by one of the following formulas:

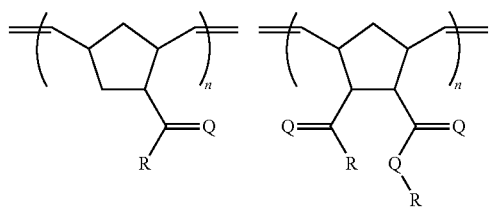

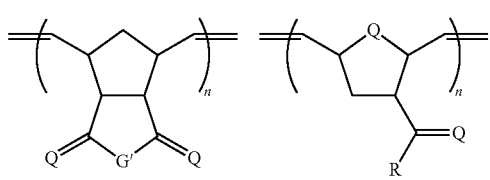

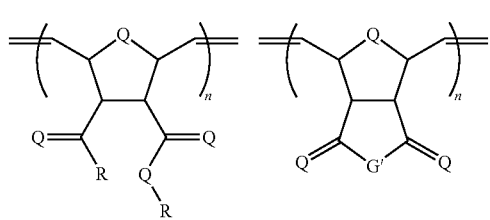

wherein:

Q is independently selected from among O, S, Se, or NH;

G' is each independently selected from among the following structures:

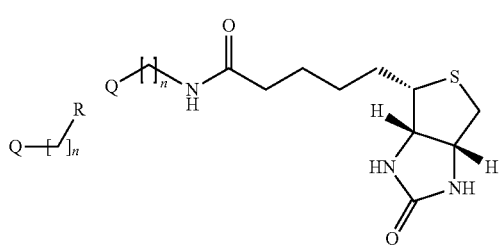

-continued

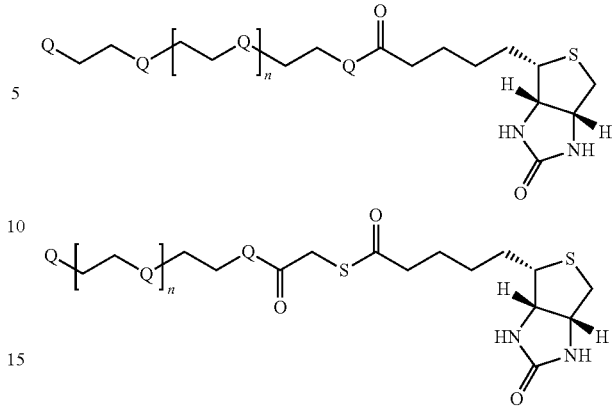

R is selected from among a hydrogen, straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or R is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or R is selected from among a photocrosslinkable or ionically crosslinkable group;

n is independently selected from an integer of 1-1000;

each polymeric terminal group is selected from among amines, thiols, amides, phosphates, sulphates, hydroxides, metals, alkanes, alkenes and alkynes.

33. The article of any of paragraphs 1-32, wherein the 3D porous coating comprises a hydrophobic, hydrophilic, cationic and/or anion group.

34. The article of any of paragraphs 1-33, wherein the 3D porous coating alters the rate at which a molecule transits or translocates through the nanopore relative to when no 3D coating is present.

35. A method of preparing an article comprising a substrate comprising at least one nanopore and a 3D porous coating on at least one surface of the substrate, the method comprising:
   (i) preparing a substrate with a nanopore; and
   (ii) depositing or polymerizing a polymer or oligomer on at least one surface (e.g., the first surface, the second surface, or both the first and second surfaces) of the substrate, thereby forming a 3D porous coating on said at least one surface.

36. The method of paragraph 35, wherein said depositing is via electrospinning, electrospraying or ultrasonic spraying said polymer or oligomer on said at least one surface of the substrate.

37. The method of paragraph 35 or 36, wherein said depositing comprises polymerizing said oligomer or polymer on said at least one surface of the substrate with a polymerizable composition and inducing polymerization.

38. The method of any of paragraphs 35-37, wherein said polymerization comprises radical polymerization, cationic polymerization, anionic polymerization, reversible addition-fragmentation chain transfer (RAFT) polymerization, atom-transfer radical (ATR) polymerization, or any combinations thereof.
39. The method of any of paragraphs 35-38, wherein said polymerization is initiated using a light source.
40. The method of any of paragraphs 35-39, wherein said depositing comprises gelling or crosslinking said oligomer or polymer above the nanopore via mixing, heat, light, or chemical induction on said at least one surface of the substrate.
41. The method of any of paragraphs 35-40, wherein the said polymer or oligomer is a linear, comb, branched or dendritic oligomer or polymer and comprises a structure represented by one or more of the following formulas:

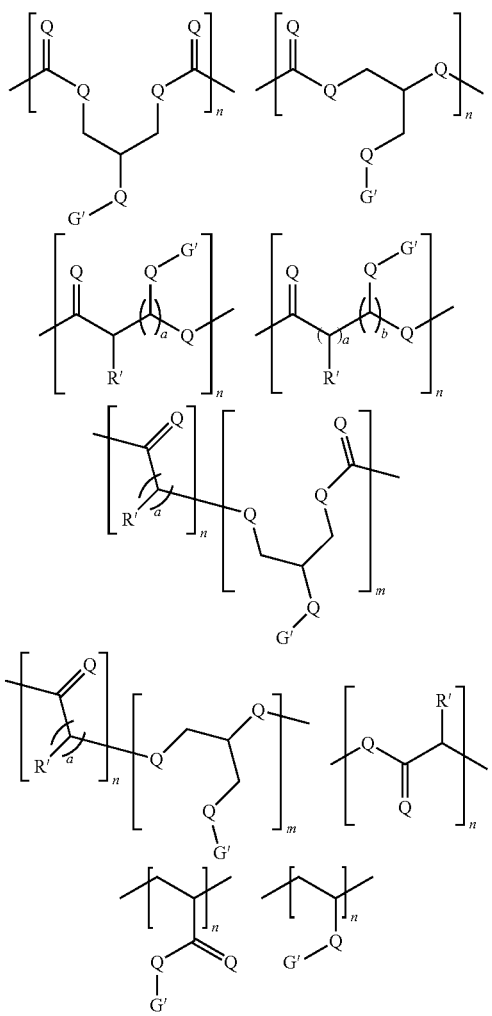

wherein:
each Q' is independently selected from O, S, Se, or NH;
each G' is independently selected from the following structures:

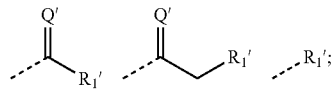

R'$_1$ is selected from among a hydrogen, straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or R'$_1$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or R'$_1$ is selected from among a photocrosslinkable or ionically crosslinkable group;

R'$_2$ is selected from among hydrogen, a straight or branched alkyl, cycloalkyl, aryl, olefin, silyl, alkylsilyl, arylsilyl, alkylaryl, fluorocarbon, or arylalkyl chain of 1-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

m, n, a, or b are each independently selected from an integer of 1-1000;

each polymeric terminal group is selected from among amines, thiols, amides, phosphates, sulphates, hydroxides, metals, alkanes, alkenes and alkynes.

42. The method of any of paragraphs 35-41, wherein the said polymer or oligomer comprises a reactive functional group.
43. The method of any of paragraphs 35-42, wherein the functional group is selected from the group consisting of hydroxyl, alcohols, amines, azides, alkynes, alkenes, NHS, MAL, thiols, thials, sulfinos, acids, carboxylic acids, and any combinations thereof.
44. The method of any of paragraphs 35-43, wherein the oligomer or polymer is a linear, comb, branched, or dendritic oligomer or polymer represented by one of the following formulas:

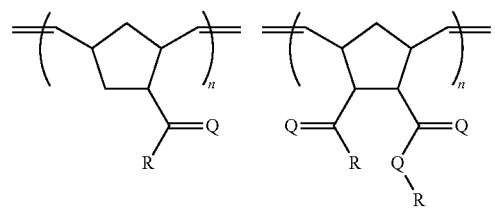

-continued

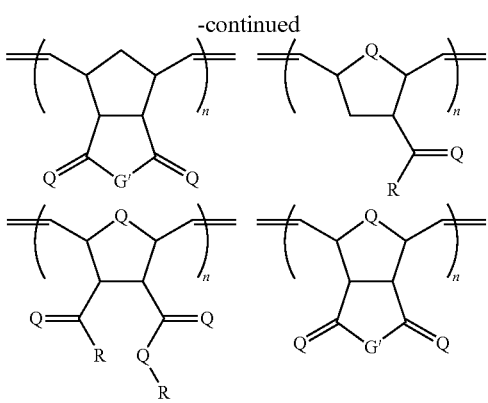

wherein:
Q is independently selected from among O, S, Se, or NH;
G' is each independently selected from among the following structures:

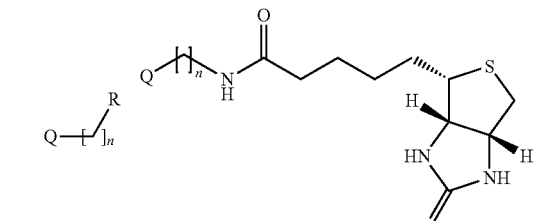

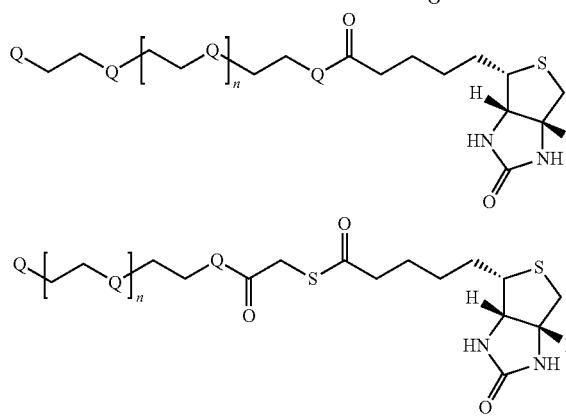

R is selected from among a hydrogen, straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or R is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or R is selected from among a photocrosslinkable or ionically crosslinkable group;

n is independently selected from an integer of 1-1000;

each polymeric terminal group is selected from among amines, thiols, amides, phosphates, sulphates, hydroxides, metals, alkanes, alkenes and alkynes.

45. The method of any of paragraphs 35-44, wherein said oligomer or polymer is selected from the group consisting of

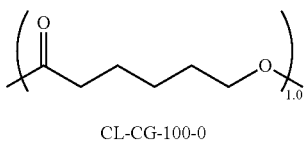

CL-CG-100-0

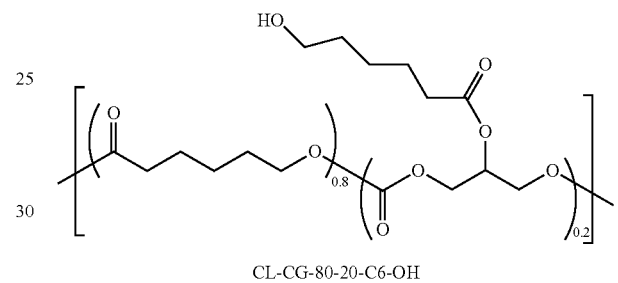

CL-CG-80-20-C6-OH

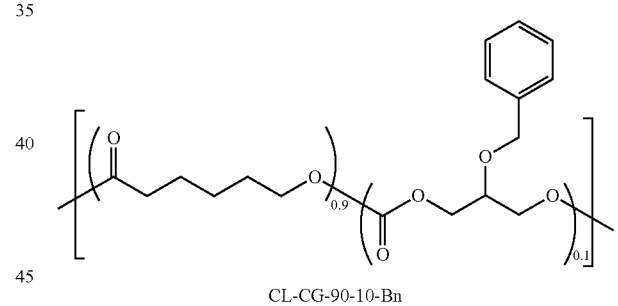

CL-CG-90-10-Bn

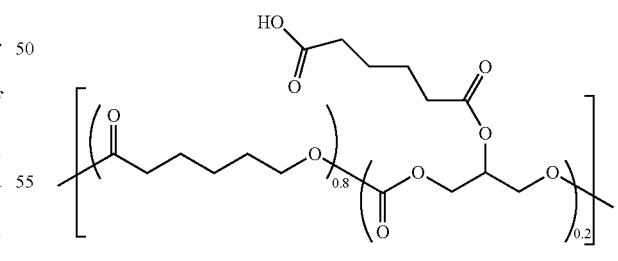

CL-CG-80-20-C5-COOH

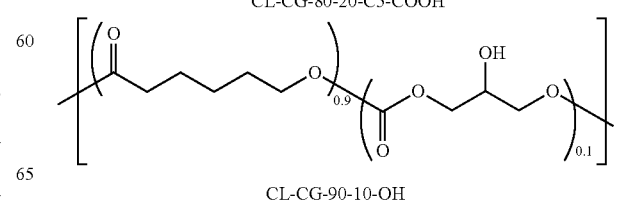

CL-CG-90-10-OH

-continued

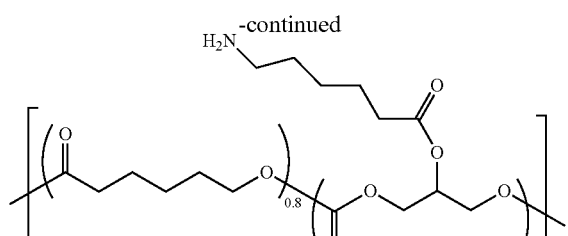

CL-CG-80-20-C6-NH2

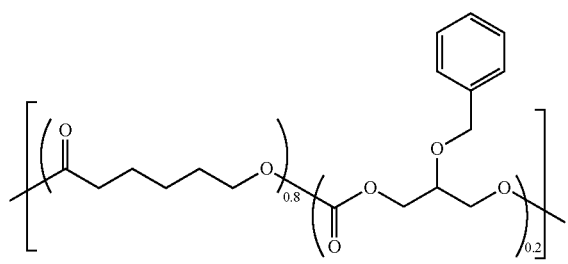

CL-CG-80-20-Bn

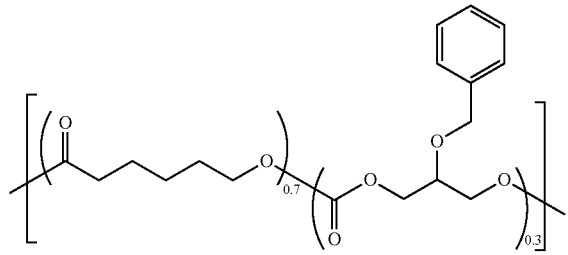

CL-CG-70-30-Bn

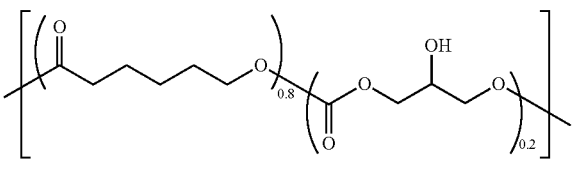

CL-CG-80-20-OH

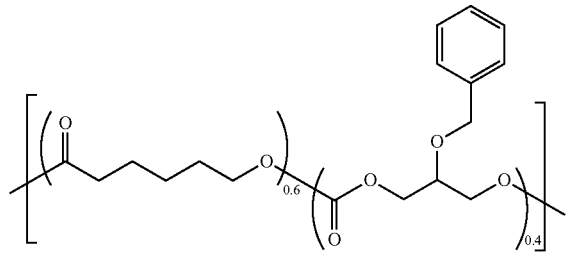

CL-CG-60-40-Bn

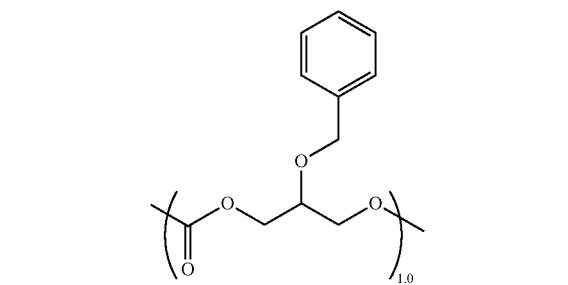

CL-CG-0-100-Bn and any combinations thereof.

46. A method for characterizing or identifying an analyte comprising:
(i) receiving the analyte through a nanopore of an article of any of paragraphs 1-34; and
(ii) detecting variation in current flow through the nanopore, wherein the variation in current correspond to translocation of the analyte through the nanopore, thereby characterizing or identifying the analyte.

47. The method of paragraph 46, wherein analyte is a biopolymer.

48. The method of paragraph 46 or 47, wherein the biopolymer is a nucleic acid or a protein.

49. The method of any of paragraphs 46-48, wherein said detecting variations in current flow comprises detecting an open nanopore current and a blocked nanopore current, the blocked nanopore current varying with respect to analyte translocation through the nanopore.

50. The method of any of paragraphs 46-49, wherein said analyte is a biopolymer and the blocked nanopore current varies with respect to length of the biopolymer.

51. The method of any of paragraphs 46-50, wherein analyte comprises a biopolymer and the blocked nanopore current varies with respect to sequence of the biopolymer.

52. The method of any of paragraphs 46-51, wherein said analyte is bound to a target binding moiety and the blocked nanopore current varies with respect to interactions between the analyte and the target binding moiety.

53. The method of any of paragraphs 46-52, wherein said analyte is bound to a capture probe and the blocked nanopore current varies with respect to interactions between the analyte and the capture probe.

54. The method of any of paragraphs 35-53, wherein the analyte is a nucleic acid and the blocked nanopore current varies with respect to nucleic acid being single-stranded versus being double-stranded.

55. The method of any of paragraphs 46-54, wherein said characterization or identifying comprises: (i) sequencing a nucleic acid; (ii) detecting a nucleic acid sequence; (iii) detecting a protein; (iv) detecting protein to nucleic acid interaction(s); (v) detecting protein to protein interaction(s); (vi) detecting nucleic acid to nucleic acid interaction(s); (vii) determining length of a nucleic acid sequence; (viii) determining the length of an amino acid sequence for proteomic analysis; or (ix) any combinations of (i)-(viii).

56. A method for identifying a nucleic acid sequence comprising:
(i) exposing an article of any of paragraphs 1-34 to a solution comprising the nucleic acid of interest, wherein the 3D porous coating comprises a nucleic acid binding moiety;
(ii) allowing the nucleic acid of interest to bind with the nucleic acid binding moiety;
(iii) optionally washing any unbound nucleic acid of interest;
(iv) releasing the nucleic acid and the nucleic acid binding moiety as a complex from the 3D porous coating; and
(v) detecting variation in current flow through the nanopore, wherein the variation in current corresponding to translocation of the nucleic acid bound to the nucleic acid binding moiety through the nanopore is different from variation in current corresponding to translocation of unbound the nucleic acid or the nucleic acid binding moiety alone, thereby identifying the nucleic acid sequence.
57. A method for identifying a nucleic acid sequence comprising:
  (i) exposing an article of any of paragraphs 1-34 to a solution comprising the nucleic acid of interest, wherein the 3D porous coating comprises a nucleic acid binding moiety;
  (ii) allowing the nucleic acid of interest to bind with the nucleic acid binding moiety;
  (iii) optionally washing any unbound nucleic acid of interest;
  (iv) releasing the nucleic acid from the nucleic acid binding moiety; and
  (v) detecting variation in current flow through the nanopore, wherein the variation in current corresponding to translocation of the released nucleic acid through the nanopore is different from variation in current corresponding to translocation of the nucleic acid bound with the nucleic acid binding moiety or the nucleic acid binding moiety alone, thereby identifying the nucleic acid sequence.
58. A method for identifying a nucleic acid sequence comprising:
  (i) obtaining a nucleic acid/capture probe complex, wherein the capture probe is a nucleic acid binding moiety;
  (ii) exposing an article of any of paragraphs 1-34 to a solution comprising the nucleic acid/capture probe complex;
  (iii) allowing the capture probe in the complex to bind with the 3D porous coating;
  (iv) optionally washing any unbound nucleic acid/capture probe complex;
  (v) releasing the nucleic acid from the 3D porous coating bound nucleic acid/capture probe complex; and
  (vi) detecting variation in current flow through the nanopore, wherein the variation in current flow correspond to translocation of the nucleic acid through the nanopore, thereby identifying the nucleic acid sequence.
59. The method of any of paragraphs 46-58, wherein the 3D porous coating comprises two or more different target binding moieties and each different target binding moiety capturing a different analyte, thereby allowing multiplex characterization of two or more analytes.
60. The method of any of paragraphs 46-59, wherein the 3D porous coating comprises two or more different target binding moieties, each different target binding moiety capturing a different analyte, and said different captured analytes being released sequentially, thereby allowing multiplex characterization of said analytes.
61. A method for determining the length of a nucleic acid sequence comprising:
  (i) exposing an article of any of paragraphs 1-34 to a solution comprising the nucleic acid; and
  (ii) detecting variation in current flow through the nanopore, wherein the variation in current corresponds to translocation of the nucleic acid through the nanopore and time of translocation corresponds to length of the nucleic acid.
62. A method for identifying a protein comprising:
  (i) exposing an article of any of paragraphs 1-34 to a solution comprising the protein of interest, wherein the 3D porous coating comprises a protein binding moiety;
  (ii) allowing the protein of interest to bind with the protein binding moiety;
  (iii) optionally washing any unbound protein of interest;
  (iv) releasing the protein and the protein binding moiety as a complex from the 3D porous coating; and
  (v) detecting variation in current flow through the nanopore, wherein the variation in current corresponding to translocation of the protein bound to the protein binding moiety through the nanopore is different from variation in current corresponding to translocation of unbound protein or the protein binding moiety alone, thereby identifying the protein.
63. A method for identifying a protein comprising:
  (i) exposing an article of any of paragraphs 1-34 to a solution comprising the protein of interest, wherein the 3D porous coating comprises a protein binding moiety;
  (ii) allowing the protein of interest to bind with the protein binding moiety;
  (iii) optionally washing any unbound protein of interest;
  (iv) releasing the protein from the protein binding moiety; and
  (v) detecting variation in current flow through the nanopore, wherein the variation in current corresponding to translocation of the protein through the nanopore is different from variation in current corresponding to translocation of protein bound to the protein binding moiety or the protein binding moiety alone, thereby identifying the protein.
64. A method for identifying or characterizing an analyte comprising:
  (i) exposing an article of any of paragraphs 1-34 to a solution comprising a molecule comprising a first target binding moiety, wherein the 3D porous coating comprises a second target binding moiety, wherein the second target binding moiety binds to the molecule comprising the first target binding moiety;
  (ii) allowing the molecule comprising the first target binding moiety to bind with the second target binding moiety;
  (iii) optionally blocking any free target binding sites on the second binding moiety;
  (iv) exposing the article from step (iii) to a solution comprising the analyte of interest;
  (v) allowing the analyte to bind to the first target binding moiety;
  (vi) optionally washing out any unbound analyte;
  (vii) exposing the article from step (v) to a solution comprising a molecule comprising a third target binding moiety, wherein the third target binding moiety binds to the bound analyte;
  (viii) allowing the molecule comprising the third target binding moiety to the analyte;
  (ix) optionally washing out any unbound molecule comprising the third binding moiety;
  (x) exposing the article from step (viii) to a solution a reporter molecule, wherein the reporter molecule binds to the molecule comprising the third target binding moiety;
  (xi) allowing the reporter molecule to bind to the molecule comprising the third target binding moiety;
  (xii) optionally washing out any unbound reporter molecule;

(xiii) releasing the reporter molecule from the third target binding moiety;
(xiv) exposing the article from step (xiii) to a voltage potential, thereby drawing the reporter molecule through the nanopore and allowing for single molecule detection of the reporter molecule if the analyte of interest was captured by the 3D coating.

65. A method for determining the concentration of a scale inhibitor in an oil sample comprising:
    (i) exposing an article of any of paragraphs 1-34 to a sample comprising a scale inhibitor obtained from an oil well; and
    (ii) detecting variation in current flow through the nanopore, wherein the variation in current corresponding to translocation of the scale inhibitor through the nanopore.

66. The method of paragraph 65, further comprising isolating the scale inhibitor before exposing to the article.

67. The method of paragraph 65 or 66, wherein the scale inhibitor is a polyelectrolyte.

68. The method of any of paragraphs 65-67, wherein the scale inhibitor is polyacrylic acid.

69. A method for detecting or identifying an anionic polyelectrolyte in a sample comprising:
    (i) exposing an article of any of paragraphs 1-34 to a sample comprising the anionic polyelectrolyte, wherein the 3D porous coating is positively charged;
    (ii) allowing the anionic polyelectrolyte to bind to the positively charged 3D porous coating;
    (iii) optionally washing any unbound anionic polyelectrolyte;
    (iv) releasing the bound anionic polyelectrolyte from the 3D porous coating;
    (v) detecting variation in current flow through the nanopore, wherein the variation in current corresponding to translocation of the anionic polyelectrolyte through the nanopore.

70. The method of paragraph 69, wherein said releasing of the bound anionic polyelectrolyte is by changing the pH in the 3D porous coating.

71. The method of paragraph 69 or 70, wherein polyelectrolyte is polyacrylic acid (PAA)

72. The method of any of paragraphs 46-71, wherein said solution is an aqueous solution.

73. Use of an article of any of paragraphs 1-34 to sequence nucleic acid.

74. Use of an article of any of paragraphs 1-34 to sequence proteins.

75. Use of an article of any of paragraphs 1-34 to detect a nucleic acid sequence.

76. Use of an article of any of paragraphs 1-34 to detect a protein.

77. Use of an article of any of paragraphs 1-34 to detect protein to nucleic acid interaction(s).

78. Use of an article of any of paragraphs 1-34 to detect protein to protein interaction(s).

79. Use of an article of any of paragraphs 1-34 to detect nucleic acid to nucleic acid interaction(s).

80. Use of an article of any of paragraphs 1-34 to determine the length of a nucleic acid.

81. The use of paragraph 80, wherein said determination of the length is for genomic or transcriptomic analysis.

82. Use of an article of any of paragraphs 1-34 to determine the length of a polypeptide.

83. The use of paragraph 79, wherein said determination of the length is for proteomic analysis.

84. Use of an article of any of paragraphs 1-34 for detection of a polyelectrolyte.

85. The use of paragraph 84, wherein the polyelectrolyte is a synthetic polyelectrolyte.

86. The use of paragraph 84 or 85, wherein the polyelectrolyte is manmade.

87. The use of an article of any of paragraphs 1-34 for detection of a polyelectrolyte, wherein the polyelectrolyte has been added to an oil well, pipe or system for extracting oil from a reservoir.

88. The use of paragraph 87, wherein the polyelectrolyte is a synthetic polyelectrolyte.

89. The use of paragraphs 87 or 88, wherein the polyelectrolyte is a non-natural polyelectrolyte.

Additional embodiments of the various aspects disclosed herein can also be described by one or more of the following numbered paragraphs:

1. A 3D porous coated membrane or thin solid-state, polymeric, lipid, or solid-like film containing nanopore composition comprising: a) nanopore(s) and 2) a 3D porous coating(s).
2. A composition of paragraph 1 wherein the coating is a fiber such as an electrospun polymer.
3. A composition of paragraph 1 wherein the coating is a gel or hydrogel such as a collagen gel or polyacrylamide gel.
4. A composition of paragraph 1 wherein the coating is assembled spheres such as an electrosprayed polymer.
5. A 3D porous coated nanopore composition of paragraphs 1-5 comprising: a) nanopore(s) and 2) a coating(s) where in the coating contains a targeting moiety for nucleic acid such dsDNA, ssDNA, RNA, mRNA, or miRNA.
6. A 3D porous coated nanopore composition of paragraphs 1-5 comprising: a) nanopore(s) and 2) a coating(s) where in the coating contains a targeting moiety for a protein such as hemoglobin, insulin, antibody, or enzyme.
7. A 3D porous coated nanopore composition of paragraphs 1-5 comprising: a) nanopore(s) and 2) a coating(s) where in the coating contains a denaturation agent such a guanidinium chloride, urea, trichloroacetic acid, or sulfosalicylic acid that is non-covalently or covalently bound to the coating.
8. A 3D porous coated nanopore composition comprising: a) nanopore(s) and 2) one or more coatings.
9. Use of the composition of paragraphs 1 or 8 to sequence nucleic acid.
10. Use of the composition of paragraphs 1 or 8 to sequence proteins.
11. Use of the composition of paragraphs 1 or 8 to detect a nucleic acid sequence.
12. Use of the composition of paragraphs 1 or 8 to detect a protein.
13. Use of the composition of paragraphs 1 or 8 to detect a protein to nucleic acid interaction (s)
14. Use of the composition of paragraphs 1 or 8 to detect a protein to protein interaction (s)
15. Use of the composition of paragraphs 1 or 8 to detect a nucleic acid to nucleic acid interaction (s)
16. Use of the composition of paragraphs 1 or 8 to determine the length of a nucleic acid sequence for genomic or transcriptomic analysis for DNA or RNA, respectively.
17. Use of the composition of paragraphs 1 or 8 to determine the length of an amino acid sequence for proteomic analysis.

18. A method of making a 3-dimensional coated nanopore composition of paragraphs 1-5, the method comprising the steps of:
   (a) preparing the bare nanopore(s) structure,
   (b) electrospinning, electrospraying or ultrasonic spraying a polymer on either or both sides of the nanopore(s), thereby forming the 3-dimensional composition near or on the surface of the nanopore.
19. A method of making a 3-dimensional coated nanopore composition, the method comprising the steps of:
   (a) preparing the bare nanopore structure,
   (b) gelling or crosslinking one or more polymers above the nanopore via mixing, heat, light, or chemical induction on either or both sides of the nanopore(s) thereby forming the 3-dimensional gel composition near or on the surface of the nanopore.
20. A coating of the above paragraphs where in the polymer is a linear, comb, branched, or dendritic oligomer or polymer represented by one of the following formulas:

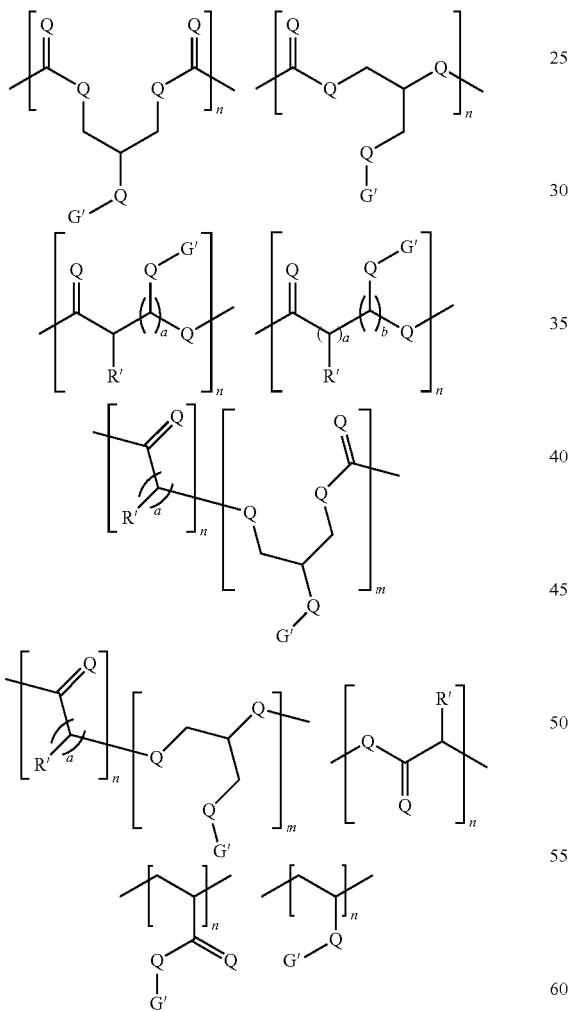

wherein:
Q' is independently selected from among O, S, Se, or NH;
G' is each independently selected from among the following structures:

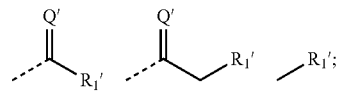

wherein G'$_1$ and G'$_2$ are not the same;
R'$_1$ is selected from among a hydrogen, straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or
R'$_1$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or
R'$_1$ is selected from among a photocrosslinkable or ionically crosslinkable group;
R'$_2$ is selected from among hydrogen, a straight or branched alkyl, cycloalkyl, aryl, olefin, silyl, alkylsilyl, arylsilyl, alkylaryl, fluorocarbon, or arylalkyl chain of 1-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;
m, n, a, or b are each independently selected from an integer of 1-1000;
each polymeric terminal group is selected from among amines, thiols, amides, phosphates, sulphates, hydroxides, metals, alkanes, alkenes and alkynes.
21. A coating of the above paragraphs where in the polymer is a linear, comb, branched, or dendritic oligomer or polymer has a alcohol, acid, amine, azide, alkyne, alkene, NHS, MAL, or other such groups so that a targeting moiety to capture a biologic can be attached.
22. A method of identifying a nucleic acid sequence using a coated nanopore composition, the method comprising the steps of:
   (a) preparing the 3D coated nanopore with the target sequence incorporated within,
   (b) exposing said 3D coated nanopore to an aqueous solution containing the analyte (nucleic acid or protein) of interest
   (c) the analyte binds to the target strand and the 3D coated nanopore is washed to remove unbound nucleic acid and other biologics
   (d) the 3D coated nanopore is exposed to pH, a thiol containing molecule, heat, or chemical treatment such that the target & analyte nucleic acid are released as double strand,
   (e) the double strand nucleic acid containing the analyte of interest is detected via translocation through the NP. The target strand released, not containing the captured analyte, is discernable from the target/capture analyte duplex via NP sensing.

23. A method of identifying a nucleic acid sequence using a coated nanopore composition, the method comprising the steps of:
    (a) preparing the 3D coated nanopore with the target sequence incorporated within,
    (b) exposing said 3D coated nanopore to an aqueous solution containing the analyte (nucleic acid or protein) of interest
    (c) the analyte binds to the target strand and the 3D coated nanopore is washed to remove unbound nucleic acid and other biologics
    (d) the 3D coated nanopore is exposed to pH, a change in ionic strength, heat, or chemical treatment such that the captured analyte nucleic acid is released,
    (e) the captured analyte nucleic acid is detected via translocation through the NP.

24. A method of identifying a nucleic acid sequence using a coated nanopore composition, the method comprising the steps of:
    (a) prepare an aqueous solution containing the analyte and single-stranded oligonucleotide capture probe and anneal the capture probe to the target sequence, then
    (b) prepare the 3D coated nanopore with primed functionality to bind the capture probe within,
    (c) exposing said 3D coated nanopore to an aqueous solution containing the hybridized probe and target sequences where
    (d) the capture probe binds to 3D coating and the 3D coated nanopore is washed to remove unbound nucleic acid and other biologics
    (e) the 3D coated nanopore is exposed to pH, a change in ionic strength, heat, or chemical treatment such that the captured analyte nucleic acid is released,
    (f) the captured analyte nucleic acid is detected via translocation through the NP.

25. A method of identifying a nucleic acid sequence using a coated nanopore composition, the method comprising the paragraphs 22-24 wherein more than one capture probe is on the coating allowing for multiplex sensing.

26. A method of identifying a nucleic acid sequence using a coated nanopore composition, the method comprising the paragraphs 22-24 wherein more than one capture probe is on the coating allowing for multiplex sensing wherein the each targeted analyte is released sequentially for detection and identification.

27. A method of sizing the length of a nucleic acid sequence using a coated nanopore composition, the method comprising the steps of:
    (a) preparing the 3D coated nanopore,
    (b) exposing said 3D coated nanopore to an aqueous solution containing the analyte (ds-nucleic acid or ss-nucleic acid) of interest
    (c) the nucleic acid is detected via translocation through the NP and the time of translocation is related to the length of the nucleic acid.

28. A method of identifying a protein using a coated nanopore composition, the method comprising the steps of:
    (a) preparing the 3D coated nanopore with the protein target probe incorporated within,
    (b) exposing said 3D coated nanopore to an aqueous solution containing the analyte (protein) of interest
    (c) the analyte binds to the protein target probe and the 3D coated nanopore is washed to remove unbound protein and other biologics
    (d) the 3D coated nanopore is exposed to pH, a thiol containing molecule, heat, or chemical treatment such that the target and/or analyte protein are released,
    (e) the analyte of interest is detected via translocation through the NP. The target probe released, not containing the captured analyte, is discernable from the target/capture analyte duplex via NP sensing.

29. A method of identifying a target protein using a coated nanopore composition, the method comprising the steps of:
    (a) preparing the 3D coated nanopore with bio-recognition sites (e.g. Avidin),
    (b) exposing said 3D coated nanopore to an aqueous solution containing a molecule that binds the bio-recognition site in step (a) (e.g. biotin) which tethers the mesh to a second bio-recognition site (e.g. antibody, aptamer, etc.) specific for the analyte (protein) of interest (e.g. Biotinylated antibody)
    (c) expose said 3D coated nanopore to an aqueous solution which saturates the bio-recognition sites from step (a) (e.g. excess free biotin).
    (d) expose said 3D coated nanopore to an aqueous solution of the analyte (e.g. protein) of interest allowing the analyte to bind to the second bio-recognition site from step (b)
    (e) the 3D coated nanopore is washed to remove unbound protein, other biologics, and any unbound molecules
    (f) the 3D coated nanopore is exposed to an aqueous solution of a third bio-recognition site specific for the analyte of interest which is tethered to a stimuli responsive (heat, chemical, light, etc.) release unit capable of binding a reporter molecule (e.g. avidin) detectable in a nanopore
    (g) the 3D coated nanopore is washed to remove unbound protein, other biologics, and any unbound molecules
    (h) the 3D coated nanopore is exposed to an aqueous solution of the reporter molecule (e.g. avidin), in excess, which binds the tether (e.g. biotin) of the bio-recognition site in step (f)
    (i) the 3D coated nanopore is washed to remove unbound protein, other biologics, and any unbound molecules
    (j) the 3D coated nanopore is exposed to the release stimulus from step (f) releasing the reporter molecule (e.g. avidin) into solution
    (k) the 3D coated nanopore is exposed to a voltage potential drawing the reporter molecule through the pore allowing for single molecule detection of the reporter molecule (e.g. avidin) only if the analyte of interest was captured by the 3D coating 30. A coating of the above claims where in the polymer is a linear, comb, branched, or dendritic oligomer or polymer represented by one of the following formulas:

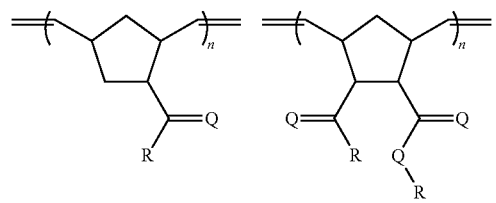

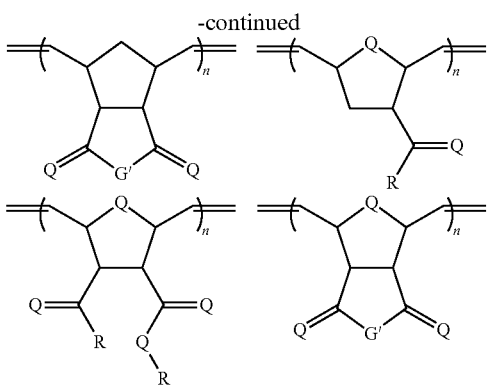

wherein:
Q' is independently selected from among O, S, Se, or NH;
G' is each independently selected from among the following structures:

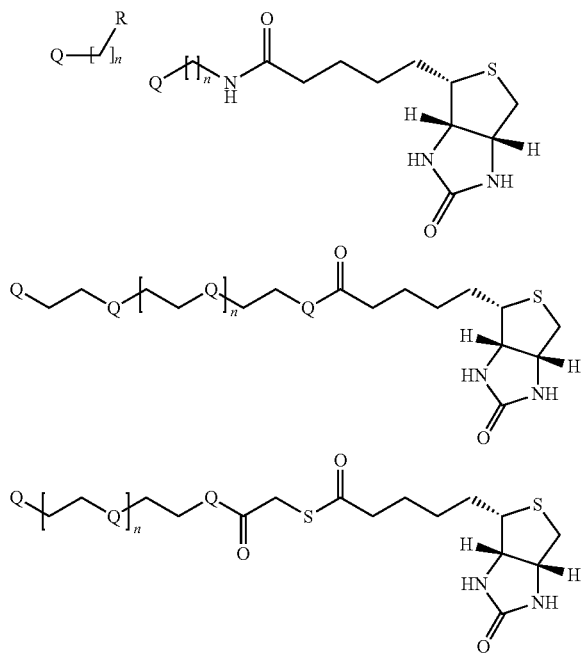

R'$_1$ is selected from among a hydrogen, straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or
R'$_1$ is selected from among poly(ethylene glycol), poly(ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or
R'$_1$ is selected from among a photocrosslinkable or ionically crosslinkable group;

R'$_2$ is selected from among hydrogen, a straight or branched alkyl, cycloalkyl, aryl, olefin, silyl, alkylsilyl, arylsilyl, alkylaryl, fluorocarbon, or arylalkyl chain of 1-50 carbons, wherein each alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;
m, n, a, or b are each independently selected from an integer of 1-1000;
each polymeric terminal group is selected from among amines, thiols, amides, phosphates, sulphates, hydroxides, metals, alkanes, alkenes and alkynes.

Selected Definitions

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular. Thus, as used herein and in the claims, the singular forms include the plural reference and vice versa unless the context clearly indicates otherwise.

As used herein the term "comprising" or "comprises" is used in reference to compositions, methods, and respective component(s) thereof, that are useful to an embodiment, yet open to the inclusion of unspecified elements, whether useful or not. The use of "comprising" indicates inclusion rather than limitation. Accordingly, the terms "comprising" means "including principally, but not necessary solely". Furthermore, variation of the word "comprising", such as "comprise" and "comprises", have correspondingly the same meanings. The term "consisting essentially of" means "including principally, but not necessary solely at least one", and as such, is intended to mean a "selection of one or more, and in any combination". Stated another way, the term "consisting essentially of" means that an element can be added, subtracted or substituted without materially affecting the novel characteristics of the invention. This applies equally to steps within a described method as well as compositions and components therein.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages can mean 5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviations (2SD) away from a reference level. The term refers to statistical evidence that there is a difference. It is defined as the probability of making a decision to reject the null hypothesis when the null hypothesis is actually true.

As used interchangeably herein, the terms "essentially" and "substantially" means a proportion of at least about 60%, or preferably at least about 70% or at least about 80%, or at least about 90%, at least about 95%, at least about 97% or at least about 99% or more, or any integer between 70% and 100%. In some embodiments, the term "essentially" means a proportion of at least about 90%, at least about 95%, at least about 98%, at least about 99% or more, or any integer between 90% and 100%. In some embodiments, the term "essentially" can include 100%.

In general, the term "aliphatic", as used herein, includes both saturated and unsaturated, straight chain (i.e., unbranched) or branched aliphatic hydrocarbons, which are optionally substituted with one or more functional groups, as defined below. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having 1-6 carbon atoms. In certain embodiments, the alkyl, alkenyl and alkynyl groups employed in the invention contain 1-20 aliphatic carbon atoms. In certain other embodiments, the alkyl, alkenyl, and alkynyl groups employed in the invention contain 1-10 aliphatic carbon atoms. In yet other embodiments, the alkyl, alkenyl, and alkynyl groups employed in the invention contain 1-8 aliphatic carbon atoms. In still other embodiments, the alkyl, alkenyl, and alkynyl groups employed in the invention contain 1-6 aliphatic carbon atoms. In yet other embodiments, the alkyl, alkenyl, and alkynyl groups employed in the invention contain 1-4 carbon atoms.

Illustrative aliphatic groups thus include, but are not limited to, for example, methyl, ethyl, n-propyl, isopropyl, allyl, n-butyl, sec-butyl, isobutyl, tert-butyl, n-pentyl; sec-pentyl, isopentyl, tert-pentyl, n-hexyl, sec-hexyl, moieties and the like, which again, may bear one or more substituents, as previously defined. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The term "alicyclic", as used herein, refers to compounds which combine the properties of aliphatic and cyclic compounds and include but are not limited to cyclic, or polycyclic aliphatic hydrocarbons and bridged cycloalkyl compounds, which are optionally substituted with one or more functional groups, as defined below. As will be appreciated by one of ordinary skill in the art, "alicyclic" is intended herein to include, but is not limited to, cycloalkyl, cycloalkenyl, and cycloalkynyl moieties, which are optionally substituted with one or more functional groups. Illustrative alicyclic groups thus include, but are not limited to, for example, cyclopropyl, —$CH_2$-cyclopropyl, cyclobutyl, —$CH_2$-cyclobutyl, cyclopentyl, —$CH_2$-cyclopentyl-n, cyclohexyl, —$CH_2$-cyclohexyl, cyclohexenylethyl, cyclohexanylethyl, norborbyl moieties and the like, which again, may bear one or more substituents.

The term "heteroaliphatic", as used herein, refers to aliphatic moieties in which one or more carbon atoms in the main chain have been substituted with an heteroatom. Thus, a heteroaliphatic group refers to an aliphatic chain which contains one or more oxygen sulfur, nitrogen, phosphorus or silicon atoms, e.g., in place of carbon atoms. Heteroaliphatic moieties may be saturated or unsaturated, branched or linear (i.e., unbranched), and substituted or unsubstituted. Substituents include, but are not limited to, any of the substituents mentioned below, i.e., the substituents recited below resulting in the formation of a stable compound.

The term "heteroalicyclic", as used herein, refers to compounds which combine the properties of heteroaliphatic and the cyclic compounds and include but are not limited to saturated and unsaturated mono- or polycyclic heterocycles such as morpholino, pyrrolidinyl, furanyl, thiofuranyl, pyrrolyl, etc, which are optionally substituted with one or more functional groups. Substituents include, but are not limited to, any of the substituents mentioned below, i.e., the substituents recited below resulting in the formation of a stable compound.

The term "alkyl", as used herein, refers to saturated, straight- or branched-chain hydrocarbon radicals derived from a hydrocarbon moiety containing between one and twenty carbon atoms by removal of a single hydrogen atom, which alkyl groups are optionally substituted with one or more functional groups. Substituents include, but are not limited to, any of the substituents mentioned below, i.e., the substituents recited below resulting in the formation of a stable compound. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl.

The term "alkoxy", as used herein, refers to an alkyl group, as previously defined, attached to the parent molecular moiety through an oxygen atom. Examples include, but are not limited to, methoxy, ethoxy, propoxy, isopropoxy, n-butoxy, tert-butoxy, neopentoxy, and n-hexoxy.

The term "alkenyl" denotes a monovalent group derived from a hydrocarbon moiety having at least one carbon-carbon double bond, which alkenyl group is optionally is substituted with one or more functional groups. In certain embodiments, an alkenyl group contains between one and twenty carbon atoms. Substituents include, but are not limited to, any of the substituents mentioned below, i.e., the substituents recited below resulting in the formation of a stable compound. Alkenyl groups include, for example, ethenyl, propenyl, butenyl, 1-methyl-2-buten-1-yl, and the like. The term "alkynyl", as used herein, refers to a monovalent group derived from a hydrocarbon having at least one carbon-carbon triple bond, which alkynyl group is optionally substituted. In certain embodiments, an alkynyl group contains between one and twenty carbon atoms. Substituents include, but are not limited to, any of the substituents mentioned below, i.e., the substituents recited below resulting in the formation of a stable compound. Representative alkynyl groups include ethynyl, 2-propynyl (propargyl), 1-propynyl, and the like. The term "amine", as used herein, refers to one, two, or three alkyl groups, as previously defined, attached to the parent molecular moiety through a nitrogen atom. The term "alkylamino" refers to a group having the structure —NHR' wherein R' is an alkyl group, as previously defined; and the term "dialkylamino" refers to a group having the structure —NR'R", wherein R' and R" are each independently selected from the group consisting of alkyl groups. The term "trialkylamino" refers to a group having the structure —NR'R"R'", wherein R', R", and R'" are each independently selected from the group consisting of alkyl groups. Additionally, R', R", and/or R'" taken together may optionally be —(CH$_2$).sub.k—where k is an integer from 2 to 6. Examples of amino groups include, but are not limited to, methylamino, dimethylamino, ethylamino, diethylamino, diethylaminocarbonyl, methylethylamino, iso-propylamino, piperidino, trimethylamino, and propylamino.

The term "aryl", as used herein, refers to stable mono- or polycyclic, unsaturated moieties having preferably 3-14 carbon atoms, each of which may be substituted or unsubstituted. Substituents include, but are not limited to, any of the substituents mentioned below, i.e., the substituents recited below resulting in the formation of a stable compound. The term aryl may refer to a mono- or bicyclic carbocyclic ring system having one or two aromatic rings including, but not limited to, phenyl, naphthyl, tetrahydronaphthyl, indanyl, indenyl and the like.

The term "heteroaryl", as used herein refers to a stable heterocyclic or polyheterocyclic, unsaturated radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms. Heteroaryl moieties may be substituted or unsubstituted. Substituents include, but are not limited to, any of the substituents mentioned below, i.e., the substituents recited below resulting in the formation of a stable compound. Examples of heteroaryl nuclei include pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will also be appreciated that aryl and heteroaryl moieties, as defined herein, may be attached via an aliphatic, alicyclic, heteroaliphatic, heteroalicyclic, alkyl or heteroalkyl moiety and thus also include -aliphatic)aryl, -(heteroaliphatic)aryl, -(aliphatic)heteroaryl, -(heteroaliphatic)heteroaryl, -alkyl)aryl, -(heteroalkyl)aryl, -(heteroalkyl)aryl, and -heteroalkyl)-heteroaryl moieties. Thus, as used herein, the phrases "aryl or heteroaryl" and "aryl, heteroaryl, -(aliphatic)aryl, -(heteroaliphatic)aryl, -(aliphatic)heteroaryl, -(heteroaliphatic)heteroaryl, -(alkyl)aryl, -(heteroalkyl)aryl, -(heteroalkyl)aryl, and -(heteroalkyl)heteroaryl" are interchangeable.

The term "carboxylic acid", as used herein, refers to a group of formula —CO$_2$H.

The terms "halo", "halide", and "halogen", as used herein, refers to an atom selected from fluorine, chlorine, bromine, and iodine.

The term "methylol", as used herein, refers to an alcohol group of structure —CH$_2$OH.

The term "hydroxyalkyl" refers to an alkyl group, as defined above, bearing at least one OH group.

The term "mercaptoalkyl", a used herein, refers to an alkyl group, as defined above, bearing at least one SH group.

The term "heterocyclic", as used herein, refers to a non-aromatic partially unsaturated or fully saturated 3- to 10-membered ring system, which includes single rings of 3 to 8 atoms in size and bi- and tri-cyclic ring systems which may include aromatic six-membered aryl or aromatic heterocyclic groups fused to a non-aromatic ring. Heterocyclic moieties may be substituted or unsubstituted. Substituents include, but are not limited to, any of the substituents mentioned below, i.e., the substituents recited below resulting in the formation of a stable compound. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized.

The term "acyl", as used herein, refers to a group comprising a carbonyl group of the formula C=O. Examples of acyl groups include aldehydes, ketones, carboxylic acids, acyl halides, anhydrides, thioesters, amides, urea, carbamate, and carboxylic esters.

The term "hydrocarbon", as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, and the like. As would be known to one skilled in this art, all valencies must be satisfied in making any substitutions. Likewise, the term "fluorocarbon", as used herein, refers to any chemical group comprising more fluorine atoms than hydrogen atoms attached to carbons. The fluorocarbon may be substituted or unsubstituted. A fluorocarbon may be saturated, unsaturated, branched, unbranched, cyclic, polycyclic or heterocyclic.

The term "substituted", whether preceded by the term "optionally" or not, refers to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Examples of substituents include, but are not limited to aliphatic; alicyclic; heteroaliphatic; heteroalicyclic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —NCO; —CF$_3$; —CH$_2$CF$_3$; —CHCl$_2$; —CH$_2$OR$_x$; —CH$_2$CH$_2$OR.sub.x; —CH$_2$N(R$_x$)$_2$; —CH$_2$SO$_2$CH$_3$; —C(O)R$_x$; —CO$_2$(R$_x$); —CON(R$_x$)$_{-2}$; —OC(O)R$_x$; —C(O)OC(O)R$_x$; —OCO$_2$R$_x$; —OCON(R$_x$)$_2$; —N(R$_x$)$_2$; —S(O)$_2$R$_x$; OCO$_2$R$_x$; —NR$_x$(CO)R$_x$; —NR$_x$(CO)N(R$_x$)$_2$, wherein each occurrence of R.sub.x independently includes, but is not limited to, H, aliphatic, alicyclic, heteroaliphatic, heteroalicyclic, aryl, heteroaryl, alkylaryl, or alkylheteroaryl, wherein any of the aliphatic, alicyclic, heteroaliphatic, heteroalicyclic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

As used herein, the term "nucleic acid" or "oligonucleotide" or "polynucleotide" refers to a polymer or an oligomer of nucleotide or nucleoside monomers consisting of nucleobases, sugars and intersugar linkages. The term "oligonucleotide" also includes polymers or oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

The nucleic acids can be single-stranded or double-stranded. A single-stranded nucleic acid can have double-stranded regions and a double-stranded nucleic acid can have single-stranded regions. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe that can hybridize to the target sequence under stringent hybridization conditions. Thus, a nucleic acid also encompasses a probe that hybridizes under stringent hybridization conditions.

The nucleic acids can comprise any oligonucleotide modification known in the art. In some embodiments, the modification is selected from the group consisting of sugar modification, non-phosphodiester inter-sugar (or internucleoside) linkages, backbone replacements, nucleobase modifications, and any combinations thereof.

Without limitations, the nucleic acid can comprise from 2 to thousands of nucleotides. In some embodiments, when the target binding moiety or the capture probe is a nucleic acid, the nucleic acid can range from about 6 to 100 nucleotides in length. In various related embodiments, the nucleic acid can range in length from about 10 to about 50 nucleotides, from about 10 to about 35 nucleotides, from about 15 to about 30 nucleotides, from about 20 to about 30 nucleotides in length. In some embodiments, nucleic acid is from about 8 to about 39 nucleotides in length. In some embodiments, the nucleic acid is 6 to 25 nucleotides in length (e.g., 6, 7, 8, 9, 10, 11, 12, 13, 14, 15, 16, 18, 19, 20, 21, 22, 23, or 24 nucleotides in length.

The nucleic acid can be completely DNA, completely RNA, or comprise both RNA and DNA nucleotides. It is to be understood that when the nucleic acid is completely DNA, RNA, or a mix of both, the nucleic acid can comprise one or more of the modifications described herein.

In some embodiments, the analyte is a nucleic acid and the target binding moiety or the capture probe is specifically hybridizable or complementary with the nucleic acid analyte. By "specifically hybridizable" and "complementary" is meant that a nucleic acid can form hydrogen bond(s) with another nucleic acid sequence by either traditional Watson-Crick or other non-traditional types. Determination of binding free energies for nucleic acid molecules, i.e., complementarity, is well known in the art (see, e.g., Turner et al, 1987, *CSH Symp. Quant. Biol. LII pp.* 123-133; Frier et al., 1986, *Proc. Nat. Acad. Sci. USA* 83:9373-9377; Turner et al., 1987, *I. Am. Chem. Soc.* 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands that are selected so as to be noncomplementary. Specific binding requires a sufficient degree of complementarity to avoid non-specific binding of the target binding moiety and or the capture probe to non-target analytes. The non-target analytes typically differ by at least two (e.g. two, three, four, five, six, seven, eight, nine, ten or more) nucleotides.

As used herein, the terms "proteins," "polypeptide" and "peptides" are used interchangeably herein to designate a series of amino acid residues connected to the other by peptide bonds between the alpha-amino and carboxy groups of adjacent residues. The terms "protein," "polypeptide" and "peptide", which are used interchangeably herein, refer to a polymer of protein amino acids, including modified amino acids (e.g., phosphorylated, glycated, etc.) and amino acid analogs, regardless of its size or function. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

As used herein, the term "antibody" or "antibodies" refers to an intact immunoglobulin or to a monoclonal or polyclonal antigen-binding fragment with the Fc (crystallizable fragment) region or FcRn binding fragment of the Fc region. The term "antibodies" also includes "antibody-like molecules", such as fragments of the antibodies, e.g., antigen-binding fragments. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies, and polypeptides that contain at least a portion of an immunoglobulin that is sufficient to confer specific antigen binding to the polypeptide. Linear antibodies are also included for the purposes described herein. The terms Fab, Fc, pFc', F(ab') 2 and Fv are employed with standard immunological meanings (Klein, Immunology (John Wiley, New York, N.Y., 1982); Clark, W. R. (1986) The Experimental Foundations of Modern Immunology (Wiley & Sons, Inc., New York); and Roitt, I. (1991) Essential Immunology, 7th Ed., (Blackwell Scientific Publications, Oxford)). Antibodies or antigen-binding fragments specific for various antigens are available commercially from vendors such as R&D Systems, BD Biosciences, e-Biosciences and Miltenyi, or can be raised against these cell-surface markers by methods known to those skilled in the art.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, publications, and websites identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Nanopores, pores of nanometer dimensions in an electrically insulating membrane, have shown promise for use in a variety of sensing applications, including single molecule detection. The nanopores used in such applications can be biological protein channels in a lipid bilayer or a pore in a solid-state membrane. Solid-state nanopores are generally made in silicon compound membranes, one of the most common being silicon nitride. Solid-state nanopores can be manufactured with several techniques including ion-beam sculpting of silicon nitride, and using electron-beam lithography and wet etching in crystalline silicon followed by oxidation.

The use of nanopores in single-molecule detection employs a detection principle based on monitoring the ionic current of an electrolyte solution passing through the nanopore as a voltage is applied across the membrane. When the nanopore is of molecular dimensions, passage of molecules causes interruptions in the open pore current level. The temporal variation in current levels leads to a translocation event pulse. These detection methods are described at length in: Kasianowicz J J, Brandin E, Branton D, Deamer D W (1996) Characterization of individual polynucleotide molecules using a membrane channel. Proc Nat Acad Sd 93: 13770-13773; Akeson, M, Branton, D, Kasianowicz J, Brandin E and Deamer D, (1999) Biophys. J. 77: 3227-3233; Meller A, Nivon L, Brandin E, Golovchenko J, Branton D, (2000) Proc Nat Acad Sci 97: 1079-1084, all of which are herein incorporated by reference in their entireties.

Nanopore detection techniques have been used for biomolecule detection. For example, various nanopore sequencing methods have been proposed. In 1994, Bezrukov, Vodyanoy and Parsegian showed that one can use a biological nanopore as a Coulter counter to count individual molecules (Counting polymers moving through a single ion channel, Nature 370, 279-281 (1994) incorporated, herein, by reference). In 1996, Kasianowicz, Brandin, Branton and Deamer proposed ultrafast single-molecule sequencing of single-stranded DNA molecules using nanopore ionic conductance as a sensing mechanism (Characterization of individual polynucleotide molecules using a membrane channel, Proc. Nat. Acad. Sci. USA 93 13770-13773 (1996), incorporated herein by reference). Since then, several groups have explored the α-hemolysin protein pore as a possible candidate for achieving this objective. (See, for example: Akeson, M, Branton, D, Kasianowicz J, Brandin E and Deamer D, (1999) Biophys. J. 77: 3227-3233; Meller A, Nivon L, Brandin E, Golovchenko J, Branton D, (2000) Proc Nat Acad Sci 97: 1079-1084; Braha, O.; Gu, L. Q.; Zhou, L.; Lu, X.; Cheley, S.; Bayley, H. Nat. Biotech. 2000; Meller A. Nivon L, and Branton, D. (2001) Phys. Rev. Left. 86:3435-3438; Meller A, and Branton D. (2002) Electrophoresis, 23:2583-2591; Bates M, Burns M, and Meller A (2003) Biophys. J. 84:2366-2372; Zwolak M, Di Ventra M (2007). Rev Mod Phys 80: 141-165, each of which is herein incorporated by reference in its entirety.) The methods seek to effectively determine the order in which nucleotides occur on a DNA strand (or RNA). The theory behind nanopore sequencing concerns observed behavior when the nanopore is immersed in a conducting fluid and a potential (voltage) is applied across it. Under these conditions an electrical current that results from the conduction of ions through the nanopore can be observed. The amount of current which flows is sensitive to the size of the nanopore. When a biomolecule passes through the nanopore, it will typically create a change in the magnitude of the current flowing through the nanopore. Electronic sensing techniques are used to detect the ion current variations, thereby sensing the presence of the individual biomolecules. U.S. Pat. No. 6,428,959, the entire contents of which are herein incorporated by reference, describes methods for determining the presence of double-stranded nucleic acids in a sample. In the methods described, nucleic acids present in a fluid sample are translocated through a nanopore, e.g., by application of an electric field to the fluid sample. The current amplitude through the nanopore is monitored during the translocation process and changes in the amplitude are related to the passage of single- or double-stranded molecules through the nanopore. Those methods find use in a variety of applications in which the detection of the presence of double-stranded nucleic acids in a sample is desired.

A silicon nitride membrane provides a robust scaffold to chemical and physical modify a solid state nanopore. Over the past decade, researchers have employed a variety of techniques to modify translocation behavior in solid-state nanopores. Changing pore geometry affects the amount of interaction between a molecule and the nanopore wall, and determines the upper size limit for molecules that may gain access to the pore.[1-4] Nanopores have been drilled in a range of membrane materials, including polymers, glass, silicon dioxide, and graphene, which provide a range of interactions with charged biopolymers.[5-9] Some researchers seek to control interactions by functionalizing the nanopore surface with a layer of organic molecules whose charge and hydrophobicity may be chemically tuned.[10-11] Other researchers have functionalized the mouths of nanopores with individual enzymes to directly regulate translocation speeds.[12-13]

Nanopore surfaces have been modified to discriminate specific "target" sequences of nucleic acids over non-specific sequences using tethered complementary "probe" sequences. Several groups have modified either solid state nanopores or α-hemolysin nanopores with probe sequences to detect target sequences by monitoring the characteristic changes in current associated with a sequences that hybridizes with a capture probe versus sequences that are non-complementary.[14-18] Mussi et al. functionalized large nanopores, 20-80 nm in diameter, with single stranded DNA probes to reduce the size of the nanopore by about 15.3 nm using 45-mer oligonucleotides. Complementary target DNA hybridizes with these probes in the nanopore space resulting in an altered current profile when the target sequence is translocating through the nanopore. Similarly, Howorka et al. covalently linked a single-stranded DNA probe to the lumen of an α-hemolysin nanopore to detect single nucleotide polymorphisms based off of the characteristic translocation time of the target sequence. Translocations associated with a perfectly complementary target sequence and a sequence with a single base mismatch had significantly reduced translocation times where single base mismatches caused 6.5-75 times slower translocations if the mismatch was located at the end or in the middle of the sequence, respectively.

Nanopores can be used to discriminate double-stranded nucleic acids from single-stranded nucleic acids or if a nucleic acid is bound to a protein or not based off of the characteristics of the reduced current as the molecule translocates through the nanopore. This feature has been utilized to discriminate target single-stranded nucleic acids bound to a complementary probe in solution. Several groups have used this strategy to identify the translocation of a target sequence by either discriminating double-stranded versus single-stranded nucleic acid current amplitudes or observing events associated with the unzipping of a double-stranded nucleic acids (i.e. probe hybridized with single-stranded DNA target) as the target sequence is electrophoretically drawn through a nanopore that is too small for double-stranded nucleic acids to translocate (i.e. α-hemolysin nanopore or <2.0 nm in diameter solid state nanopore).[19-22]

Length Profiling: The translocation time is directly related to analyte length as it traverse small nanopores because it forces the analyte to translocate in a linear fashion. Therefore, a nanopore may be used to size analyte. For optimal detection, it is essential that the resolution of a nanopore detector be maximized to improve discrimination between similarly sized analytes. The translocation of an analyte through a bare nanopore is very fast and thus the invention describes a method to slow that rate enable discrimation of analyte sizes.

MicroRNAs: MicroRNAs (miRNAs) are a class of short (~18-24 nucleotides) noncoding RNAs that regulate gene expression at the post-transcriptional level[2]. Depending on the degree of homology to their target sequences, miRNA binding induces either translational repression or cleavage of target mRNAs[2]. As powerful gene regulators, miRNAs play important roles in development, cell differentiation, and regulation of cell cycle, apoptosis and signaling pathways.

Aberrant expression of miRNAs has been found in all types of tumors[4,5]; the different cancer types have distinct miRNA expression profiles[6]. Specific miRNAs, including some miRNA families containing a few single nucleotide polymorphisms, are constantly released from the primary tumor into blood stream and are present in an incredibly stabile form. Recent studies demonstrated that circulating miRNAs are enveloped inside exosomal vesicles and can be transferable and functional in the recipient cells. Thus, detection of tumor specific circulating miRNAs provides a powerful tool for early diagnosis, staging, and monitoring of cancer cells[10].

MiRNA detection: Several technologies including reverse transcription real-time PCR (RT-qPCR) and microarray for miRNA detection have been developed". Each technology has its own advantages, but limitations include requiring enzymatic amplification, target labeling (enzymatic or fluorescent), and semi-quantitative results[14]. In particular the short miRNA sequences make it difficult to selectively design the primers or probes, resulting in cross-hybridization and low selectivity. This is especially true when the miRNAs contain a few or a single nucleotide difference in a miRNA family. Emerging techniques based on colorimetry, bioluminescence, enzyme turnovers and electrochemistry have been proposed, and nanoparticles and molecular beacon have been applied to miRNA detection with high sensitivity and selectivity (review[14]). But the intrinsic versatility needs to be improved. Recently, the integration of single-molecule fluorescence and lock-nucleic acids (LNA)[15] probes provided a sensitive method for miRNA profiling in tissue samples[16], though this method requires expensive equipment.

Protein detection: Biosensors designed to detect the presence of a specific protein of interest often compromise sensitivity for specificity or vice versa. Traditional methods such as the enzyme linked immunosorbent assay (ELISA) rely on antibody recognition of an analyte of interest followed by an enzymatic process to amplify a colorimetric signal to indirectly quantify the concentration of a target protein. Many amplification methods result in compromised specificity to enhance the sensitivity of the biosensor often resulting in suboptimal false positive rates. Newer methods such as using fluorescent molecules or quantum dots attempt to improve this technology by eliminating the need for amplification. However, these methods suffer from reduced sensitivity compared to amplification methods producing suboptimal false negative rates. Therefore, there is a constant need for novel techniques, such as one described in this invention, which exhibit both enhanced sensitivity and specificity to improve the detection of target proteins. Specifically, this invention addresses this need by coupling a highly sensitive single-molecule detection system with a highly specific capture surface.

Scale Inhibitors: An additional embodiment of this application is the use of a nanopore to measure the concentration of a scale inhibitor. Scale inhibitors are chemicals used to prevent the formation of inorganic precipitates on equipment, for example in drilling and pumping oil wells. Formation of mineral scales, such as calcium carbonate, calcium sulfate, calcium phosphate, magnesium silicate, and silica compounds, can increase corrosion rate, restrict flow, and otherwise interfere with operation of equipment. Many scale inhibitors are charged polymers, such as polyacrylic acid, polymaleic acid, polycarboxylic acid, etc. These polymers generally interfere with the growth of a crystal lattice, preventing or reversing scale formation.

Monitoring scale inhibitor concentration: It is essential that scale inhibitor concentrations be monitored to ensure optimal performance of equipment, for example in the case of an oil well. Current techniques employ fluorescent polymers or mass spectrometry to detect concentrations of scale inhibitor with sensitivity down to a few ppm (50 nM-1 uM). Accurate detection of scale inhibitor concentration enables a well to be re-squeezed only as often as is necessary.

Example 1: Poly(benzyloxy glycerol carbonate-co-ε-caprolactone)

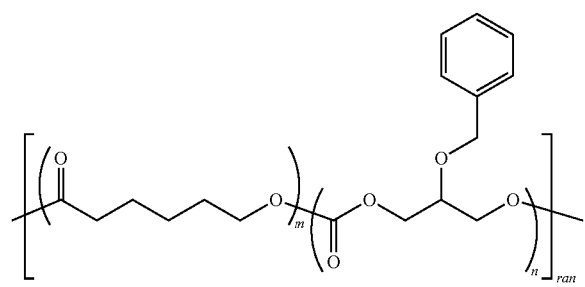

Example 2: Poly(hydroxy glycerol carbonate-co-ε-caprolactone)

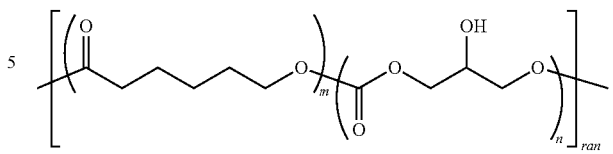

Poly(benzyloxy glycerol carbonate-co-ε-caprolactone) (1.0 g, 2.02 mmol) was dissolved in 50 mL dry dichloromethane inside a Parr bottle. 10% Pd/C (50 mg) and 20% Pd(OH)$_2$/C (50 mg) were then added to the solution. The reaction mixture was evacuated and purged with hydrogen three times. The flask was then pressurized to 60 psi with hydrogen and shaken for 24 hours. The reaction mixture was filtered through Celite and the filter cake washed with 50 mL dichloromethane. The solvents were then evaporated to yield the final polymer. The resulting polymer formed either a viscous oil or white solid precipitate depending on the carbonate content of the copolymer. Copolymers were formed with the following carbonate mole fractions: 0.05, 0.10, 0.20, 0.30, 0.40, 0.50, 1.00.

Table 1 below indicates the composition, molecular weight, and thermal data of the different copolymers, which are illustrated by structural formulas below the table. In Table 1, CL=caprolactone; CG carbonate of glycerol $f_{cg}$=mole percent carbonate monomer in polymerization feed; $F_{cg}$=mole percent carbonate monomer in copolymer; $M_n$=number average molecular weight; PDI=polydispersity index; $T_g$=glass transition temperature; $T_c$=crystallization temperature; $T_m$=melting temperature; $H_f$=heat of fusion.

TABLE 1

| Polymer | $f_{cg}$ | $F_{cg}$ | $M_n$ (theo.) | $M_n$ (SEC) | $M_w/M_n$ | $T_g$ (° C.) | $T_c$ (° C.) | $T_m$ (° C.) | $\Delta H_f$ (J/g) |
|---|---|---|---|---|---|---|---|---|---|
| CL-CG-100-0 | 0 | 0 | 57,000 | 22,700 | 1.47 | −64 | 36 | 57 | 61.5 |
| CL-CG-90-10-Bn | 10 | 11 | 61,700 | 13,300 | 1.67 | −54 | 8 | 40 | 38.5 |
| CL-CG-90-10-OH | 10 | 11 | 57,200 | 12,200 | 1.67 | −59 | 7 | 35 | 32.6 |
| CL-CG-80-20-Bn | 20 | 23 | 66,400 | 10,200 | 1.96 | −49 | −4 | 31 | 25.4 |
| CL-CG-80-20-OH | 20 | 23 | 57,400 | 8,600 | 1.96 | −56 | 0 | 23 | 8.5 |
| CL-CG-80-20-C6-OH | 20 | 23 | 68,800 | 10,100 | 1.91 | −47 | −1 | 43 | 33 |
| CL-CG-80-20-C5-COOH | 20 | 23 | 70,200 | 10,400 | 1.96 | −46 | −5 | 40 | 33 |
| CL-CG-80-20-C6-NH$_2$ | 20 | 23 | 68,700 | 10,100 | 1.94 | −44 | 8 | 44 | 35 |
| CL-CG-70-30-Bn | 30 | 30 | 71,100 | 9,300 | 1.78 | −43 | 3 | 22 | 13.4 |
| CL-CG-60-40-Bn | 40 | 42 | 75,800 | 7,900 | 1.94 | −38 | none | none | none |
| CL-CG-0-100-Bn | 100 | 100 | 104,000 | 3,600 | 3.16 | −10 | none | none | none |

5-(benzyloxymethyl)-1,3-dioxan-2-one (624 mg, 3 mmol) and ε-caprolactone were combined of varying ratios (to a total of 10.0 mmol) in a 10 mL schlenk flask and subsequently evacuated and flushed with N$_2$ three times. Meanwhile, the catalyst (Sn(oct)$_2$, 6.5 μL, 0.02 mmol, monomer/initiator ratio=500) was evacuated in a small flask for 60 minutes. The Schlenk flask was partially submerged in a thermostatted oil bath, preheated to 140° C. Toluene (400 μL) was added to the catalyst and the mixture was injected via syringe to the monomers. The reaction was stirred for 48 hours, removed from heat, and cooled to room temperature. The polymer was dissolved in dichloromethane (10 mL) and precipitated in cold methanol. The solvent was decanted and subsequently dried by evaporation. The resulting polymer formed either a viscous oil or white solid precipitate depending on the carbonate content of the copolymer. Copolymers were formed with the following carbonate mole fractions: 0.05, 0.10, 0.20, 0.30, 0.40, 0.50, 1.00.

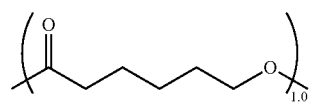

CL-CG-100-0

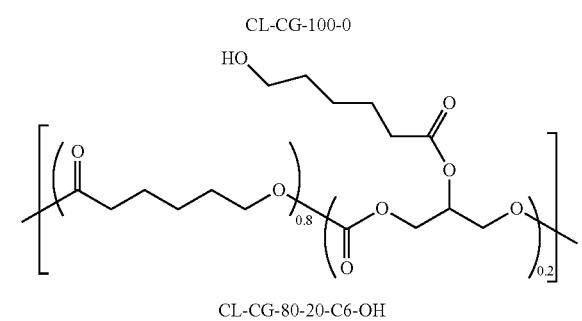

CL-CG-80-20-C6-OH

-continued

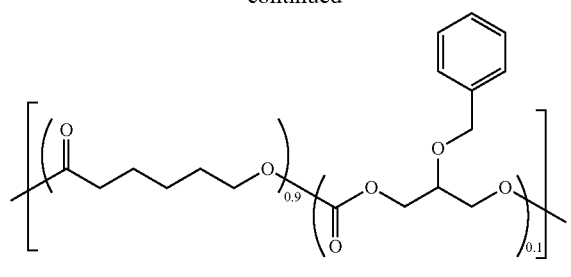

CL-CG-90-10-Bn

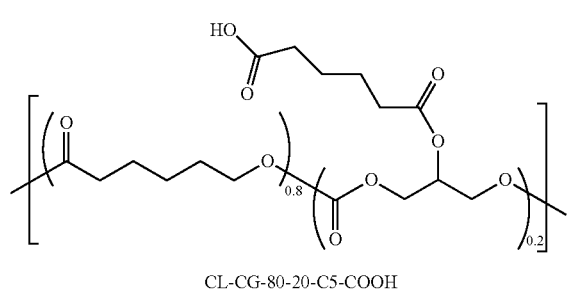

CL-CG-80-20-C5-COOH

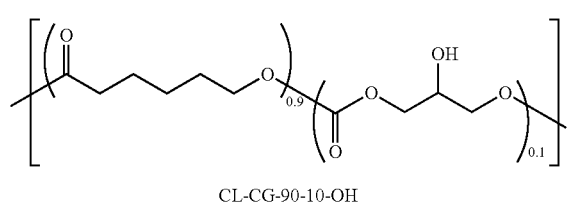

CL-CG-90-10-OH

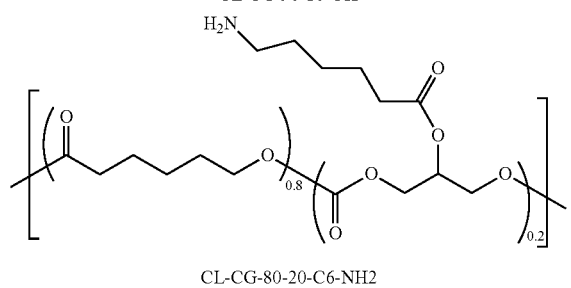

CL-CG-80-20-C6-NH2

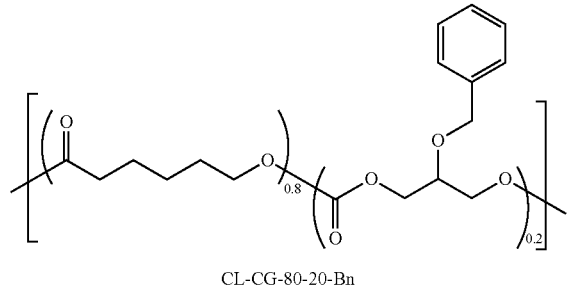

CL-CG-80-20-Bn

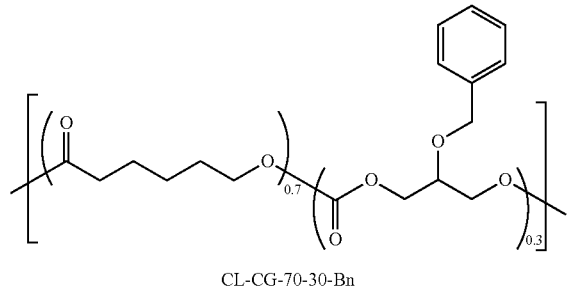

CL-CG-70-30-Bn

-continued

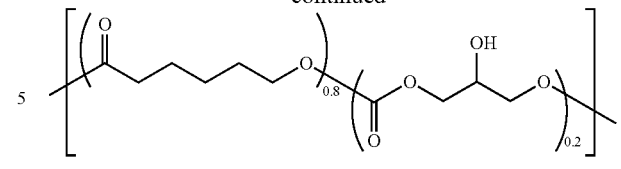

CL-CG-80-20-OH

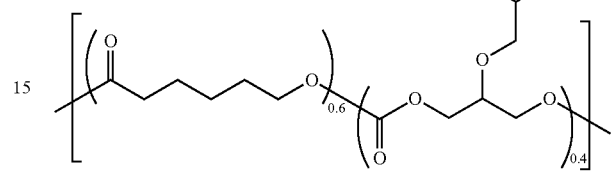

CL-CG-60-40-Bn

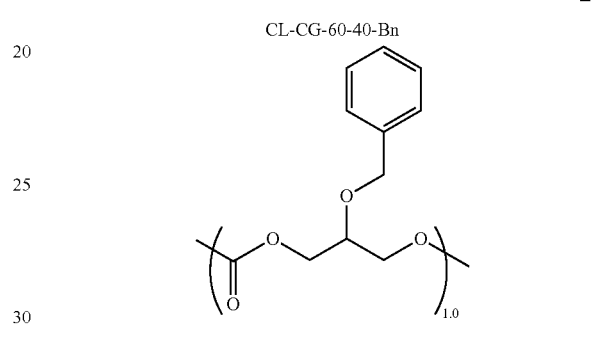

CL-CG-0-100-Bn

Example 3: Poly(myristic acid carbonate-co-ε-caprolactone)

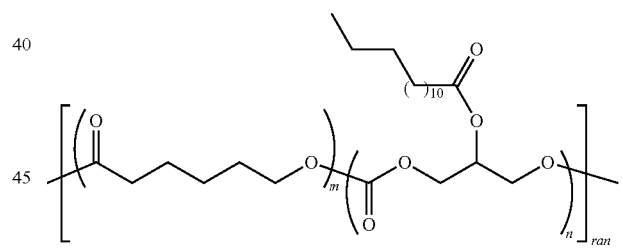

Poly(benzyloxy glycerol carbonate-co-ε-caprolactone) (1.0 g, 2.02 mmol), myristic acid (0.690 g, 3.03 mmol) and dimethylaminopyridine (DMAP) (0.123 g, 1.01 mmol) were dissolved in 100 mL dry dichloromethane. Dicyclohexylcarbodiimide (DCC) (0.500 g, 2.42 mmol) was added to the reaction mixture and a white precipitate formed. The mixture was stirred for 24 hours at room temperature under nitrogen. The precipitate compound was isolated by filtration and the filtrate was concentrated. The concentrated filtrate was dissolved in dichloromethane and precipitated in cold methanol (25 mL). The solvent was decanted and subsequently dried by evaporation. The resulting polymer was a white solid precipitate.

Example 4: Poly(stearic acid carbonate-co-ε-caprolactone)

Poly(benzyloxy glycerol carbonate-co-ε-caprolactone) (1.0 g, 2.02 mmol), stearic acid (0.859 g, 3.03 mmol) and DMAP (0.123 g, 1.01 mmol) were dissolved in 100 mL dry dichloromethane. DCC (0.500 g, 2.42 mmol) was added to the reaction mixture and a white precipitate formed. The mixture was stirred for 24 hours at room temperature under nitrogen. The precipitate compound was isolated by filtration and the filtrate was concentrated. The concentrated filtrate was dissolved in dichloromethane and precipitated in cold methanol (25 mL). The solvent was decanted and subsequently dried by evaporation. The resulting polymer was a white solid precipitate.

Example 5: Poly(oleic acid carbonate-co-ε-caprolactone)

Poly(benzyloxy glycerol carbonate-co-ε-caprolactone) (250 mg, 0.43 mmol) was dissolved in 25 mL of pyridine and cooled to 0° C. Oleoyl chloride (183 mg, 0.65 mmol) was added drop by drop. The mixture was stirred for 24 hours at room temperature under nitrogen. The pyridine was removed under vacuum, the crude product was dissolved in dichloromethane, and precipitated in cold methanol (25 mL). The solvent was decanted and subsequently dried by evaporation. The resulting polymer was a white solid precipitate.

Example 6: Amine Functionalized Poly Carbonate of Glycerol-co-caprolactone

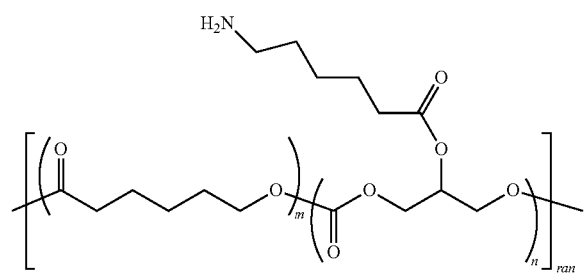

An amine-derivitized copolymer poly(6-amino-hexanoic acid 2-oxo-1,3-dioxan-5-yl ester-co-ε-caprolactone) was prepared using the following methods.

Synthesis of poly(fmoc-6-amino-hexanoic acid 2-oxo-1,3-dioxan-5-yl ester-co-δ-caprolactone)

Fmoc-6-amino-hexanoic acid (0.277 g, 0.78 mol), poly (5-hydroxy-1,3-dioxan-2-one-co-ε-caprolactone) (1.5 g, 2.6 mmol, 22 mol % carbonate), DCC (0.129 g, 0.63 mmol), and DMAP (0.032 g, 0.26 mmol) were dissolved in DCM (20 mL). The solution was stirred at RT for 18 h. The DCU was filtered and the solvent evaporated. The product was dissolved in dichloromethane (10 mL) and precipitated in cold methanol. The solvent was decanted and subsequently dried by evaporation (85% yield). Addition of the amine side chain was determined by the presence of the methylene group nearest the Fmoc protecting group, as well as the Fmoc protecting group itself, with peaks in the $^1$H NMR spectrum at 3.10-3.19 (m, 2H, OCH$_2$), and 4.45 (s, 2H, PhCH$_2$), 7.24-7.38 (m, 5H, aromatic), respectively.

Deprotection of poly(fmoc-6-Amino-hexanoic acid 2-oxo-1,3-dioxan-5-yl ester-co-ε-caprolactone)

The copolymer (300 mg) was dissolved in a 40% mixture of piperidine (16 mL) and dry dimethyl formamide (24 mL) and the reaction was stirred for 90 min. The solvents were evaporated under reduced pressure. The product was dissolved in dichloromethane (10 mL) and precipitated in cold methanol. The solvent was decanted and subsequently dried by evaporation (quantitative yield). Complete deprotection was determined by the absence of the Fmoc protecting group peaks in the $^1$H NMR spectrum at 4.88-4.95 (m, 2H, CH$_2$), and 7.24-7.75 (m, 5H, aromatic).

Example 7: Hydroxyl Functionalized Poly Carbonate of Glycerol-Co-Caprolactone

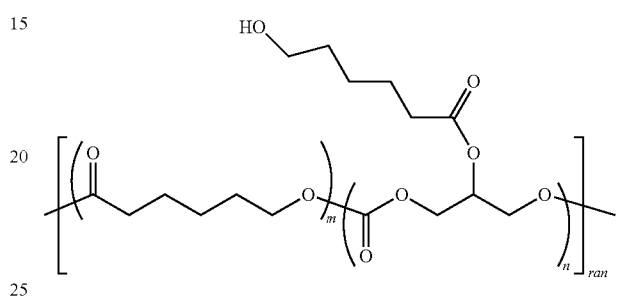

A primary alcohol-derivitized copolymer poly(6-hydroxy-hexanoic acid 2-oxo-1,3-dioxan-5-yl ester-co-ε-caprolactone) was synthesized using the following steps.

Synthesis of 6-benzyloxy-hexanoic acid

ε-caprolactone (10 mL, 0.18 mol), benzyl bromide (13.4 mL, 0.11 mol), and potassium hydroxide (11.3 g, 0.281 mol) were dissolved in toluene (200 mL). The reaction flask was placed in a 120° C. pre-heated oil bath and refluxed overnight under stirring. The mixture was then neutralized using 1 M HCl (300 mL), the toluene evaporated off, and the product extracted using dichloromethane (3×300 mL) to afford a mixture of mono and di-protected 6-hydroxy-hexanoic acid. The crude product was saponificated with 1M sodium hydroxide (200 mL) and methanol (200 mL), extracted with dichloromethane (3×200 mL), and the solvent was evaporated under reduced pressure to afford pure 6-benzyloxy-hexanoic acid (72% yield). $^1$H NMR (CDCl$_3$) 1.38-1.46 (m, 2H, CH$_2$), 1.57-1.68 (m, 4H, CH$_2$CH$_2$), 2.32-2.38 (m, 2H, CH$_2$COOH), 3.42-3.46 (m, 2H, OCH$_2$), 4.48-4.53 (s, 2H, PhCH$_2$), 7.27-7.31 (m, 5H, aromatic).

Poly(6-benzyloxy-hexanoic acid 2-oxo-1, 3-dioxan-5-yl ester-co-ε-caprolactone)

6-Benzyloxy-hexanoic acid (0.173 g, 0.78 mmol), poly (5-hydroxy-1,3-dioxan-2-one-co-ε-caprolactone) (1.5 g, 2.6 mmol, 22 mol % carbonate), DCC (0.129 g, 0.63 mmol), and DMAP (0.032 g, 0.26 mmol) were dissolved in DCM (20 mL). The solution was stirred at RT for 18 h. The DCU was filtered and the solvent evaporated. The product was dissolved in dichloromethane (10 mL) and precipitated in cold methanol. The solvent was decanted and subsequently dried by evaporation (86% yield). Addition of the alcohol side chain was determined by the presence of the methylene group nearest the benzyl protecting group, as well as the benzyl protecting group itself, with peaks in the $^1$H NMR spectrum at 3.40-3.44 (m, 2H, OCH$_2$), and 4.48-4.53 (s, 2H, PhCH$_2$), 7.27-7.31 (m, 5H, aromatic), respectively.

Deprotection of poly(6-benzyloxy-hexanoic acid 2-oxo-1,3-dioxan-5-yl ester-co-ε-caprolactone)

The copolymer (300 mg) was dissolved in 50 mL dry dichloromethane inside a Parr bottle. 10% Pd/C (50 mg) and 20% Pd(OH)$_2$/C (50 mg) were then added to the solution. The reaction mixture was evacuated and purged with hydrogen three times. The flask was then pressurized to 60 psi with hydrogen and shaken for 24 hours. The reaction mixture was filtered through Celite and the filter cake washed with 50 mL dichloromethane. The solvents were then evaporated to yield the final polymer (quantitative yield). Complete deprotection was determined by the absence of the benzyl protecting group peaks in the $^1$H NMR spectrum at 4.48-4.53 (s, 2H, PhCH$_2$), 7.27-7.31 (m, 5H, aromatic).

Example 8: Carboxylic Acid Functionalized Poly Carbonate of Glycerol-Co-Caprolactone

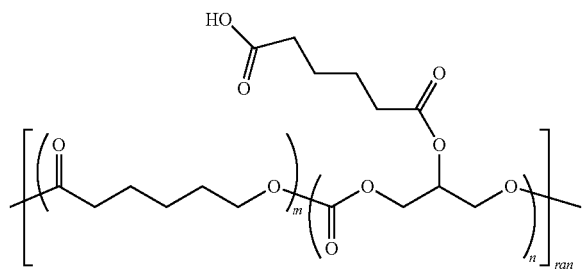

A carboxylic acid-derivitized copolymer poly(hexanedioic acid mono-(2-oxo-1,3-dioxan-5-yl) ester-co-ε-caprolactone) was synthesized using the following steps.

Synthesis of Hexanedioic Acid Monobenzyl Ester polystyrene sulfonate ion exchange resin DOWEX® 50W-X2 (2 g), benzyl formate (10 mL, mol), and adipic acid (2 g, mol) were added to octane (10 mL). The mixture was refluxed for 4 hours at 100° C., and the crude product was purified via silica chromatography to yield a clear, colorless liquid (87% yield). $^1$H NMR (CDCl$_3$) 1.59-1.78 (m, 4H, CH$_2$CH$_2$), 2.33-2.39 (m, 4H, CH$_2$COOH), 5.09 (s, 2H, PhCH$_2$), 7.25-7.30 (m, 5H, aromatic).

Poly(hexanedioic acid mono-(2-oxo-1,3-dioxan-5-yl) ester-co-ε-caprolactone)

Hexanedioic acid monobenzyl ester (0.184 g, 0.78 mmol), poly(5-hydroxy-1,3-dioxan-2-one-co-ε-caprolactone) (1.5 g, 2.6 mmol, 22 mol % carbonate), DCC (0.129 g, 0.63 mmol), and DMAP (0.032 g, 0.26 mmol) were dissolved in dichloromethane (20 mL). The solution was stirred at RT for 18 h. The DCU was filtered and the solvent evaporated. The product was dissolved in dichloromethane (10 mL) and precipitated in cold methanol. The solvent was decanted and subsequently dried by evaporation (83% yield). Addition of the carboxylic acid side chain was determined by the presence of the benzyl protecting group, with peaks in the $^1$H NMR spectrum at 5.06 (s, 2H, PhCH$_2$), 7.27-7.33 (m, 5H, aromatic).

Deprotection of poly(6-benzyloxy-hexanoic acid 2-oxo-1,3-dioxan-5-yl ester-co-ε-caprolactone)

The copolymer (300 mg) was dissolved in 50 mL dry dichloromethane inside a Parr bottle. 10% Pd/C (50 mg) and 20% Pd(OH)$_2$/C (50 mg) were then added to the solution. The reaction mixture was evacuated and purged with hydrogen three times. The flask was then pressurized to 60 psi with hydrogen and shaken for 24 hours. The reaction mixture was filtered through Celite and the filter cake washed with 50 mL dichloromethane. The solvents were then evaporated to yield the final polymer (quantitative yield). Complete deprotection was determined by the absence of the benzyl protecting group peaks in the $^1$H NMR spectrum at 5.06 (s, 2H, PhCH$_2$), 7.27-7.33 (m, 5H, aromatic).

Example 9: 1-(2-nitrophenyl)Ethyl (NPE) Functionalized Poly Carbonate of Glycerol-Co-Caprolactone: UV (365 nm) Light Activate

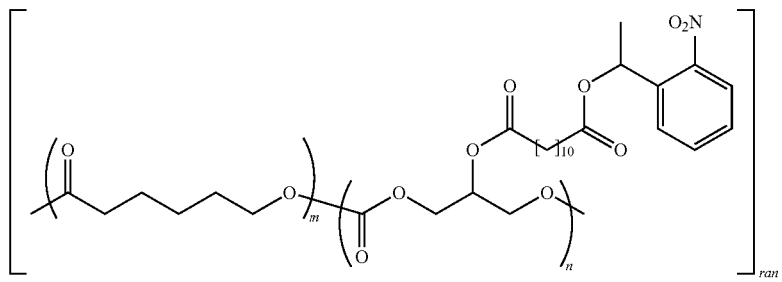

A carboxylic acid-derivitized copolymer poly(glycerol 12-(1-(2-nitrophenyl)ethoxy)-12-oxododecanoic acid-co-ε-caprolactone) was synthesized using the following steps.

Synthesis of 2-(1-(2-nitrophenyl)ethoxy)-12-oxododecanoic acid

Dodecanedioic acid (6 g, 26.1 mmol), cat. DMAP, and 1-2(-nitrophenyl)ethanol (1.45 g, 8.7 mmol) were dissolved in DMF (70 mL), and the solution was cooled to 0° C. To the mixture was added 1-Ethyl-3-(3-dimethylaminopropyl)carbodiimide (EDCI) (2.5 g, 13 mmol) and the reaction was stirred overnight and warmed to room temperature. The solution was taken up into EtOAc (500 mL) and washed with water, 1N HCl, and sat. NH4Cl solutions. The organic layer was dried over Na2SO4. The volatiles were evaporated and the residue was purified on silica gel chromatography (gradient hexanes:EtOAc, 5:1 to 4:1 to 3:1 to 2:1), affording 2-(1-(2-nitrophenyl)ethoxy)-12-oxododecanoic acid as a thick oil in 31% yield. 1H NMR (300 MHz, CDCl3): δ=1.21

(br.s, 12H), 1.49-1.66 (m, 7H), 2.20-2.33 (m, 4H), 6.27 (q, 1H, J=6 Hz), 7.30-7.43 (m, 1H), 7.53-7.65 (m, 2H), 7.87 (d, 1H, J=8.2 Hz). 13C NMR (300 Hz, CDCl3): δ=20.8, 21.9, 24.6, 24.7, 28.7, 29.0, 29.1, 29.3, 34.0, 34.2, 67.8, 124.3, 127.1, 128.3, 133.5, 138.0, 147.7, 172.7, 177.6, 180.3.

Synthesis of poly(glycerol 12-(1-(2-nitrophenyl)ethoxy)-12-oxododecanoic acid-co-ε-caprolactone)

2-(1-(2-nitrophenyl)ethoxy)-12-oxododecanoic acid (1.02 g, 2.7 mmol), cat. 4-dimethylaminopyridine (DMAP), PGC (1.3 g, 2.2 mmol) were dissolved in DCM at room temperature. To the mixture was added N,N'-dicyclohexylcarbodiimide (DCC) (924 mg, 4.5 mmol) and the reaction was stirred overnight. The solution was filtered to remove the N,N'dicyclohexylurea, a byproduct of the reaction, and then rotovaped so that the DCM volume was 5 mL. The polymer was precipitated in 30 mL methanol overnight at −20° C. and then filtered and washed with methanol affording poly(glycerol 12-(1-(2-nitrophenyl)ethoxy)-12-oxododecanoic acid-co-ε-caprolactone) as a white solid in 69.3% yield. 1H NMR (300 MHz, CDCl3): δ=1.13-1.44 (m, 21H), 1.46-1.74 (m, 28H), 2.15 (s, 3H), 2.21-2.45 (m, 21H), 3.90-4.42 (m, 17H), 5.18-5.33 (m, 1H), 6.29 (q, J=6.48 Hz, 1H), 7.36-7.48 (m, 1H), 7.60 (d, J=4.12 Hz, 2H), 7.91 (d, J=8.24 Hz, 1H). 13C NMR (300 Hz, CDCl3): δ=22.0, 24.5, 25.5, 28.3, 29.2, 29.3, 33.8, 34.1, 34.3, 67.9, 68.2, 68.3, 124.4, 127.1, 128.2, 133.5, 138.1, 147.7, 154.8, 155.2, 172.6, 172.9, 173.6. Differential Scanning calorimetry: Tg=−50.13° C., Tc=−16.14° C., Tm=37.42° C. UV-vis absorbance. 20,127 g/mol, PDI=1.634 as determined by GPC.

Example 10: 6-(((1-(5-methoxy-2-nitro-4-(2-(stearoyloxy)ethoxy)phenyl)ethoxy)carbonyl)amino)hexanoic acid Functionalized Poly Carbonate of Glycerol-co-caprolactone: UV (365 nm) light activated

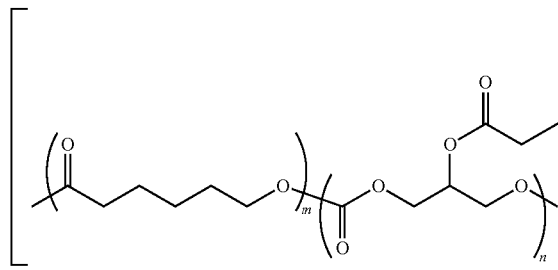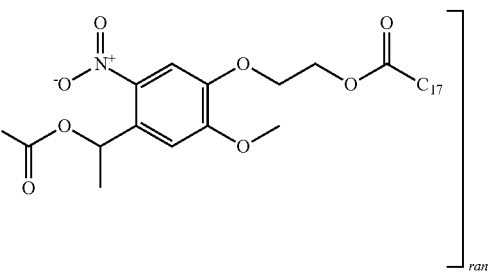

A carboxylic acid-derivitized copolymer poly(glycerol 6-(((1-(5-methoxy-2-nitro-4-(2-(stearoyloxy)ethoxy)phenyl)ethoxy)carbonyl)amino)hexanoic acid-co-ε-caprolactone) was synthesized using the following steps.

Synthesis of 4-(2-bromoethoxy)-3-methoxybenzaldehyde

Vanillin (2.5 g, 16.4 mmol) was added to dibromoethane (12.3 g, 65.8 mmol) and potassium carbonate (2.5 g, 18 mmol) in 100 mL of acetonitrile. The reaction was refluxed for 12 hours at 82° C. The acetonitrile was then concentrated and the product was extracted in ethyl acetate. The solution was washed with DI water and brine and the excess potassium bromide was filtered. The organic phase was concentrated and placed under high vacuum for 18 hours to remove any excess dibromoethane. The product was purified using a silica gel column with 100% dichloromethane to afford 4-(2-bromoethoxy)-3-methoxybenzaldehyde as a white powder in 66% yield. 1H NMR (300 MHz, CDCl3): δ=3.71 (t, 2H, J=6 Hz), 3.93 (s, 3H), 4.41 (t, 2H, J=7.5 Hz), 6.99 (d, 1H, J=9 Hz), 7.44 (m, 2H), 9.86 (s, 1H). 13C NMR (300 MHz, CDCl3): δ=28.25, 56.07, 68.69, 109.76, 112.33, 126.35, 130.75, 149.92, 152.83, 190.81.

Synthesis of 4-(2-bromoethoxy)-5-methoxy-2-nitrobenzaldehyde

Nitric acid (350 mL) was cooled to 0° C. in an ice bath and then 4-(2-bromoethoxy)-3-methoxybenzaldehyde (3.67 g, 14.2 mmol) was added to the nitric acid. The reaction was removed from the ice bath and allowed to stir and heat to room temperature over 2 hours. Once complete, the reaction was quenched with cold water (1 L) yielding a crude yellow powder which was filtered and recrystallized in ethanol to afford 4-(2-bromoethoxy)-5-methoxy-2-nitrobenzaldehyde as a yellow powder in 73% yield. 1H NMR (300 MHz, CDCl3): δ=3.73 (t, 2H, J=6 Hz), 4.02 (s, 1H), 4.48 (t, 2H, J=7.5 Hz), 7.42 (s, 1H), 7.62 (s, 1H), 10.44 (s, 1H). 13C NMR (300 MHz, CDCl3): δ=27.81, 56.79, 69.35, 105, 108.85, 110.36, 126.24, 143.44, 150.78, 153.65, 187.65.

Synthesis of 2-(4-formyl-2-methoxy-5-nitrophenoxy)ethyl stearate 4-(2-bromoethoxy)-5-methoxy-2-nitrobenzaldehyde (2.2 g, 7.2 mmol) was added to stearic acid (4.13 g, 14.4 mmol), potassium carbonate (2.99 g, 21.6 mmol), and a catalytic amount of sodium iodide in 100 mL dimethylformamide. The reaction was heated to 80° C. for 18 hours under nitrogen. The reaction was extracted into 500 mL of ethyl acetate and washed with DI water, 0.1 N HCl, and brine. A silica gel column was used with 1:1 hexanes:ethyl acetate with 1% triethylamine to afford 2-(4-formyl-2-methoxy-5-nitrophenoxy)ethyl stearate as a yellow powder in 91.1% yield. 1H NMR (300 MHz, CDCl3): δ=0.79 (br. s., 3H), 1.16 (m, 28H), 1.54 (m, 2H), 2.27 (t, 2H, J=7.5 Hz), 3.93 (s, 3H), 4.31 (t, 2H, J=6 Hz), 4.44 (t, 2H, J=6 Hz), 7.33 (s, 1H), 7.58 (s, 1H), 10.33 (s, 1H).

Synthesis of 2-(4-(1-hydroxyethyl)-2-methoxy-5-nitrophenoxy)ethyl stearate 200 mL of dry DCM was cooled to 0° C. in an ice bath. 2-(4-formyl-2-methoxy-5-nitrophenoxy)ethyl stearate (4.25 g, 8.4 mmol) was added to the DCM and trimethyl aluminum (2.41 g, 16.7 mmol) was added drop-wise over 45 minutes. The reaction was quenched with ice cubes followed by 100 mL of DI water and washed with cold 1N NaOH and brine. The product was dried over sodium sulfate and the volatiles were evaporated under high vacuum for 18 hours affording 2-(4-(1-hydroxyethyl)-2-methoxy-5-nitrophenoxy)ethyl stearate in 99% yield. 1H NMR (300 MHz, CDCl3): δ=0.78 (t, 3H, J=6 Hz), 1.16 (m, 28H), 1.4 (d, 3H, J=4.5 Hz), 1.52 (m, 2H), 2.25 (t, 2H, J=7.5 Hz), 3.86 (s, 3H), 4.17 (t, 2H, J=3 Hz), 4.36 (t, 2H, J=3 Hz), 5.43 (q, 1H, J=6 Hz), 7.23 (s, 1H), 7.46 (s, 1H). 13C NMR (300 MHz, CDCl3): δ=14.03, 22.62, 24.43, 24.77, 29.04, 29.2, 29.3, 29.4, 29.55, 29.59, 29.63, 31.85, 34.02, 56.2, 62.2, 65.43, 67.47, 108.9, 109.69, 138.06, 139.06, 146.31, 154.15, 173.71.

Synthesis of 2-(2-methoxy-5-nitro-4-(1-(((4-nitrophenoxy)-carbonyl)-oxy)ethyl)-phenoxy)-ethyl stearate 2-(4-(1-hydroxyethyl)-2-methoxy-5-nitrophenoxy)ethyl stearate (1 g, 1.9 mmol) was added to 4-nitrophenyl chloroformate (2.32 g, 11.5 mmol) and triethylamine (1.74 g, 17.2 mmol) in dry DCM (50 mL) and stirred for 18 hours. The DCM was concentrated several times to remove excess TEA. A silica gel column was used to purify the product using a 3:1 hexane:ethyl acetate mixture. The product was then precipitated in diethyl ether and filtered to afford 2-(2-methoxy-5-nitro-4-(1-(((4-nitrophenoxy)carbonyl)oxy)ethyl)phenoxy)ethyl stearate in 42.9% yield. 1H NMR (400 MHz, CDCl3): δ=0.79 (t, 3H, J=6 Hz), 1.22 (m, 28H), 1.52 (m, 2H), 1.7 (m, 2H), 2.27 (t, 2H, J=7.5), 3.93 (s, 3H), 4.23 (m, 2H), 4.40 (m, 2H), 6.46 (q, 1H, J=6 Hz), 7.09 (s, 1H), 7.25 (m, 2H), 7.56 (s, 1H), 8.15 (m, 2H).

Synthesis of 6-(((1-(5-methoxy-2-nitro-4-(2-(stearoyloxy)ethoxy)phenyl-ethoxy)-carbonyl)-amino)hexanoic acid 2-(2-methoxy-5-nitro-4-(1-(((4-nitrophenoxy)carbonyl)-oxy)ethyl)phenoxy)ethyl stearate (0.520 g, 0.76 mmol) was dissolved in tetrahydrofuran (THF). 6-aminocaproic acid (0.99 g, 7.6 mmol) was added to triethylamine (0.764 g, 7.6 mmol) and dissolved in 2:1 THF and combined with the previous THF mixture to make a 4:1 THF:water mixture. The reaction was mixed for 18 hours at room temperature. The THF was concentrated and the reaction was extracted using DCM. The organic phase was washed with concentrated sodium chloride and brine. A silica gel column was used to purify the product (gradient: 4:1, 3:1, 2:1, 1:1, 1:4 hexanes: ethyl acetate) to afford 6-(((1-(5-methoxy-2-nitro-4-(2-(stearoyloxy)ethoxy)phenyl)ethoxy)carbonyl)amino) hexanoic acid in 71.4% yield. 1H NMR (400 MHz, CDCl3): δ=0.76 (m, 3H), 1.18 (m, 30H), 1.43 (m, 4H), 1.53 (m, 2H), 2.28 (t, 4H, J=7.5 Hz), 3.07 (m, 2H), 3.88 (s, 3H), 4.20 (t, 2H, 4.5 Hz), 4.39 (t, 2H, J=4.5 Hz), 6.29 (q, 1H, J=6 Hz), 7.20 (s, 1H), 7.56 (s, 1H).

Synthesis of poly(glycerol 6-(((1-(5-methoxy-2-nitro-4-(2-(stearoyloxy)-ethoxy)-phenyl)-ethoxy) carbonyl)amino)hexanoic acid-co-ε-caprolactone)

6-(((1-(5-methoxy-2-nitro-4-(2-(stearoyloxy)ethoxy)phenyl)ethoxy)carbonyl)amino)hexanoic acid (0.127 g, 0.187 mmol), cat. 4-dimethylaminopyridine (DMAP), PGC (0.0899 g, 0.155 mmol) were dissolved in DCM (3 mL) at room temperature. To the mixture was added N,N'-dicyclohexylcarbodiimide (DCC) (0.0642 g, 0.311 mmol) and the reaction was stirred overnight. The solution was filtered to remove the N,N'dicyclohexylurea, a byproduct of the reaction, and then rotovaped so that the DCM volume was 5 mL. The polymer was precipitated in 30 mL methanol overnight at −20° C. and then filtered and washed with methanol affording poly(glycerol 6-(((1-(5-methoxy-2-nitro-4-(2-(stearoyloxy)ethoxy)phenyl)ethoxy)carbonyl)amino) hexanoic acid-co-ε-caprolactone) as a white solid in 69.5% yield. Addition of the side chain was determined by 1HNMR (400 MHz, CDCl3) by the presence of the following peaks: 3.07 (m, 2H), 3.88 (s, 3H), 4.20 (t, 2H, 4.5 Hz), 4.39 (t, 2H, J=4.5 Hz), 6.29 (q, 1H, J=6 Hz), 7.20 (s, 1H), 7.56 (s, 1H), that are also found in the side chain's NMR. In addition, the single hydrogen on the carbon in the glycerol monomer that links the side chain to the polymer backbone is present at 5.37 (t, 1H, J=4.5 Hz).

Example 11: COOH-(PEG$_{3400}$)-Maleimide Functionalized Poly Carbonate of Glycerol-co-caprolactone

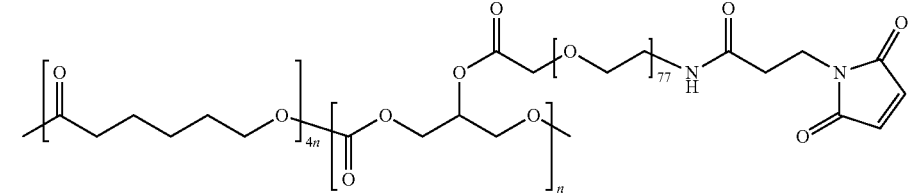

Synthesis of poly(glycerol-PEG$_{3400}$-Maleimide-co-ε-caprolactone)

COOH-PEG$_{3400}$-Maleimide (0.25 g, 0.07 mmol) (purchased from JenKem Technology) was added to poly(glycerol-co-ε-caprolactone) (0.034 g, 0.059 mmol), and cat. 4-dimethylaminopyridine (DMAP) in dry DCM (3.0 mL). To the mixture was added N,N'-dicyclohexylcarbodiimide (DCC) (0.024 g, 0.12 mmol) and the reaction was stirred overnight at room temperature. The solution was filtered to remove the N,N'dicyclohexylurea, a byproduct of the reaction, and then rotovaped so that the DCM was 1 mL. The polymer was precipitated in 30 mL of diethyl ether and filtered and washed with diethyl ether. The excess COOH-PEG$_{3400}$-Maleimide was dissolved in water and the polymer was centrifuged to the bottom of a tube to allow the water to be removed. The polymer was isolated and dried under high vacuum for 18 hours to afford the poly(glycerol-PEG$_{3400}$-Maleimide-co-ε-caprolactone) product in 15% yield. By GPC, the polymer weight increased proportional to 15% of the hydroxyl groups being functionalized with the COOH-PEG$_{3400}$-Maleimide side chain.

Example 12: Avidin Functionalized Carboxylic Acid Functionalized Poly Carbonate of Glycerol-Co-Caprolactone Synthesis of Butanedioic Acid Monobenzyl Ester polystyrene sulfonate ion exchange resin DOWEX® 50W-X2 (2 g), benzyl formate (10 mL, mol), and succinic acid (2 g, mol) were added to octane (10 mL). The mixture was refluxed for 4 hours at 100° C., and the crude product was purified via silica chromatography to yield a clear, colorless liquid. $^1$H NMR consistent with structure.

Poly(butanedioic acid mono-(2-oxo-1,3-dioxan-5-yl) ester-co-ε-caprolactone)

Butanedioic acid monobenzyl ester (0.184 g, 0.78 mmol), poly(5-hydroxy-1,3-dioxan-2-one-co-ε-caprolactone) (1.5 g, 2.6 mmol, 22 mol % carbonate), DCC (0.129 g, 0.63 mmol), and DMAP (0.032 g, 0.26 mmol) were dissolved in dichloromethane (20 mL). The solution was stirred at RT for 18 h. The DCU was filtered and the solvent evaporated. The product was dissolved in dichloromethane (10 mL) and precipitated in cold methanol. The solvent was decanted and subsequently dried by evaporation (83% yield). Addition of the carboxylic acid side chain was determined by the presence of the benzyl protecting group, with peaks in the $^1$H NMR spectrum at 5.06 (s, 2H, PhCH$_2$), 7.27-7.33 (m, 5H, aromatic).

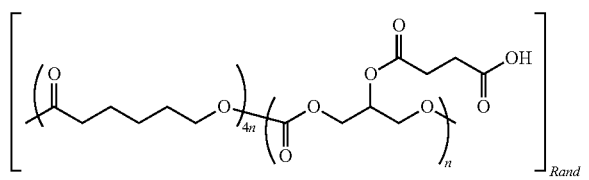

Deprotection of poly(6-benzyloxy-butanoic acid 2-oxo-1,3-dioxan-5-yl ester-co-ε-caprolactone)

The copolymer (300 mg) was dissolved in 50 mL dry dichloromethane inside a Parr bottle. 10% Pd/C (50 mg) and 20% Pd(OH)$_2$/C (50 mg) were then added to the solution. The reaction mixture was evacuated and purged with hydrogen three times. The flask was then pressurized to 60 psi with hydrogen and shaken for 24 hours. The reaction mixture was filtered through Celite and the filter cake washed with 50 mL dichloromethane. The solvents were then evaporated to yield the final polymer (quantitative yield). Complete deprotection was determined by the absence of the benzyl protecting group peaks in the $^1$H NMR spectrum at 5.06 (s, 2H, PhCH$_2$), 7.27-7.33 (m, 5H, aromatic).

Synthesis of Avidin functionalized poly(6-benzyloxy-butanoic acid 2-oxo-1,3-dioxan-5-yl ester-co-ε-caprolactone)

A butanedioic acid functionalized poly(glycerol-co-ε-caprolactone) (PGC) polymer (16,000 g/mol, PDI 2.4) was electrospun as a copolymer blend with poly-caprolactone (PCL) in a 3:7 ratio, respectively, dissolved in a 5:1 ratio of chloroform:methanol, respectively. The carboxylic acid functionalized electrospun mesh was coupled to Avidin through free amines on the Avidin surface using 1-Ethyl-3-(3-dimethylaminopropyl)carbodiimide (EDC) coupling with an Hydroxybenzotriazole (HOBt) catalyst. The resulting electrospun mesh has amide linked Avidin proteins at the surface of the fibers for subsequent binding to biotinylated compounds. Fluorescein conjugated to Biotin was used to quantify the Avidin binding to the electrospun mesh surface.

Example 13: Thermally Stable Electrospun Meshes of Poly(Oxanorbornene) Derivatives

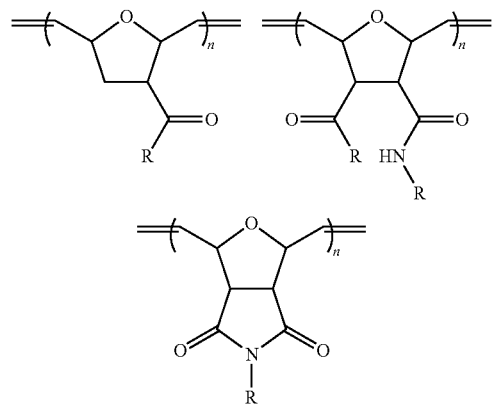

R: —H, —OH, saturated alliphatic chain, biotin, poly(ethylene-glycol), aromatic group

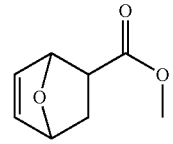

Synthesis of Oxanorborene-Methylester Monomer

The oxanorbornene-methylester monomer was synthesized according to a previously published protocol: M. Wathier, B. Lakin, P. N. Bansal, S. S. Stoddart, B. D. Snyder, M. W. Grinstaff, *J. Am. Chem. Soc.* 2013, 135, 4930.

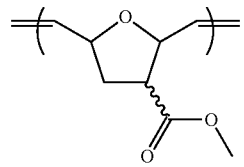

Synthesis of Poly(Oxanorborene-Methylester

The poly(oxanorbornene-methylester) polymer was synthesized according to a previously published protocol: M. Wathier, B. Lakin, P. N. Bansal, S. S. Stoddart, B. D. Snyder, M. W. Grinstaff, *J. Am. Chem. Soc.* 2013, 135, 4930.

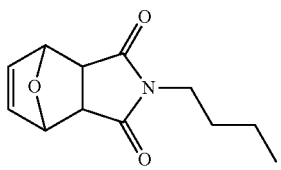 [SMILES: CCCCN1C(=O)C2C3C=CC(O3)C2C1=O]

Synthesis of Oxanorborene-Dicarboxamide-Butyl Monomer

Oxanorbornene-anhydride (10 grams) (CAS: 6118-51-0) was dissolved into a 1:1 Tetrahydrofuran:Methanol mixture and cooled to 0° C. Butyl amine (6.51 mL) was added to the mixture dropwise over 30 minutes. The reaction was stirred for an additional 30 minutes before being heated to 65° C. Bis(trimethylsilyl)amine (15.1 mL) was added to the reaction which was stirred at 65° C. for 18 hours. The volatiles were removed under high vacuum and the crude was dissolved into dichloromethane and washed with saturated sodium bicarbonate and 2N HCl. The product was dried over magnesium sulfate and the volatiles were removed. The product was purified through recrystallization in diethyl ether (yield=27%). $^1$H NMR was performed and is consistent with the structure. This is a modified protocol from J. A. van Hensbergen, R. P. Burford, A. B. Lowe, *J. Polym. Sci. Part A Polym. Chem.* 2013, 51, 487.

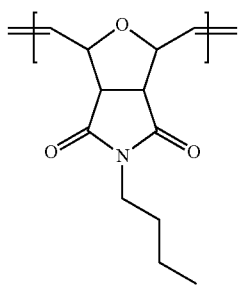

Synthesis of High Molecular Weight Poly(Oxanorbornene-Dicarboxamide-Butyl)

Under dry conditions, the oxanorborene-dicarboxamide-butyl monomer was polymerized through the addition of the GRUBBS CATALYST™ $3^{rd}$ generation metathesis catalyst (CAS: 9001689-53-1) in dry THF. The reaction was stirred for 18 hours producing a viscous liquid. Additional THF was added to reduce the viscosity followed by the addition of ethyl vinyl ether to terminate the polymerization. The polymer was precipitated into cold methanol. A summary of the polymerizations and polymer properties can be found in Table 2.

TABLE 2

| Conditions | $Mn_{theo}$ (kg/mol) | $M_n$* (kg/mol) | D* $(Mw/M_n)$ | Tg** (° C.) |
|---|---|---|---|---|
| Benzene, 25° C. | 250 | 151 | 1.53 | 127 |
| THF, 0° C. → 25° C. | 500 | 319 | 1.76 | 125 |
| THF, 25° C. | 500 | 395 | 1.75 | 124 |
| THF, 25° C., dilute (25 mg/mL vs. 250 mg/mL) | 50 | 76 | 1.31 | N/A |

*Gel permeation chromatography performed in THF eluent on a Waters Styragel HR5E column against poly(styrene) standards.
**Glass transition temperature (Tg) determined after 2 heat/cool cycles to 220° C.→−10° C.→220° C. at 10° C. per minute

Electrospinning of Poly(Oxanorbornene) Derivatives

Poly(oxanorbornene) derivatives were dissolved in various electrospinning solvent systems (Chloroform:Methanol, Chloroform:Dimethylformamide, Hexafluoro-2-propanol, etc.) producing various fiber morphologies. The working distance, voltage, and needle gauge were adjusted to produce consistent fiber morphology for each solvent system.

Example 14: Biotin Functionalized Poly(Oxanorbornene) Derivatives

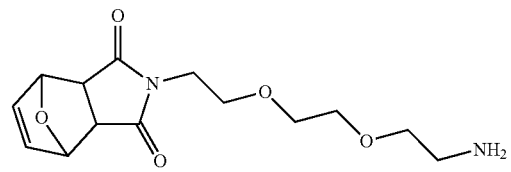 [SMILES: NCCOCCOCCN1C(=O)C2C3C=CC(O3)C2C1=O]

Synthesis of Oxanorborene-Dicarboxamide-Diethyleneglycol-Amine Monomer

Oxanorbornene-anhydride (1 grams) (CAS: 6118-51-0) was dissolved into excess 2,2-(ethylenedioxy) bis(ethylamine) (8.8 mL) and heated to 80° C. for 18 hours. The excess 2,2-(ethylenedioxy) bis(ethylamine) was removed under high vacuum. A silica gel column was used to purify the product using dichloromethane and methanol as the eluent. $^1$H NMR was performed and is consistent with the structure. This is a modified protocol from B. Chen, H. F. Sleiman, *Macromolecules* 2004, 37, 5866.

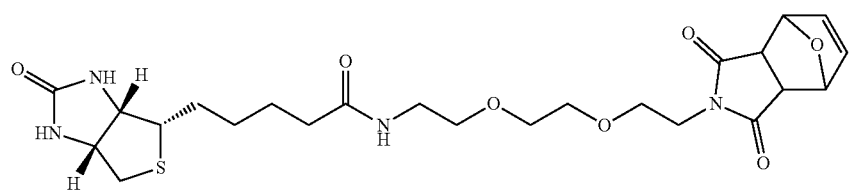 [SMILES: O=C(CCCC[C@@H]1SC[C@@H]2NC(=O)N[C@@H]21)NCCOCCOCCN1C(=O)C2C3C=CC(O3)C2C1=O]

Synthesis of Oxanorborene-Dicarboxamide-Diethyleneglycol-Biotin Monomer oxanorborene-dicarboxamide-diethyleneglycol-amine (250 mg) was dissolved into dry DMF with the N-hydroxysuccinimide ester of biotin. N,N-Diisopropylethylamine (293 µL) was added to the reaction mixture which was stirred in dry conditions for 18 hours. The DMF was removed under high vacuum and the crude was dissolved into DCM to be washed with 0.1 N HCl and Brine. The product was dried over sodium sulfate and the volatiles were removed (yield: 19.5%). $^1$H NMR was performed and is consistent with the structure. This is a modified protocol from N. B. Sankaran, A. Z. Rys, R. Nassif, M. K. Nayak, K. Metera, B. Chen, H. S. Bazzi, H. F. Sleiman, *Macromolecules* 2010, 43, 5530.

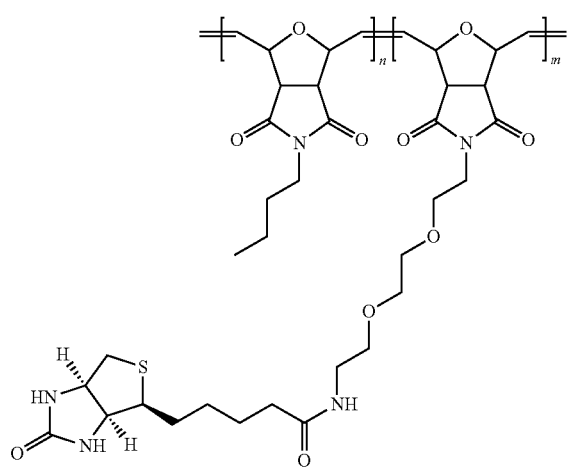

Co-Polymerization of Oxanorborene-Dicarboxamide-Butyl (ONB-DCI-but) and Oxanorbornene-Dicarboxamide-Diethyleneglycol-Biotin (ONB-DCI-DEG-Biotin)

Under dry conditions, the ONB-DCI-but and ONB-DCI-DEG-biotin monomers were co-polymerized through the addition of the GRUBBS CATALYST™ 3$^{rd}$ generation metathesis catalyst (CAS: 9001689-53-1) in dry THF. The reaction was stirred for 18 hours producing a viscous liquid. Additional THF was added to reduce the viscosity followed by the addition of ethyl vinyl ether to terminate the polymerization. The polymer was precipitated into cold methanol.

Example 15: Stimuli Responsive Release Unit: Native Chemical Ligation

A stimuli responsive tether was synthesized to connect a maleimide group to a biotin group through a thiolester linkage which is susceptible to native chemical ligation in the presence of cysteine methylester. This tether can be utilized in example 33 as the release unit responsible for the stimuli responsive detection of the presence of a target analyte captured onto a nanofiber mesh surface using a released reporter molecule detected using a nanopore.

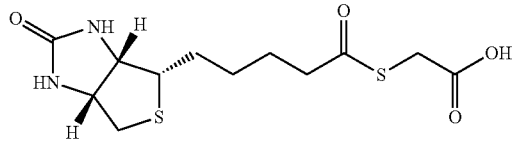 [SMILES: O=C(O)CSC(=O)CCCC[C@@H]1SC[C@@H]2NC(=O)N[C@@H]21]

Synthesis of Biotin-Thiolester

The N-hydroxysuccinimide ester of biotin (250 mg) and thioglycolic acid (51 µL) were dissolved into dry DMF. N,N-Diisopropylethylamine (254 µL) was added and the reaction was stirred at room temperature for 18 hours. The DMF was removed under high vacuum and the product was precipitated into cold diethyl ether (yield: 90%). $^1$H NMR was performed and is consistent with the structure.

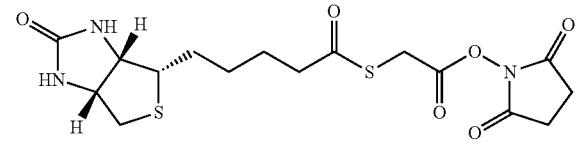 [SMILES: O=C1N[C@H]2[C@H](CS[C@H]2CCCCC(=O)SCC(=O)ON2C(=O)CCC2=O)N1]

Synthesis of Biotin-Thiolester-NHS

N-hydroxysuccinimide (34 mg) and biotin-thiolester (100 mg) were dissolved into dry DMF. N,N'-dicyclohexylcarbodiimide (78 mg) was added and the reaction was stirred at room temperature for 18 hours. After reacting, the dicyclohexylurea was filtered and the DMF removed under high vacuum. The product was precipitated into cold diethyl ether (yield: 96.3%). $^1$H NMR was performed and is consistent with the structure.

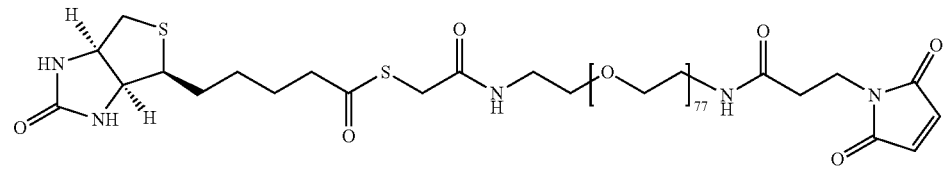

Synthesis of Biotin-Thiolester-PEG$_{3400}$-Maleimide

Biotin-Thiolester-NHS (28 mg) and commercially available Amine-PEG-Maleimide (3,400 g/mol) (JenKem) were dissolved in dry DMF. N,N-Diisopropylethylamine (23 µL) was added and the reaction was stirred at room temperature for 18 hours. The DMF was removed under high vacuum and the product was dissolved in water. The aqueous solution was dialyzed using 1000 molecular weight cutoff dialysis tubing placed in deionized water for 3 days (yield: 73.3%). ¹H NMR and ¹³C NMR were performed and are consistent with the structure.

Example 16: Formation of Poly(Caprolactone) Non-Woven Meshes

Non-woven polymer meshes and blends were prepared using an electrospinning apparatus. Solutions of polycaprolactone were prepared (20 w/v %) in a 5:1 chloroform/methanol mixture with or without the inclusion of 1-20 w/w % poly(glycerol monostearate-co-caprolactone). Each solution was loaded into a glass syringe and placed into a syringe pump set at a flow rate of 25 mL/hr. A 15-18 kV high voltage lead was applied at the base of the syringe needle. A grounded rotating collector was covered in aluminum foil and placed 20-30 cm away from the needle. Following 30-60 minutes of electrospinning, the resulting non-woven polymer meshes were peeled off the aluminum foil backing for future use. Meshes created in this manner have average fiber diameters between 1-10 µm. For poly(glycerol monostearate-co-caprolactone), the monomer ratio in the final polymer was about 80 mol % caprolactone and the molecular weight was about 10,000 Da. The molecular weight for the poly(caprolactone) was between 70,000-90,000 Da.

The resulting meshes are 300 µm thick, with an average fiber size of ≈7 µm. The wettability of the meshes was assessed using static contact angle measurements, where electrospun PCL meshes doped with PGC-C18 asymptotically approach 153° with 50 wt % doping. Melted electrospun meshes were prepared by treating meshes at 80° C. for 1 minute followed by quenching to collapse the porous structure on itself. This procedure was done quickly to prevent phase separation of PCL and PGC-C18, which was confirmed by differential scanning calorimetry (DSC) and consistent with their similar structures. Electrospun meshes and melted electrospun meshes for PCL and 10% doped PGC-C18 PCL were compared using SEM and showed that the melted meshes have a comparably smooth surface.

The surface roughness of single electrospun fibers was quantified for PCL and PCL doped with 10% PGC-C18 using AFM. Electrospun fibers showed a finite surface roughness (RMS≈50 nm) with consistent RMS values between fibers with different PGC-C18 doping concentrations. This finite roughness indicates that both intrafiber and interfiber roughness may contribute to high apparent contact angles. The melted electrospun meshes afforded a lower maximum contact angle of 116° with 50 wt % doping of PGC-C18. Solvent cast films of the polymers possessed contact angles similar to the melted electrospun meshes ($\Theta_{max}$=111°). Surface area measurement using Kr BET on the electrospun and melted electrospun meshes showed that electrospun meshes possess at least 30× more surface area than the melted counterparts. Electrospun mesh surfaces with <25% PGC-C18 doping could be pushed into the stable Wenzel regime by dropping the water droplet used in contact angle measurements from 2 feet. Electrospun meshes with >25% PGC-C18 doping could not be pushed into the Wenzel regime in this way, indicating that 25% doping is an approximate boundary condition for the Wenzel-to-Cassie state transition.

Example 17: Tunability of Polymer Wett-Ability Using a Hydrophobic Doping Agent

Solvent-cast poly(caprolactone) films were prepared containing 0-75 wt % poly(glycerol monostearate-co-caprolactone). The polymers were co-dissolved in dichloromethane (10 w/v %) and films were cast onto glass substrates. Contact angle measurements were obtained as a measure of hydrophobicity/wet-ability of the polymer. The contact angle ranged from ~83° for films composed solely of poly(caprolactone), and increased up to a maximum of 111° when blended with at least 10% poly(glycerol monostearate-co-caprolactone).

Example 18: Poly(Caprolactone) Porous Coatings with and without a Hydrophobic Doping Agent can be Coated on Varied Material Type This 3D superhydrophobic electrosprayed coating technique is a substrate generic approach to coat structurally and compositionally different materials such as collagen, cotton fabric, nitrile rubber, and aluminum foil. After electrospraying onto these surfaces, the resultant contact angle of all four surfaces is >167° (hysteresis<7°), whereas the uncoated portions of the material are easily and quickly wetted. Materials which are electrically insulating, such as glass, can be coated with the use of conductive copper tape near the material surface to ground the current used in the electrospraying process.

Example 19: Layer-by-Layer Poly(Caprolactone) Meshes and Poly(Caprolactone) Meshes The 3D nature of electrospun superhydrophobic materials can be further utilized by creating layered meshes so that each layer's polymer composition, thickness, and utility can be varied. Layered meshes were created with a 90-µm core of PCL alone and with 150-µm PGC-C18 layers above and below.

Example 20: Stimuli Responsive Polymer Wettability Using Ultraviolet Light Activated Hydrophobic Doping Agent: Hydrophobic to Hydrophilic Transformation A poly(glycerol-co-ε-caprolactone) (1:4) (PGC) polymer was synthesized following a previously published protocol[23], and 12-(1-(2-nitrophenyl)ethoxy)-12-oxododecanoic acid (C12-NPE) was attached to the free hydroxyl of the PGC through an ester linkage using a DCC coupling method. The UV active polymer, poly(glycerol 12-(1-(2-nitrophenyl)ethoxy)-12-oxododecanoic acid-co-caprolactone) (PGC-C12-NPE; 20,000 g/mol; PDI=1.63), was dissolved in a 5:1 chloroform:methanol solution with poly(ε-caprolactone) (PCL) (70,000-90,000 MW, Sigma) at a 3:7 weight ratio. The resulting polymer solution, at 10% by weight, was electrospun using the following parameters: the solution was flowed through a 20 gauge needle at 3 mL/hour and a 10 kV potential was applied between the needle and a rotating and translating collecting drum 10 cm away.[24-25] The electrospun mesh was analyzed using a Zeiss SUPRA 55VP field emission scanning electron microscope (SEM) to identify micrometer (~3-5 µmbeads) and nanometer (fiber diameters ~100-150 nm) scale textures on the surface.

Figure 4:
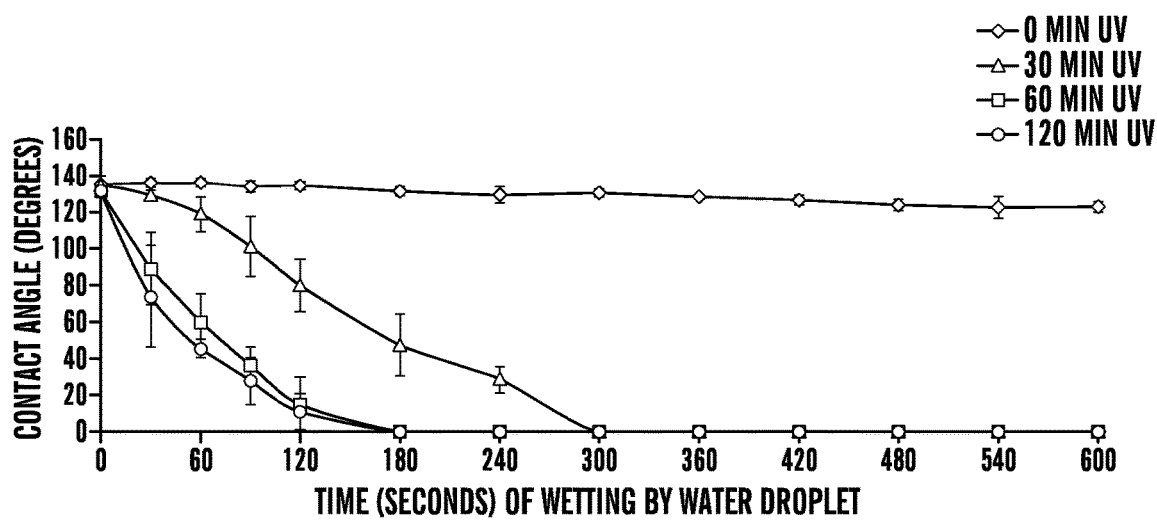
FIG. 4 demonstrates that a UV dose dependent wetting profile was observed with smaller UV doses wetting more slowly over time compared to larger UV doses (5.4 J/cm2 vs. 10.8 J/cm2 for 30 minutes and 60 minutes of UV exposure, respectively). With as little as 15 minutes of UV exposure, the ACA decreased substantially over 600 seconds compared to the unexposed control meshes (ACA ~20° vs ~135'). Doubling the UV exposure time to 30 minutes resulted in more consistent ACAs and a fully wetted surface (ACA ~0°) within 300 seconds. Maximum wetting rates were achieved with UV exposure times greater than 60 minutes where the meshes fully wetted within 150 seconds. For all UV exposure times greater than 30 minutes, the change in ACA from the native mesh was statistically significant after 120 seconds of wetting ($p<0.05$).
Figure 4:
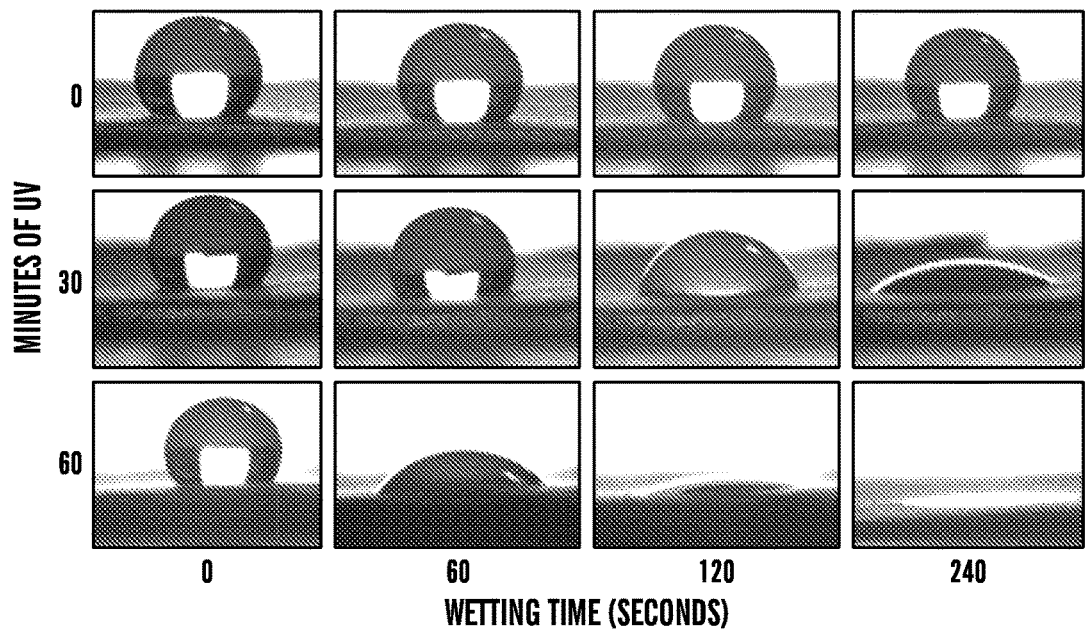

A series of ~80 µm thick meshes were then exposed to UV light (λ=365 nm, Spectroline, Westbury, N.Y.) for 0, 15, 30, 60, 90, and 120 minutes. Contact angle measurements were performed with four microliter water droplets recorded at a 0.2 Hz frame rate on top of the meshes after each UV exposure time using a Kruss DSA100 contact angle goniometer. The photoactive electrospun PGC-C12-NPE mesh exhibited a UV induced transition from a hydrophobic material, with an apparent contact angle (ACA) of ~135°, to a hydrophilic material with an ACA of ~0° after various UV exposure times. A UV dose dependent wetting profile was observed with smaller UV doses wetting more slowly over time compared to larger UV doses (5.4 J/cm2 vs. 10.8 J/cm2 for 30 minutes and 60 minutes of UV exposure, respectively). With as little as 15 minutes of UV exposure, the ACA decreased substantially over 600 seconds compared to the unexposed control meshes (ACA ~20° vs ~135'). Doubling the UV exposure time to 30 minutes resulted in more consistent ACAs and a fully wetted surface (ACA ~0°) within 300 seconds. Maximum wetting rates were achieved with UV exposure times greater than 60 minutes where the meshes fully wetted within 150 seconds. For all UV exposure times greater than 30 minutes, the change in ACA from the native mesh was statistically significant after 120 seconds of wetting (p<0.05). Data are shown in FIG. 4.

Figure 5A:
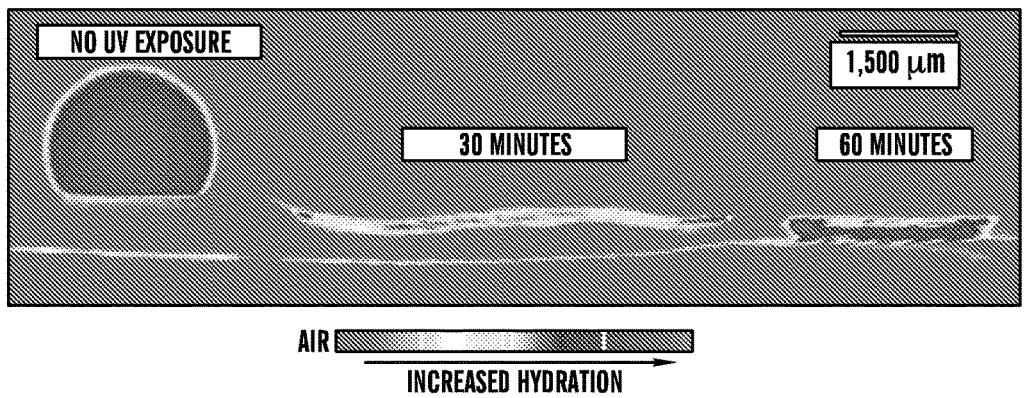
FIGS. 5A-5C depict cell patterning on stimuli responsive polymer using ultraviolet light activated hydrophobic doping agent. The utility of the poly(glycerol 12-(1-(2-nitrophenyl)ethoxy)-12-oxododecanoic acid-co-caprolactone) photoinduced wetting method to print 3D hydrophilic cavities surrounded by hydrophobic regions for controlled cell patterning was evaluated. A circular photo mask (1590 μm in diameter) was used to create 3D hydrophilic cavities of various depths within the hydrophobic bulk material by varying the UV exposure time (FIG. 5A). If the mesh was not exposed to UV light the aqueous CT contrast agent solution was restricted to the surface of the hydrophobic mesh. In contrast, the aqueous solution penetrated into the cavities formed via photolysis. A linear relationship between the UV exposure time and the depth of the cavities was determined (FIG. 5B). A 150 μm thick mesh and a 1590 μm in diameter photomask was used to selectively expose a small circular region of the mesh to UV light and create a hydrophilic region. Using a live cell fluorescent stain and confocal microscopy, confocal images were generated which indicate there is a strong correlation between where the mesh wets (~2.7 mm in diameter cavities for 4 µL of liquid after UV exposure, according to the µCT data), and where the cells adhere to the UV exposed mesh (~2.7 mm in diameter cavities). In addition, the number of viable cells after 24 hours is greater for the mesh exposed to UV light compared to the mesh without UV exposure (FIG. 5C).
Figure 5B:
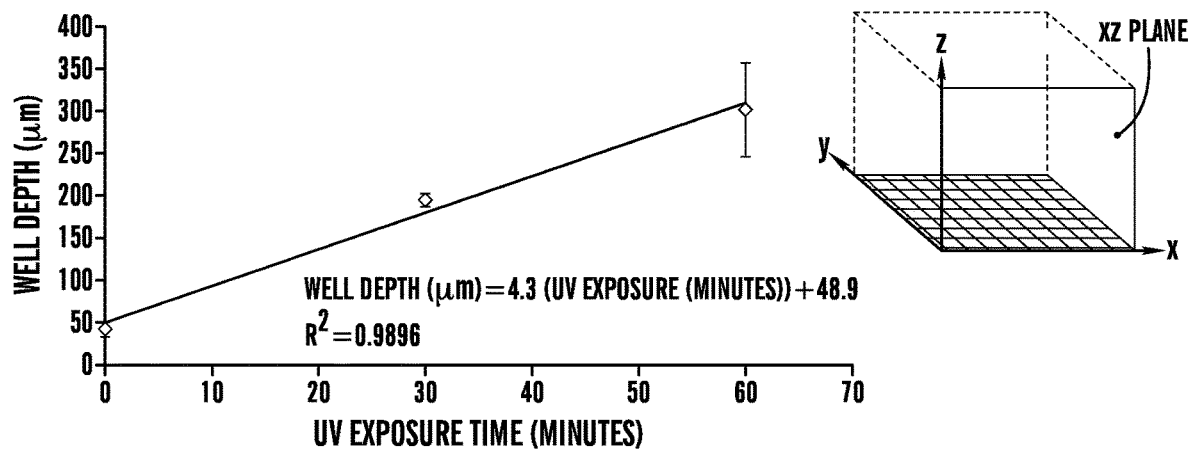
Figure 5C:
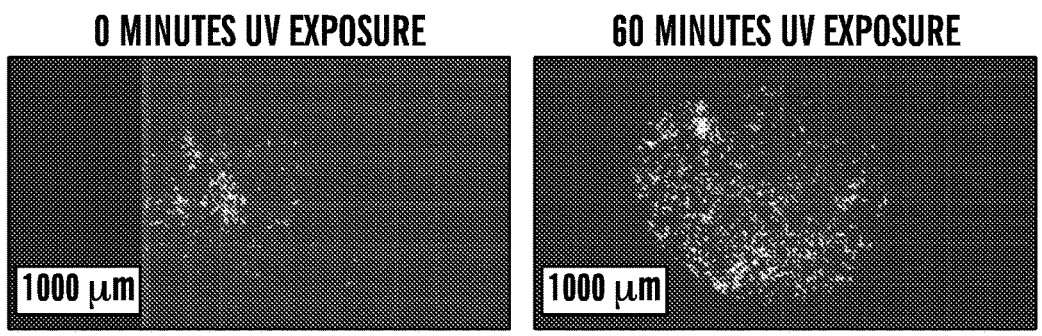

Example 21: Cell Patterning on Stimuli Responsive Polymer Using Ultraviolet Light Activated Hydrophobic Doping Agent: Hydrophobic to Hydrophilic Transformation We evaluated the utility of the poly(glycerol 12-(1-(2-nitrophenyl)ethoxy)-12-oxododecanoic acid-co-caprolactone) photoinduced wetting method to print 3D hydrophilic cavities surrounded by hydrophobic regions for controlled cell patterning. A circular photo mask (1590 µm in diameter) was used to create 3D hydrophilic cavities of various depths within the hydrophobic bulk material by varying the UV exposure time. Specifically, cavities of 194.2±8.2 µm and 301.1±55.7 µm depths were fabricated by exposing the photoactive meshes to UV light for 30 minutes and 60 minutes respectively. These hydrophilic regions were analyzed by applying a dilute solution of a water soluble CT contrast agent (VISIPAQUE™, 80 mg of iodine/mL, GE Healthcare) to the surface of the meshes and using an X-ray µCT scanner to measure the water penetration into the meshes. As shown FIGS. 5A and 5B, if the mesh was not exposed to UV light the aqueous CT contrast agent solution was restricted to the surface of the hydrophobic mesh. In contrast, the aqueous solution penetrated into the cavities formed via photolysis. A linear relationship between the UV exposure time and the depth of the cavities was determined.

One application for a material with tunable 3D hydrophobicity is selective cell patterning. Specifically, we determine whether a human breast cancer cell line (MCF7) would selectively adhere on either the hydrophobic or hydrophilic regions of the UV active meshes. As with the previous µCT experiments, we used a 150 µm thick mesh and a 1590 µm in diameter photomask to selectively expose a small circular region of the mesh to UV light and create a hydrophilic region. Using a live cell fluorescent stain and confocal microscopy, we generated confocal images which indicate there is a strong correlation between where the mesh wets (~2.7 mm in diameter cavities for 4 µL of liquid after UV exposure, according to the µCT data), and where the cells adhere to the UV exposed mesh (~2.7 mm in diameter cavities). In addition, the number of viable cells after 24 hours is greater for the mesh exposed to UV light compared to the mesh without UV exposure. The cells on the unexposed mesh are confined to a smaller area due to the reduced wetting associated with a fully protected mesh. Images were taken at several positions and depths to create a 3D montage of the meshes. This result is consistent with a number of previous studies demonstrating protein and cell patterning on, for example, flat 2D polystyrene, polydimethylsiloxane, glass, collagen, and gold coated surfaces.[26-30] Such patterned cell-polymer constructs are of potential interest for those conducting high throughput drug screening assays, studying cell-scaffold interactions, or studying the interactions between various cell types when arranged in predefined architectures.[31-33]

Example 22: Nanopore Fabrication and Drilling

Nanopore chips are fabricated from a <1,0,0> single-crystal silicon wafer through-etched to leave a thin (~20 nm) freestanding silicon nitride (SiN) membrane supported by a small (5 mm×5 mm×0.35 mm) silicon chip.

Figure 6:
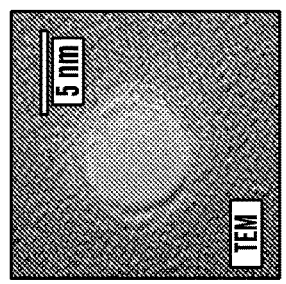
FIG. 6 depicts Tunneling Electron Microscope (TEM) image of nanopore taken after drilling.

A nanopore is drilled through the SiN using a highly focused transmission electron microscope beam ($10^8$-$10^9$ $e^-/nm^2$) to sputter away material from the thin membrane according our previously published method. A sample image of a pore is shown in FIG. 6. Nanopores are drilled and cleaned prior to electrospinning.

Example 23: Fabrication of a Nanopore-Nanofiber Mesh Device

Figure 7:
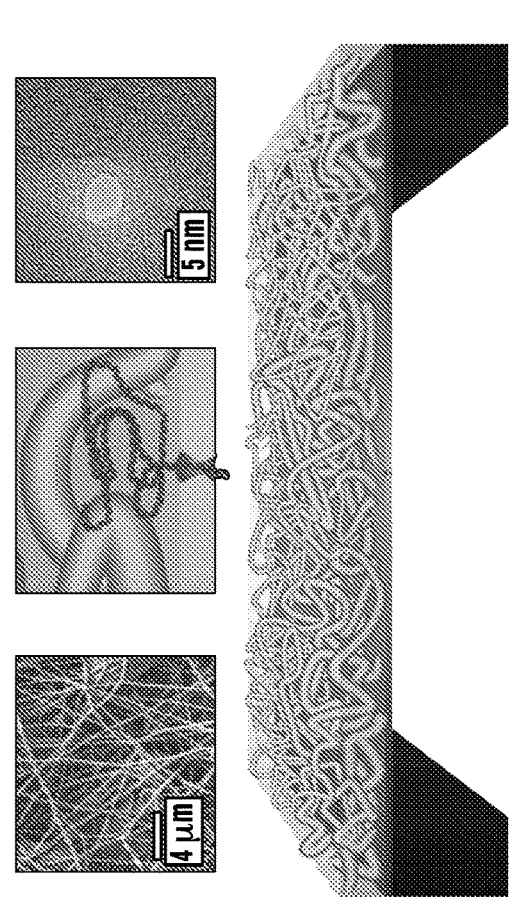
FIG. 7 depicts the nanopore-nanofiber mesh (NP-NFM) sensor Top (right to left): Panels show a scanning electron micrograph of the NFM, a close-up schematic of the mesh near the nanopore with DNA translocating, and a transmission electron micrograph of the nanopore. Bottom: Schematic depiction of a nanopore sensor coated with an electrospun polymeric nanofiber mesh (NFM).

We successfully fabricated fiber-coated nanopore devices by electrospinning a copolymer blend of poly(ε-caprolactone) (PCL) (70-90 kg/mol, Sigma) and poly(glycerol-monostearate-co-ε-caprolactone) (PGC-C18) (22 kg/mol) directly onto a nanopore chip. FIG. 7 shows a schematic of this device. FIG. 7 inset shows a typical SEM image of a 7:3 PCL:PGC-C18 hydrophobic NFM electrospun onto a NP chip, with fiber diameters ranging from 300-450 nm.

Figure 8:
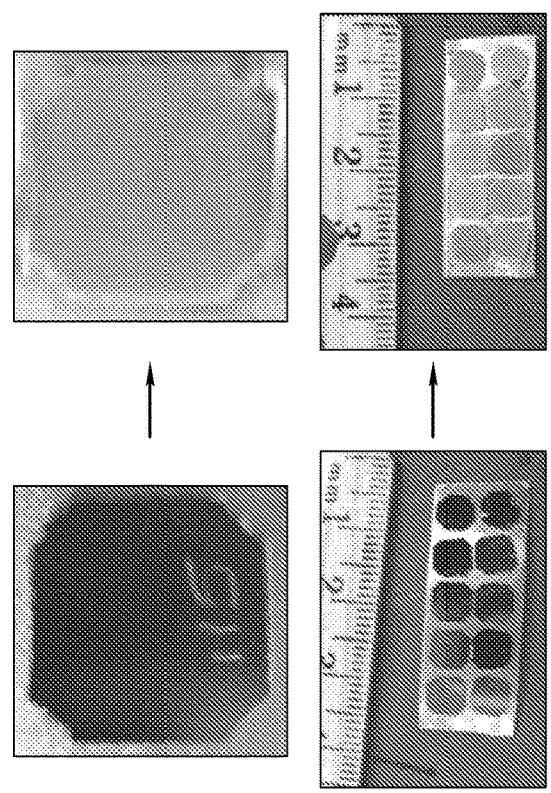
FIG. 8 depicts nanopore chips before and after electrospinning. images of nanopore chips before (left) and after (right) fabrication, showing parallelization of electrospinning technique. Up to 50 chips may be spun at once using our current apparatus.

We created devices using several co-polymer blends. The following co-polymer blends were created in 5:1 chloroform:methanol solutions: 7% by wt. poly(ε-caprolactone) (PCL) (70,000-90,000 MW, Sigma) (PCL alone solution), 7% by wt. PCL+0.78% by wt. PGC-C18 (9:1 PCL:PGC-C18 blend), 7% by wt. PCL+1.75% by wt. PGC-C18 (8:2 PCL:PGC-C18 blend), 7% by wt. PCL+3% by wt. PGC-C18 (7:3 PCL:PGC-C18 blend), 7% by wt. PCL+4.66% PGC-C18 (6:4 PCL:PGC-C18 blend), 7% by wt. PCL+7% by wt. PGC-C18 (5:5 PCL:PGC-C18 blend). The electrospinning parameters were modified from a previous publication based on PCL. The procedure was modified to produce nano-fibers (~300 nm) using a 3 ml/hour flow rate, a 8 kV source, a collector distance of 10 cm, and a 20 gauge needle for all electrospun NFMs. To electrospin polymer onto the devices, the SiN nanopore chips were affixed to one side of a double sided copper tape and the other side was adhered to the grounded collecting surface. NFMs were electrospun for the appropriate time for each blend such that 5 mg of polymer was electrospun onto the grounded collector (FIG. 8). A summary of some of the electrospinning parameters can be found in Table 3.

TABLE 3

| | PCL:PGC-C18 copolymer blend ratios | | | | | |
|---|---|---|---|---|---|---|
| Polymer blend | PCL alone | 9:1 | 8:2 | 7:3 | 6:4 | 5:5 |
| PCL weight | 7% | | | | | |
| PGC-C18 weight | 0 | 0.78% | 1.75% | 3.00% | 4.67% | 7.00% |
| Applied potential | 8 kV | | | | | |
| Grounded collector distance | 10 cm | | | | | |

TABLE 3-continued

| Polymer blend | PCL:PGC-C18 copolymer blend ratios | | | | | |
|---|---|---|---|---|---|---|
| | PCL alone | 9:1 | 8:2 | 7:3 | 6:4 | 5:5 |
| Needle gauge | 20 gauge | | | | | |
| Flow rate | 3 mL/hr | | | | | |
| Electrospinning time | 85 seconds | 78 seconds | 69 seconds | 60 seconds | 52 seconds | 43 seconds |

Example 24: Characterization of Electrospun Mesh Morphology on NP-NFM Devices

Doping PCL with increasing quantities of the hydrophobic PGC-C18 increases the resulting mesh hydrophobicity, as characterized by water droplet contact angle. These measurements of hydrophobicity indicate changes in chemical composition. A Kruss DSA100 contact angle goniometer was used to quantify the contact angles of water (4 µl) on the surface of the hybrid NP-NFM devices. Each water droplet was allowed to reach its equilibrium contact angle over 15 seconds before the water contact angle was measured.

Figure 9A:
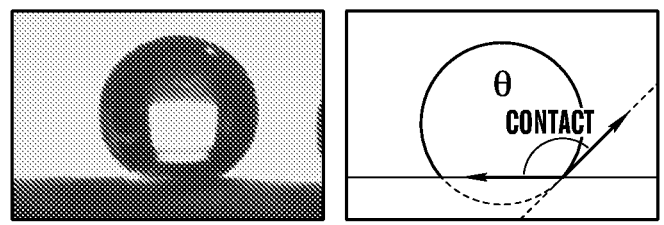
FIGS. 9A-9B Contact angle characterization of NFM hydrophobicity.
Figure 9B:
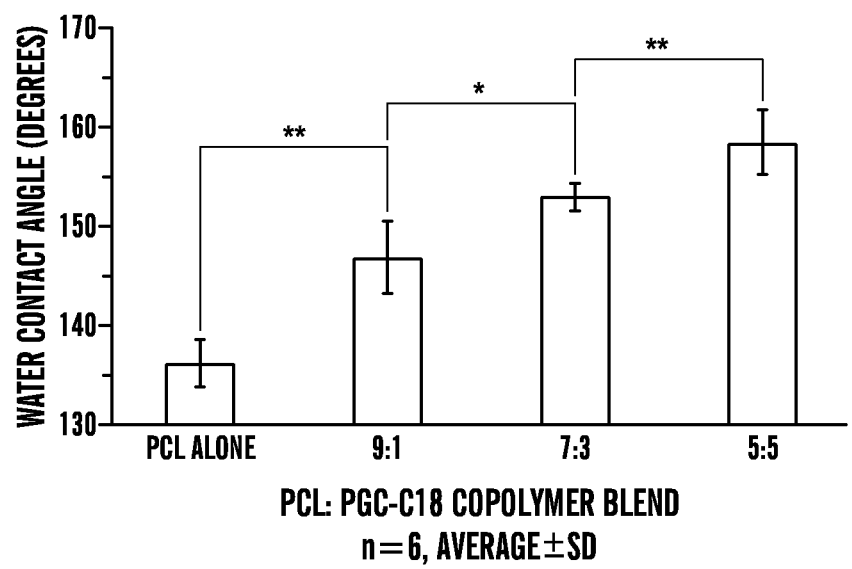

To quantify mesh hydrophobicity, a family of hydrophobic meshes composed of PCL doped with the stearic acid modified PGC (PGC-C18; 21,000 g/mol; PDI=1.73) was prepared at three doping concentrations (10%, 30%, 50% PCG). The apparent contact angle for these meshes, shown in FIG. 9A-B, increases from 136° for the PCL only mesh to nearly 160° for the 5:5 PCL:PGC-C18 mesh. Two of these, the 7:3 and 5:5 blends, may be categorized as super-hydrophobic (contact angle)>150°. All are much greater than the contact angle of 116° measured for a smooth cast film surface.

Figure 10:
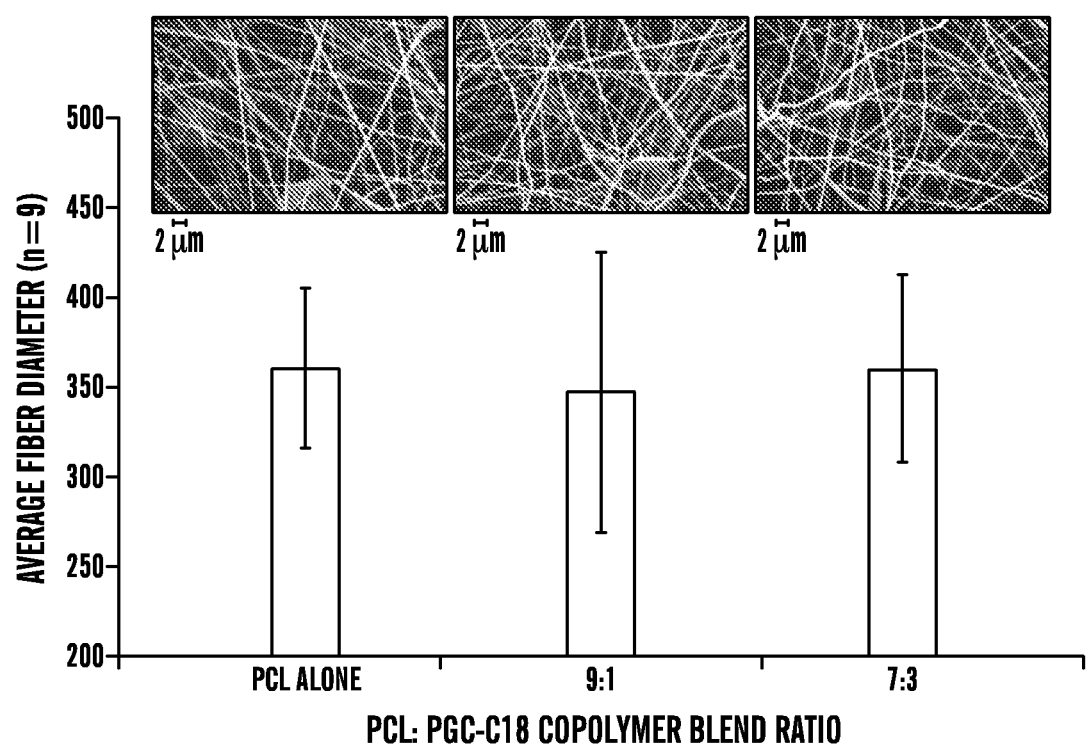
FIG. 10 depicts SEM images of three selected NFM copolymer blends with a constant PCL weight %. PGC-C18 content does not affect the physical properties (fiber diameter, mesh density, etc.) of the NFM. Fiber diameters for each blend range from ~250-450 nm. Representative fibers were chosen at random for each NFM copolymer blend. (Scale: 2 µm. Magnification: 2,500×. n=9, Avg±StDev, p>0.05 comparing each copolymer blend).
Figure 11:
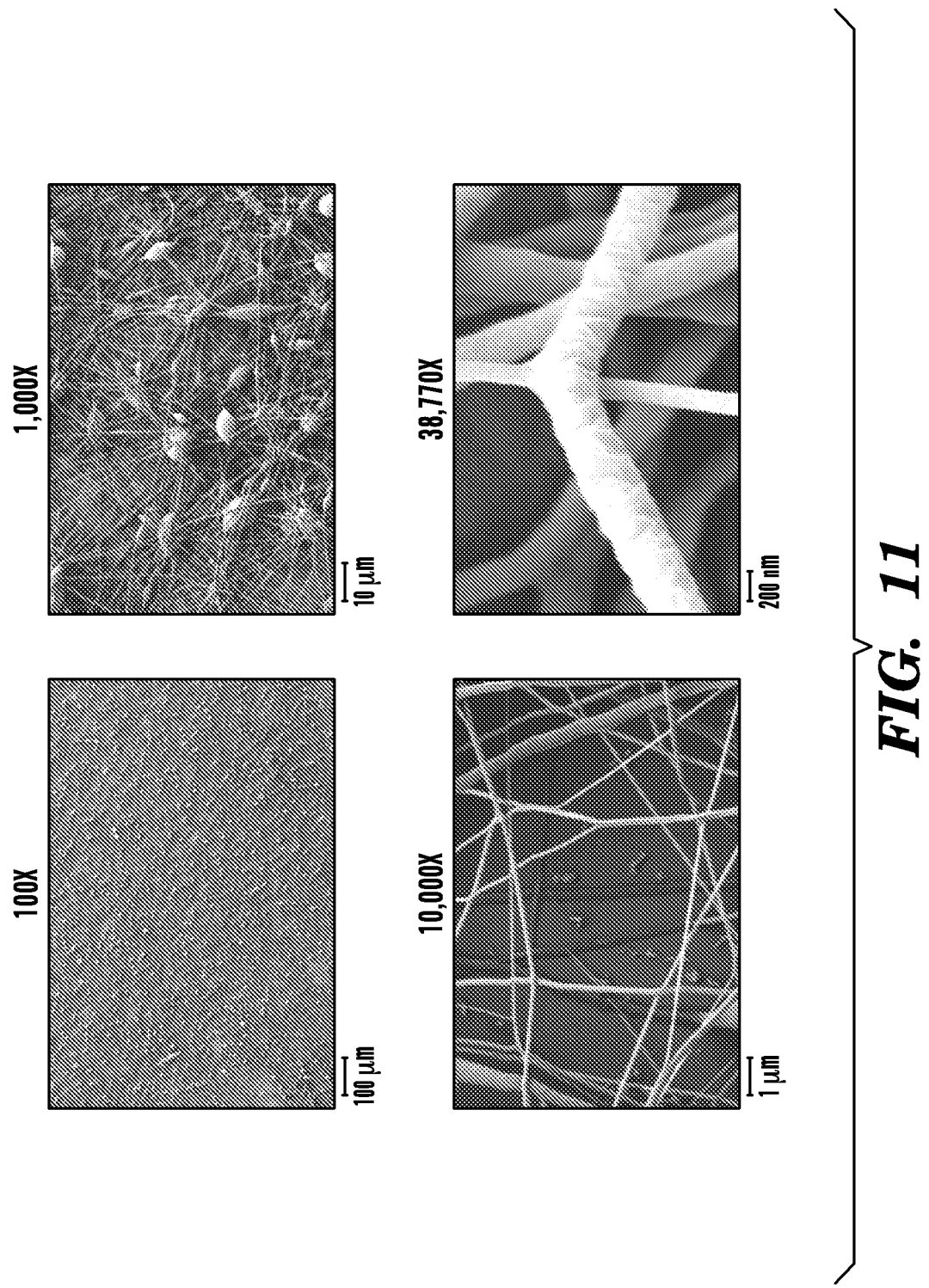
FIG. 11 depicts SEM images of a 7:3 PCL:PGC-C18 NP-NFM devices at 100×, 1,000×, 10,000×, and 38,770×. The scale bars are 100 µm, 10 µm, 1 µm, and 200 nm for the 100×, 1,000×, 10,000×, and 38,770× images, respectively. All NFM copolymer blends produce similar fiber diameters and bead morphology. Both micrometer and nanometer scale texture is produced by the NFMs allowing for the enhanced hydrophobicity. The SiN membrane is visible below approximately 3-4 layers of nanofibers (10,000× image) making the NFM approximately 1-2 µm thick.

In all cases the electrospinning deposition time, voltage, and needle position were adjusted to produce uniform NFM thicknesses with fibers of similar morphology across all polymer blends (FIG. 10, 11). A Zeiss SUPRA 55VP field emission SEM was used to image the surfaces of each NP-NFM. The samples were affixed to an aluminum sample stub using copper tape and were coated with 5 nm of Au/Pd prior to imaging and imaged at an accelerating voltage of 2 kV.

Example 25: Electrical Characterization of a Nanopore-Nanofiber Mesh Sensor

It is crucial to characterize the electrical properties of the modified nanopore as compared to a bare nanopore to ascertain that our NFM modification is indeed orthogonal to nanopore sensing. We measured noise and conductivity in representative NP-NFMs, and found that their characteristics were nearly indistinguishable from bare nanopores. We conclude that this device has successfully incorporated the NFM without changing the inherent electrical behavior of the nanopore.

NP chips were sealed in a custom-built flow cell permitting a low-noise recording of the ion current flowing through the pore. Nanopore chips are assembled in a Teflon cell and PDMS is used to seal the edges of the chip to prevent current leakage. Reservoirs on each side of the membrane are filled with an electrolyte buffer (1M KCl, 10 mM Tris-HCl) and all bubbles are removed manually. The NFM coating may be hydrated using 5% ethanol, if necessary, which may then be rinsed out with a 10× buffer exchange. An Axon 200B amplifier is used to apply a voltage clamp (~300 mV) across the membrane via Ag/AgCl electrodes, and the resulting current is measured.[35]

All data are collected using National Instruments A/D data acquisition boards and custom Labview software at a rate of 250 kHz, filtered at 100 kHz (unless otherwise specified). Conductance is calculated by measuring current as a function of voltage for −500 mV to +500 mV. The electrolyte buffer used in this study was 1M KCl, 10 mM Tris-Cl, pH 7.5. Typical applied bias for translocations is 300 or 500 mV. Electrical noise is measured both as RMS noise for each voltage applied, and also as a frequency-domain spectrum transformed from a continuously recorded current trace. Only NP-NFM devices that displayed voltage response and noise characteristics very similar to an uncoated nanopore were used in this study.[35]

Noise power spectra were collected for a bare nanopore, a PCL-only-coated nanopore, and a 7:3 PCL:PGC-C18-coated nanopore. Data was acquired at an applied bias of 300 mV at a rate of 250 kHz, and was filtered at 100 kHz. All nanopores were 4 nm in diameter as measured via TEM.

The three power spectra are nearly identical, indicating that the NFM does not significantly change the background current noise in a solid-state nanopore. Note that the red and blue spectra are for the same pore on different days, while the green spectrum is a different nanopore of the same size (hence the slightly different shape to the curve).

Figure 12:
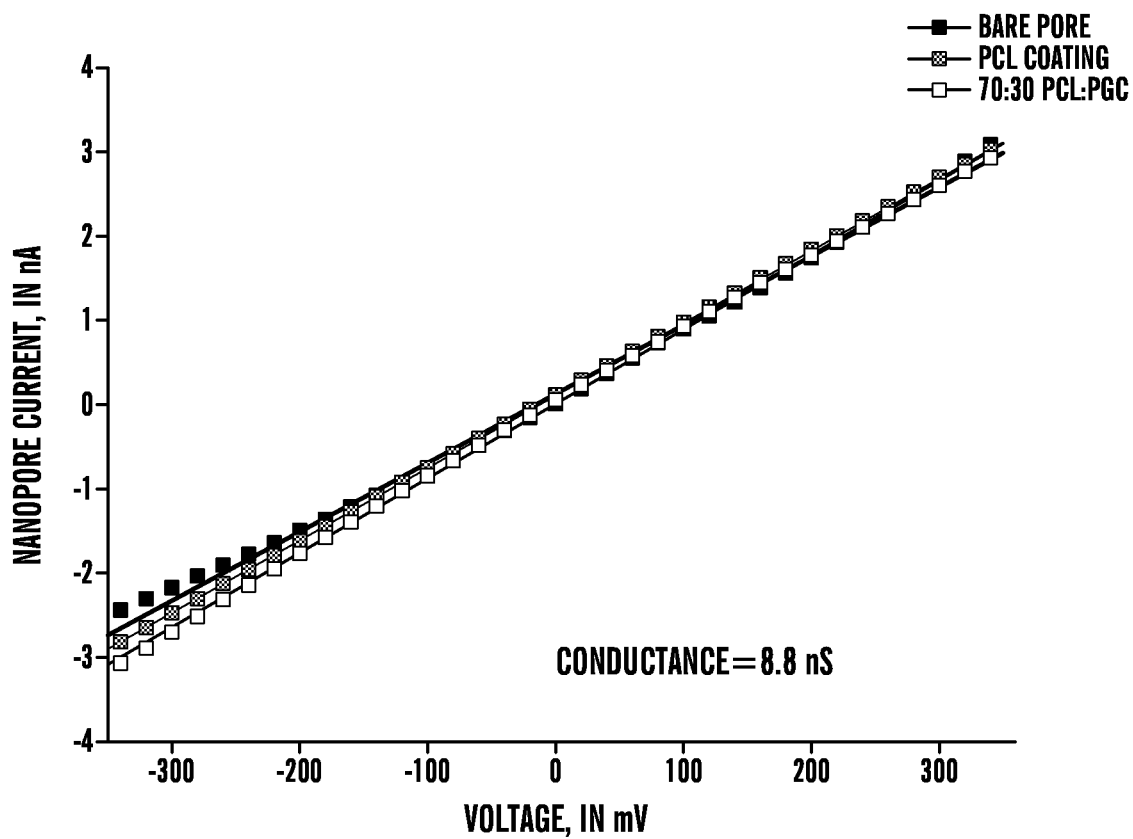
FIG. 12 depicts I-V curves for coated and uncoated nanopores. I-V curves for a 4 nm nanopore in 1M:1M KCl, with three different NFM coating conditions: bare (blue), PCL only (green), and 7:3 PCL:PGC-C18 (red). Data collected at 250 kHz, filtered at 100 kHz.

We next checked NP-NFM conductivity compared to a bare pore to ensure that the addition of an NFM does not significantly affect nanopore voltage response. FIG. 12 shows I-V curves for the same three nanopores (bare nanopore, a PCL-only-coated nanopore, and a 7:3 PCL:PGC-C18-coated nanopore) between −500 mV and +500 mV relative to the grounded cis chamber. As with noise, the conductance of the nanopore (~9 nS) does not appear to be affected by either NFM.

Example 26: DNA Translocations and Sample Exchange in a Nanopore-Nanofiber Mesh Sensor In addition to checking that the NP-NFM had electrical responses nearly identical to those of a bare nanopore, we also demonstrated that it could detect translocations of DNA. We expected that while the addition of an NFM might affect translocation dynamics, it should not fundamentally change the resistive sensing capability of the pore. Indeed, we found that the NP-NFM sensor readily detected transient blockades in current due to the passage of DNA. Furthermore, the NP-NFM did not exhibit detectable non-specific binding that might complicate sample change via serial dilution and buffer replacement.

Figure 13:
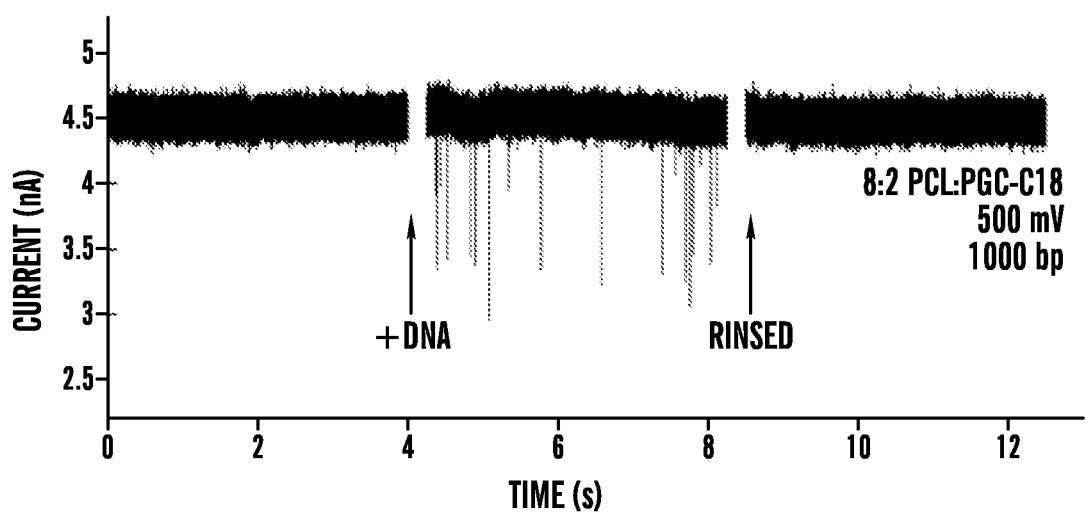
FIG. 13 depicts current traces for DNA in an NP-NFM at 500 mV. These continuous current recordings for an NP-NFM (8:2 PCL:PGC-C18) initially show a clean pore with a steady open pore current of ~4.5 nA. After adding 1000 bp DNA, transient drops in current indicate the passage of individual molecules through the nanopore. The DNA was rinsed out with a 10× wash, returning the current trace to its original clean and open state. Data was collected at 500 mV in a 1M:1M KCl buffer, pH 7.5. Current was recorded at 250 kHz and filtered at 100 kHz.

FIG. 13 shows a continuous current trace of DNA added to the cis side of an NP-NFM device with an 8:2 PCL:PGC-C18 electrospun mesh. First, under an applied electric potential of 500 mV, a clean current trace is obtained from a 4 nm nanopore. Adding ~1 nM 1000 bp DNA into the cis chamber induces transient blockades in the ionic current corresponding to translocations of DNA from the grounded cis side to the positively biased trans side of the membrane.[35]

Upon rinsing the nanopore 10× with buffer (no additional DNA), the nanopore current was returned to its original clean state, with no transient blockades. This demonstrates that the NP-NFM can detect the presence of DNA in the same manner and at the same concentrations as a bare nanopore. Additionally, the NP-NFM may be cleared of one sample using the same wash protocol as for a bare nanopore, confirming that multiple samples may be used in succession in the NP-NFM without cross-contamination.

Example 27: Translocation of dsDNA Through an NP-NFM

While the NP-NFM detects transient blockades as well as a bare nanopore, we observe that a novel finding. Specifically, we note that while the current blockage level appears to be unaffected by the presence of an NFM, the overall translocation times are significantly longer.

Figure 14A:
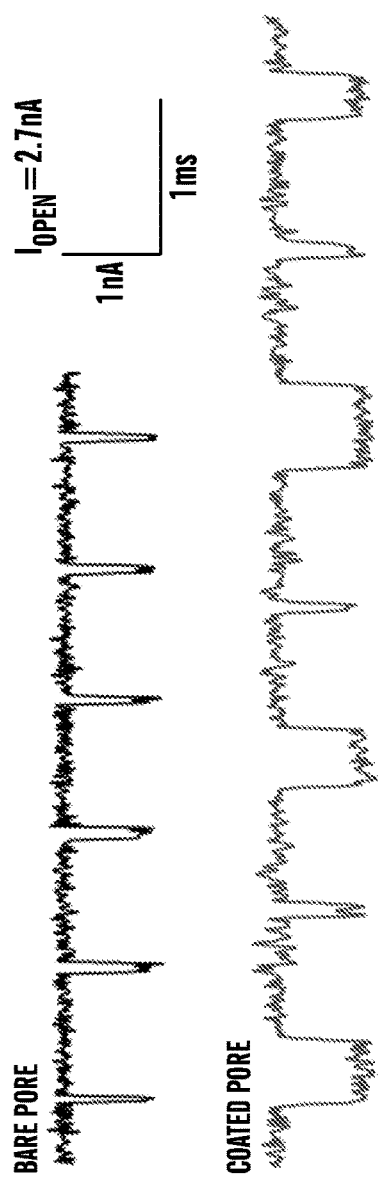
FIGS. 14A-14B depicts a comparison of translocations in bare pore vs. NP-NFM.

FIG. 14A shows sample translocations collected for a bare nanopore (blue) and the same nanopore coated with a 7:3 PCL:PGC-C18 NFM (red). These events are characterized by duration ($t_T$) and relative current blockage level ($I_B$). Thousands of translocations were collected for each nanopore condition. Current levels for individual events are determined using Gaussian fits to all-points histograms. Overall open pore current, conductance changes, blockage levels, and so forth are fits to ensemble histograms. The overall population characteristics may be observed on the event diagram (scatter plot).

Figure 14B:
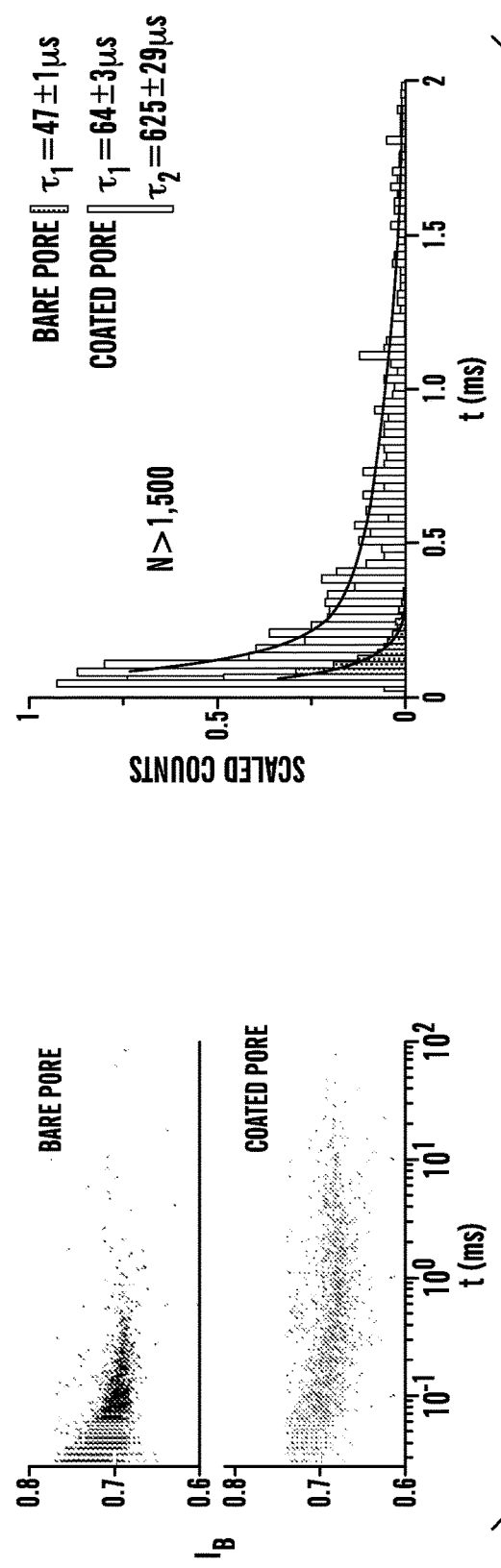

Dwell time is characterized in FIG. 14B: distributions for translocation time, $t_T$, represent the tail of a Poisson-like distribution and are characterized by the timescale of an exponential decay fit. Where multiple populations could be distinguished, this fit used two terms, one for "normal" translocations, and one for "slowed" translocations, weighted for counting error. A typical $r^2$ value is 0.9 or higher for both types of fits.

First, and most noticeably, FIG. 14 shows a broader spread in the DNA translocation time for the NP-NFM as compared to the bare nanopore. Specifically, the dwell-time of a large fraction of the events falls between 0.5 ms and 10 ms (FIG. 14B); a range which exceeds the typical translocation time of the same uncoated pore by roughly an order of magnitude.

A closer evaluation of the translocation events (see sample events in FIG. 14A and the dwell time histograms in FIG. 14B suggests that instead of a uniform shift of the entire dwell time histogram towards longer timescales, the NFM induces a bimodal distribution containing populations of "normal" and "long" events. Indeed, a mono-exponential tail fit fails to represent the dwell time histogram of the NFM coated pore as accurately as does a double exponential fit. The shorter timescale, $\tau_1$, is close to the typical timescale for the uncoated pore, while the longer timescale, $\tau_2$, is nearly 10× longer.

Second, we note from both the sample events in FIG. 14A and the scatter plot in FIG. 14B that the presence of the NFM does not substantially affect the open pore current (the ion current prior to DNA entry into the pore) or the blocked current level. Since blockage level is the result of a drop in conductivity when DNA physically blocks the pore, and because prior results had indicated that the conductivity of the nanopore was unaffected by the NFM, this data confirmed our expectation that the blockage level would also not be affected by the NFM.

Example 28: Current Blockage Level During Translocation of dsDNA does not Depend on Mesh Composition Our next step was to expand the family of NP-NFM devices to determine whether the changes in translocation dynamics that we had observed for the 7:3 PCL:PGC-C18 mesh were influenced by changes in mesh chemical composition. To further characterize the nature of the slowed DNA translocations induced by the presence of a tunable NFM, we expanded the family of NP-NFM devices to include six different PCL:PGC-C18 copolymer blends spun onto 4-4.5 nm pores. All observations were referenced to a bare nanopore.

Figure 15:
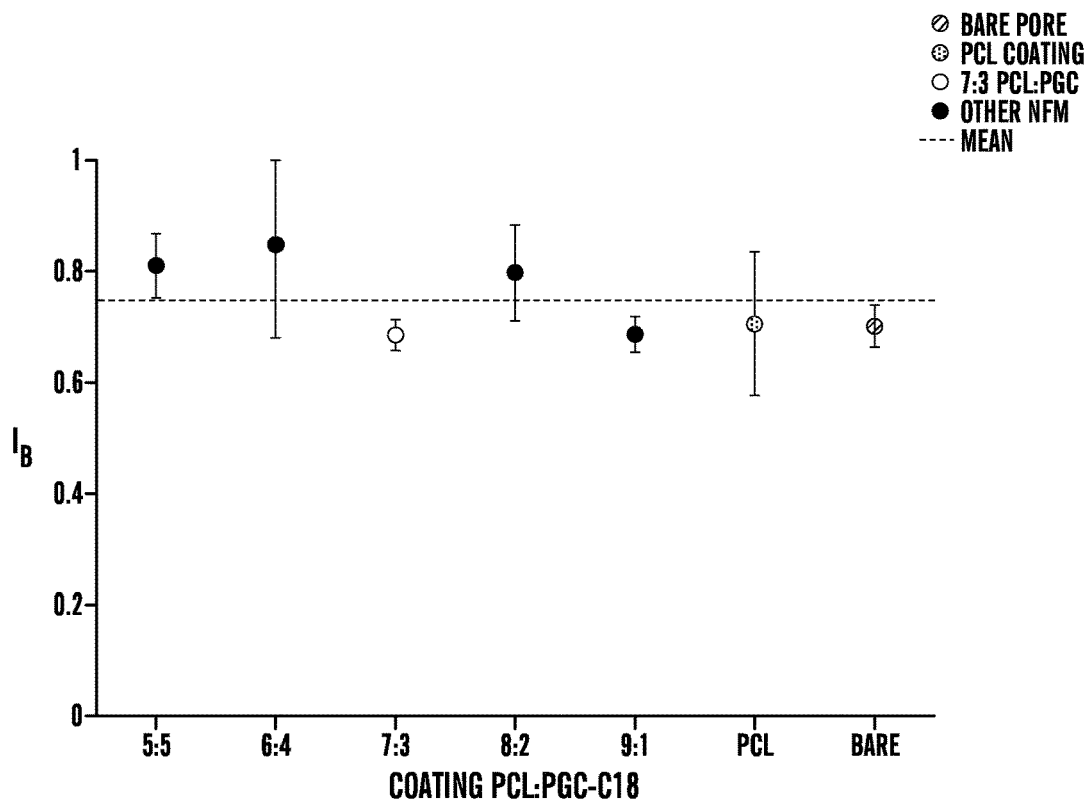
FIG. 15: depict current blockage level for NP-NFM with varying chemical composition. Current blockage level IB for: Bare pore, PCL only, 9:1, 8:2, 7:3, 6:4, and 5:5 PCL:PGC-C18 blends. All data are for 1000 bp dsDNA in 4-4.5 nm nanopores at 300 mV (error bar: τ±95% fit confidence interval for Gaussian current level fits. Red, green, and blue pores correspond to the same experiments used in FIG. 12).

Similar to our observations for the 7:3 copolymer blend, the relative blockage level ($I_B=I_{block}/I_{open}$) and the open pore conductance measured are nearly the same across all of these compositions (FIG. 15). These results suggest that ion mobility near the NP in each of these meshes is similar to that of a bare NP, consistent with the results described above for the 7:3 copolymer blend.

Example 29: Translocation Time Depends on NFM Chemical Composition

In contrast to the ion current levels, we found that dsDNA translocation dynamics in an NP-NFM sensor are highly dependent on the NFM chemical composition. We measured the characteristic translocation times of 1000 bp dsDNA using different NFM copolymer blend coatings, once again tail-fitting the resulting dwell-time distributions to double exponential functions.

Figure 16:
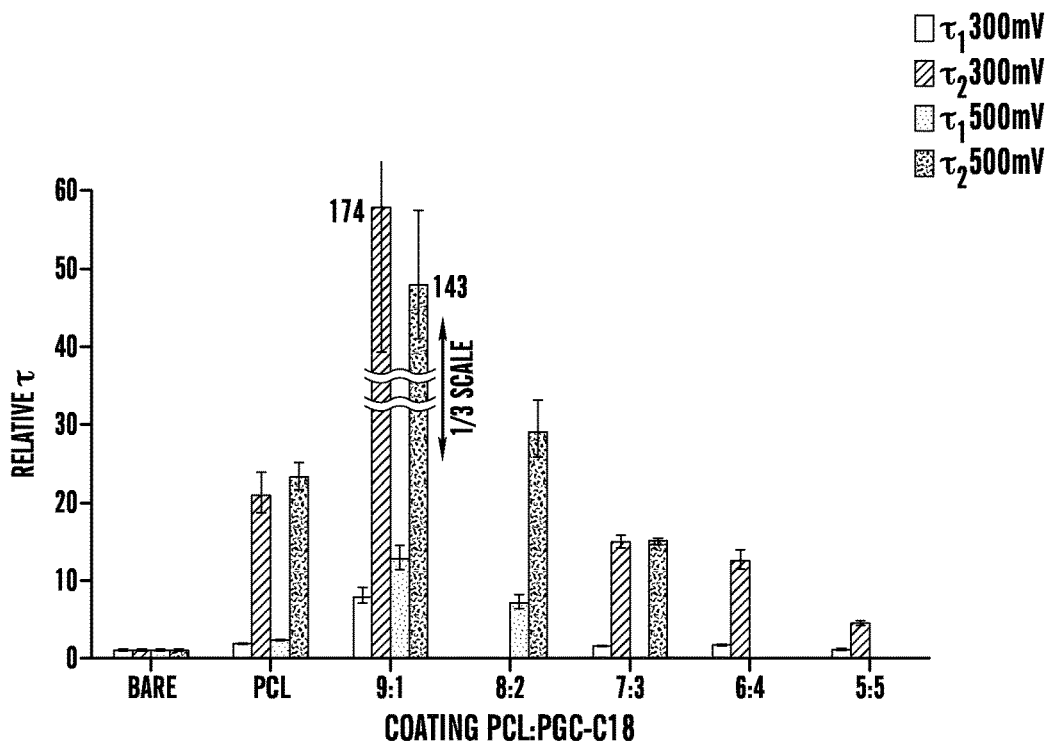
FIG. 16 depict relative slowing factor for translocations in NP-NFM of various chemical composition. Slowing factor $\tau_{relative}$ (where $\tau_{relative}=\tau_{coated}/\tau_{bare}$) for various coatings: Bare pore ($\tau_{relative}=1$), PCL only, 9:1, 8:2, 7:3, 6:4, and 5:5 PCL:PGC-C18 blends. All data are for 1000 bp dsDNA in 4-4.5 nm nanopores, 300 mV (blue) and 500 mV (red) (error bar: τ±95% fit confidence interval of exponential tail fits; 9:1 PCL:PGC-C18 blend at both 300 and 500 mV is shown at ⅓ scale for clarity). $\tau_{relative}$ values calculated using either $\tau_1$ or $\tau_2$ are indicated by light and dark colors, respectively.

We defined the relative $\tau$ as the ratio of the timescale for the "long" event population ($t_2$) at each coating normalized by the characteristic timescale of translocation in the bare pore. We repeated these measurements at two applied voltages: 300 mV and 500 mV. Our results are summarized in FIG. 16. Error bars show corresponding 95% confidence intervals for fits). For reference we also show the relative short $\tau$ values using the normal translocation population ($t_1$) where available, generally showing a value near unity.[35]

When the NFMs are ranked in order of increasing hydrophobicity according to contact angle measurement, we observed non-monotonic changes in relative $\tau$: The most- and least-hydrophobic NFMs, respectively, had less effect on translocation speed than an intermediate blend. Nevertheless, PCL alone slowed translocations by more than 20× at both 300 mV and 500 mV. The superhydrophobic 6:4 and 5:5 PCL:PGC-C18 meshes only slowed DNA by 12× and 4×, respectively, at the lower driving force of 300 mV.

For intermediate copolymer blends, the data collected at both 300 and 500 mV clearly showed a more pronounced slowing effect than the most- and least-hydrophobic meshes. In particular, the 9:1 PCL:PGC-C18 NFM slowed translocations by more than 140× at 500 mV, and more than 170× at 300 mV. At 300 mV, nearly 20% of events for this mesh were longer than 10 ms. For comparison, <0.2% of events in the bare pore at 300 mV are longer than 10 ms.

Example 30: Slowing Translocation of Long DNA in a Nanopore

Figure 17A:
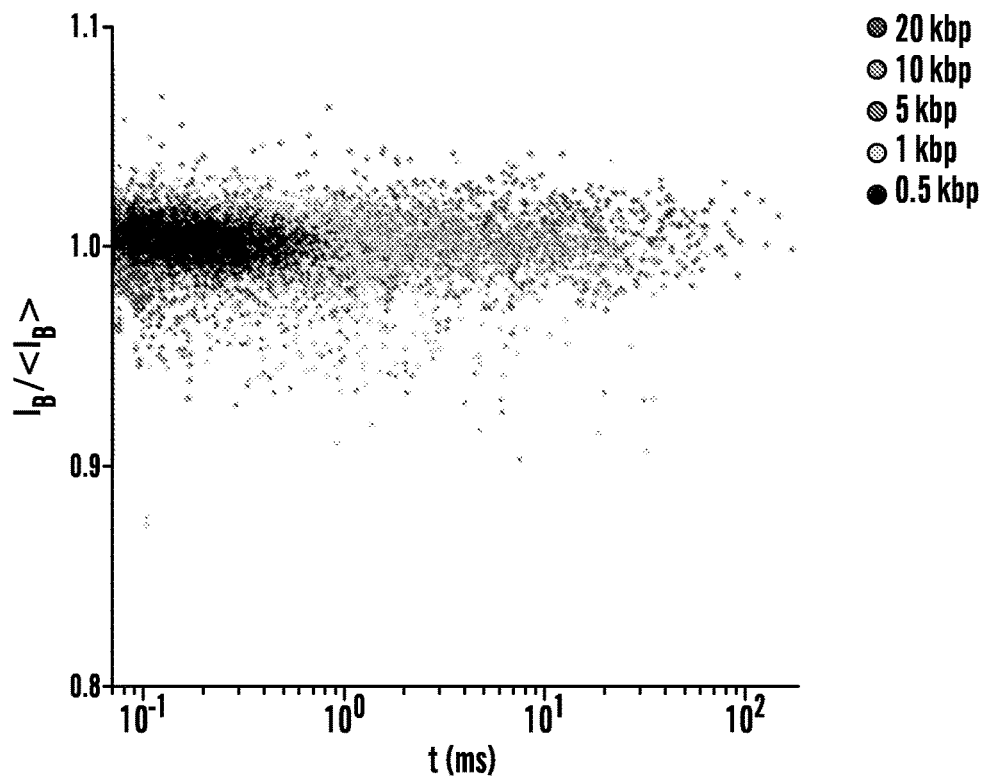
FIGS. 17A-17B depict event diagram for translocations of 0.5-20 kbp DNA.

Finally, we collected translocation events using the 7:3 PCL:PGC-C18 copolymer blend NFM, at 500 mV, for five different dsDNA lengths ranging from 0.5 kbp to 20 kbp to determine if longer biopolymers interacted more strongly with the NFM than shorter biopolymers. One might expect that the number of contact points between the mesh and DNA would increase with biopolymer length affording a more stable overall interaction. To maintain consistency across the samples, all measurements were performed sequentially in a single 6 nm diameter pore (with the same NFM coating), where some data sets were collected twice at different time points to ensure reproducibility. The characteristic ion current level and dwell time of each event was extracted and plotted on an 'event diagram' (FIG. 17). Events that displayed a folded DNA translocation pattern were excluded in the analysis to simplify interpretation of the results.

All DNA samples used in this study were double stranded DNA fragment length standards purchased from Thermo-Scientific (NoLimits 1000, 500, 5000, 10000, 20000 bp). DNA was stored in 50 mM KCl+TE buffer until use.

Figure 17B:
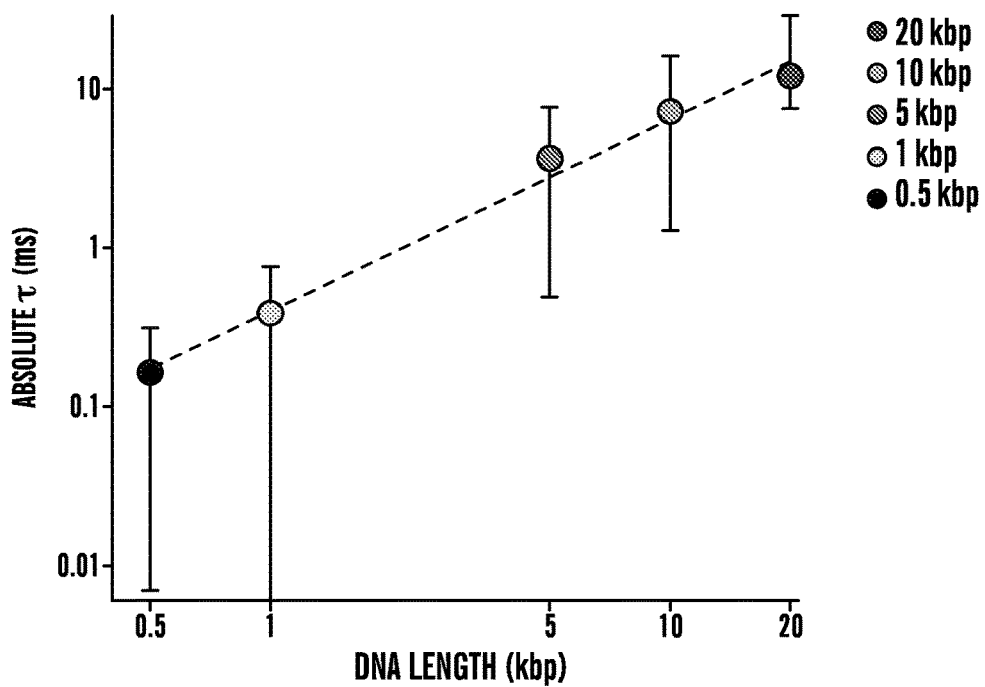
Figure 18A:
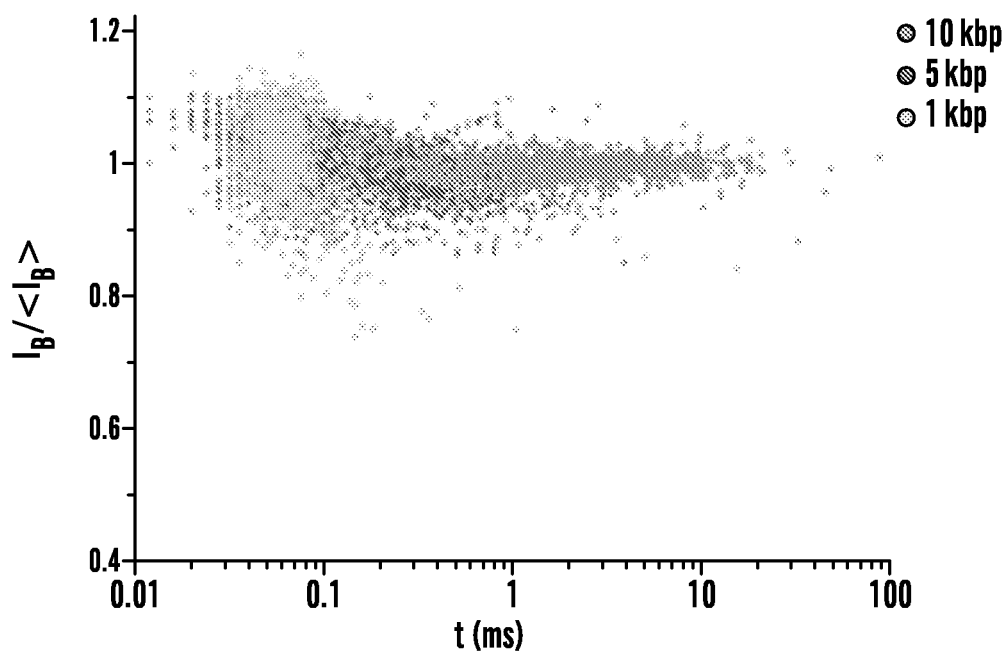
FIGS. 18A-18B depicts translocations of 1-20 kbp DNA in a bare nanopore.

FIG. 17 shows a clear pattern of longer translocation times with larger DNA molecules. While we did not make an attempt to discriminate collision events (fast events that involve unsuccessful threading of the DNA into the pore) from true translocations, the overall trend of the translocation time is clear and consistent for all lengths. As before, we numerically characterized the translocation dwell-time distributions using exponential tail fits. These results are shown in FIG. 17B, indicating mean translocation speeds of roughly 0.4-0.7 μs/base, which is 20-35× slower than for an uncoated pore under the same conditions (see FIG. 18). A monotonic growth in the characteristic translocation time as a function of length is observed for DNA in the presence of the NFM coating.

Figure 18B:
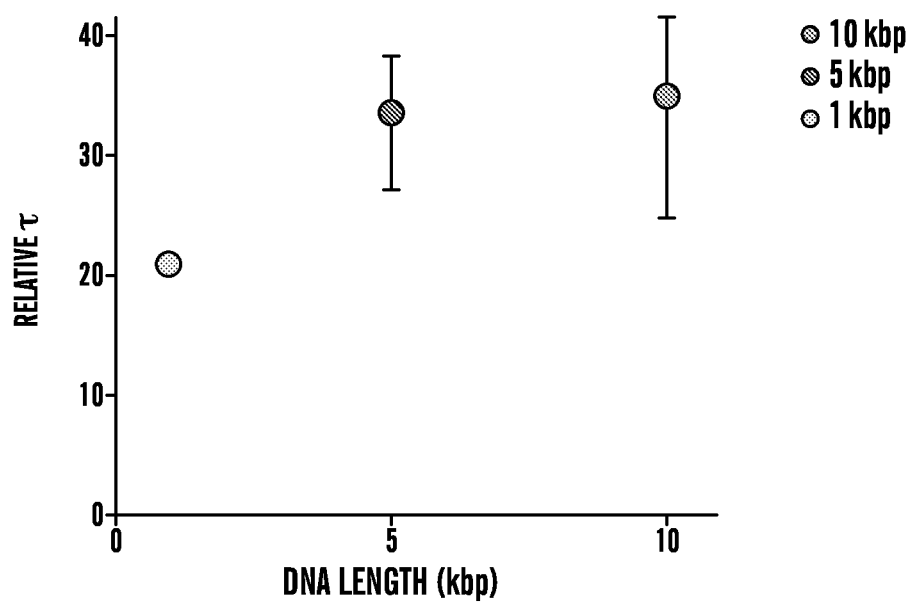

We also observed that in the range from 1 kbp to 10 kbp, the slowing factor relative to a bare pore increased slightly (from 20× to 35×, see FIG. 18B). While this is consistent with our original hypothesis, the trend of increased slowing for longer DNA was far less pronounced than expected, and barely significant given the associated fit error. Although this observation partly contradicts our a priori expectation that the longest DNA would be slowed much more than shorter DNA, there are still a number of possible explanations for this behavior. First, some of the events in the 20 kbp sample and even the 10 kbp sample exceeded the acquisition capability of our experimental system (~250 ms); thus the overall tail fit may reflect shorter timescales than expected. Second, a fully stretched 20 kbp DNA may extend beyond the width (even locally) of the NFM fibers used in this experiment. It is thus reasonable to predict that the retardation factor may stay constant or even become smaller for very long DNAs. Nevertheless, a clear relationship exists between the characteristic translocation times and DNA length.

Example 31: Size Profiling of Nucleic Acid Mixtures

Figure 19:
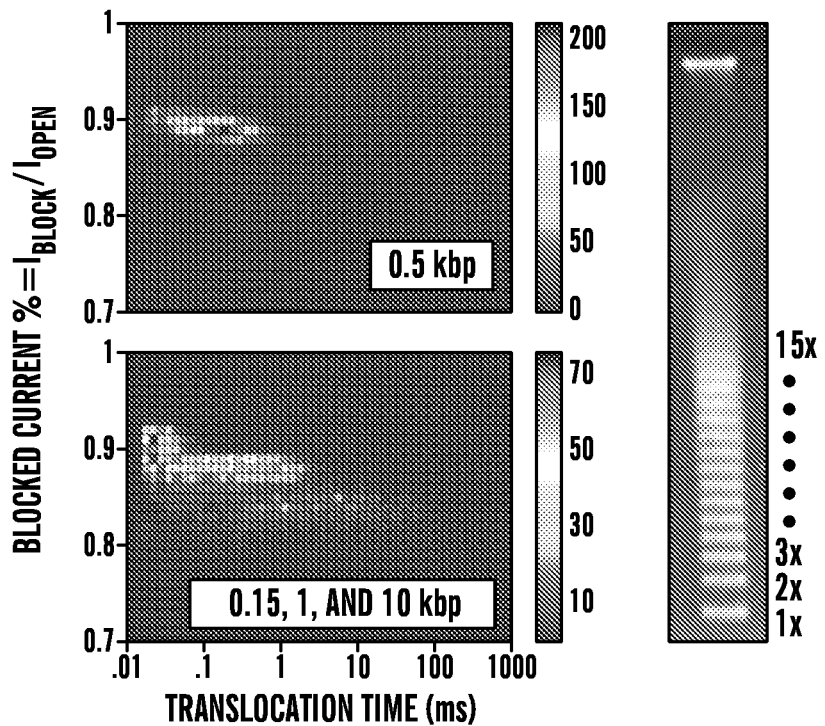
FIG. 19 depicts on the left, sample nanopore length profiles for short DNA. Distribution of current blockage and times for translocations of 500 bp DNA only (top) and a mixture of 150 bp, 1 kbp, and 10 kbp DNA (bottom). On the right, pulsed-field gel electrophoresis of a concatenated lambda ladder separating 48,000 base-pair DNA (1×) up to 720,000 base-pair DNA (15×).

Low concentrations (sub-nM) of restriction-digested DNA or RNA may be quickly sized and identified using a nanopore sensor. Each set of digested DNA or RNA fragments will produce a unique length profile, or "fingerprint", of nanopore translocation times and blockage levels, visualized as a scatter plot or two-dimensional population density map (FIG. 19). This technique may be used, for example, to rapidly identify pathogens. The hydrophobic mesh previously described increases translocation times of DNA fragments, thereby improving the temporal resolution of this technique.

Example 32: Detection of Avidin at Low Concentrations

Figure 20:
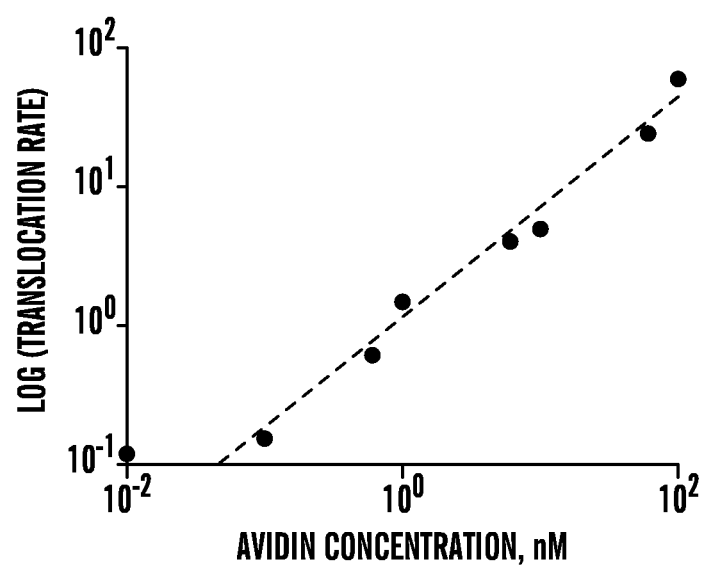
FIG. 20 depicts a calibration of avidin translocation rates as a function of sample concentration through a 5 nm solid-state nanopore. Avidin is detectable down to ~10 pM.
Figure 21:
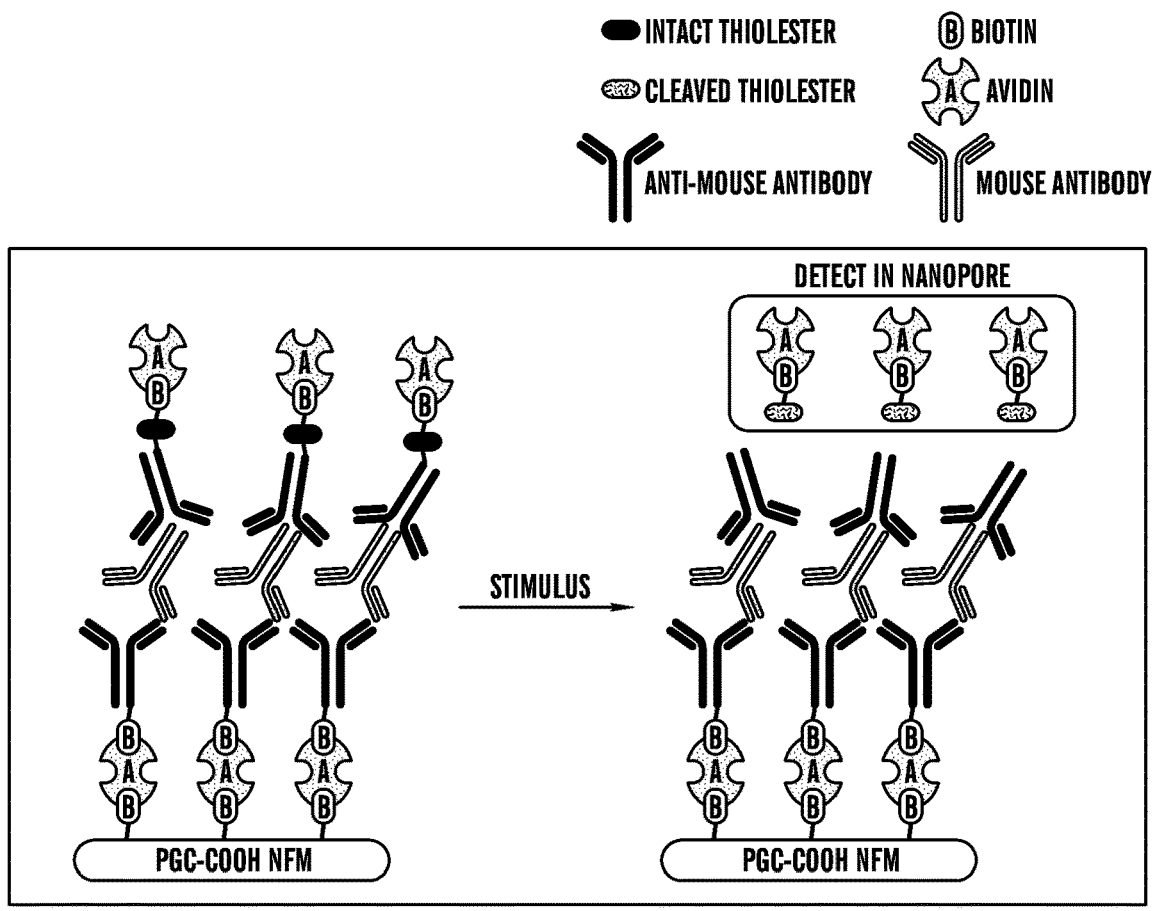
FIG. 21 depicts a schematic diagram of the proof of concept capture and release nanopore-nanofiber mesh protein detection assay. A biotinylated nanofiber mesh is coated in avidin which is then linked to a biotinylated capture anti-mouse antibody. The target antibody then binds followed by the second anti-mouse antibody which is functionalized to release avidin into solution upon the addition of a stimulus. This released avidin is detected in a nanopore only if the target molecule is present and it is released in an amount directly related to the amount of captured analyte.
Figure 22:
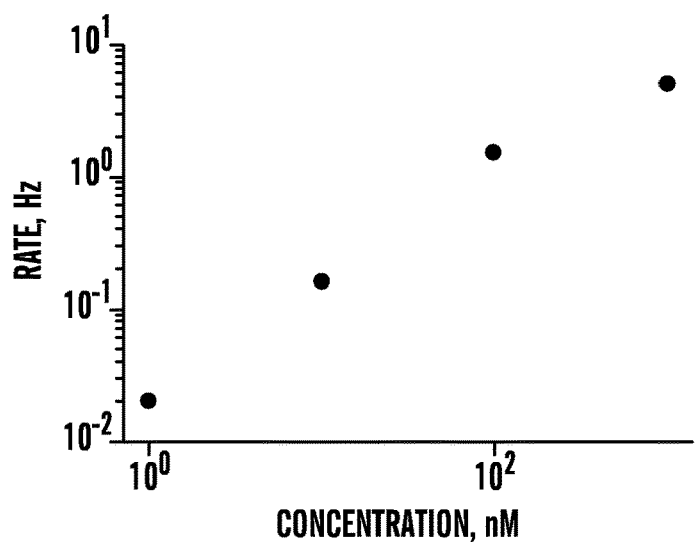
FIG. 22 depicts a calibration curve for detecting 20 kg/mol poly(acrylic acid) in a 5 nm solid-state nanopore. The event rate increases with increasing concentration of the polyelectrolyte.
Figure 23A:
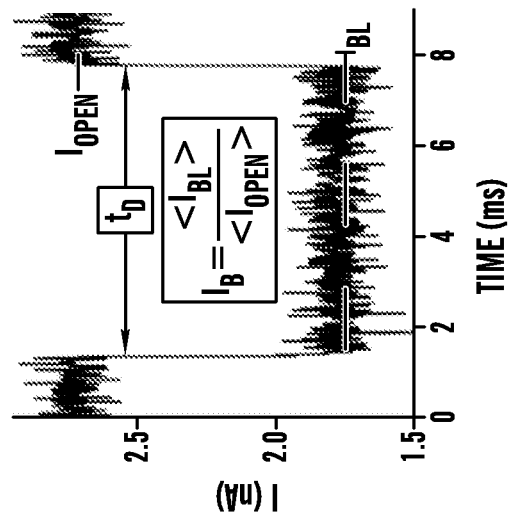
FIG. 23A depicts a schematic of voltage-clamp acquisition for a solid-state nanopore chip (not to scale). Measurements typically performed in 1M KCl with 300 mV applied.
Figure 23B:
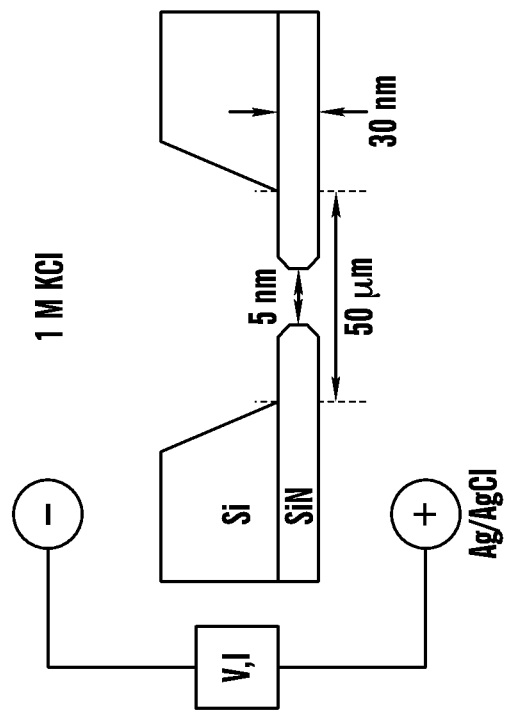
FIG. 23B depicts a sample current trace for 1200 bp ds DNA passing through a nanopore showing current blockage IBL and dwell time tD.
Figure 23C:
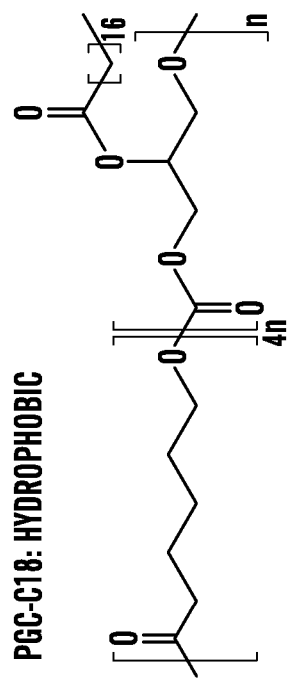
FIG. 23C depicts a synthetic scheme of PGC functionalized with a hydrophobic side chain.
Figure 23C:
Figure 23C:
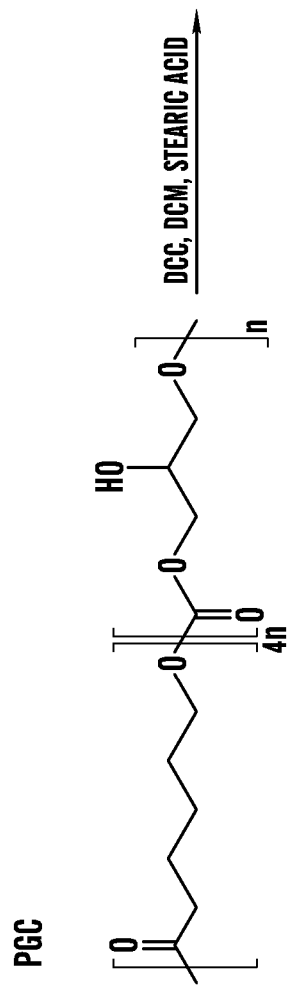
Figure 23D:
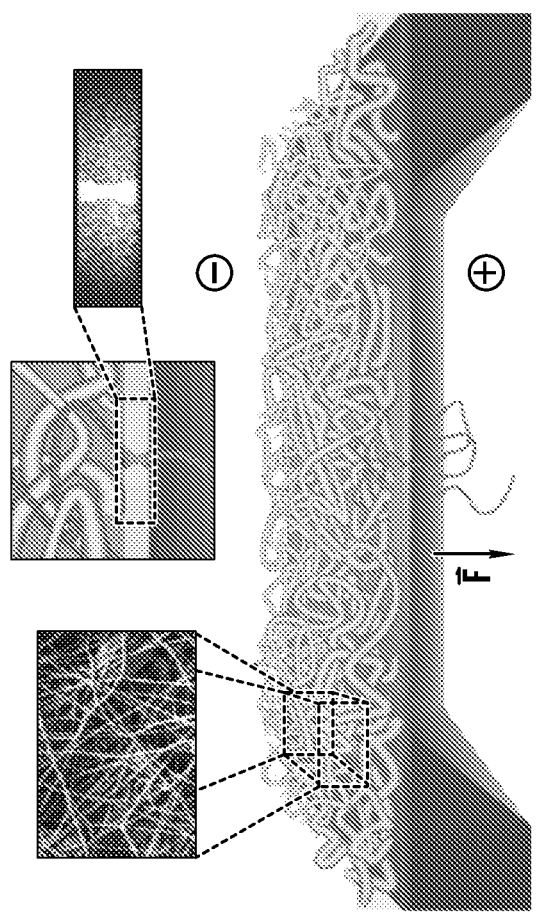
FIG. 23D is similar to FIG. 7 and depicts a cartoon representation of the nanopore-nanofiber mesh (NP-NFM) device. A nanopore sensor (gold) is coated with an electrospun polymeric nanofiber mesh (NFM). A DNA molecule threading through the pore is shown. Insets show electron micrographs of the NFM (left) and nanopore (right).
Figure 24A:
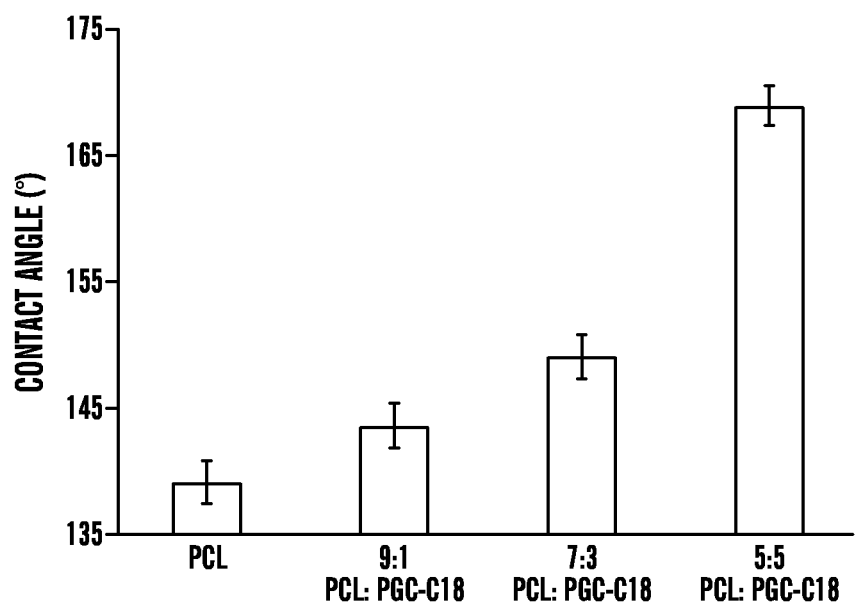
FIG. 24A demonstrates effect of PCL:PGC-C18 copolymer ratio on nanofiber mesh hydrophobicity for ~300 nm fiber diameters (n=3) measured via contact angle.
Figure 24B:
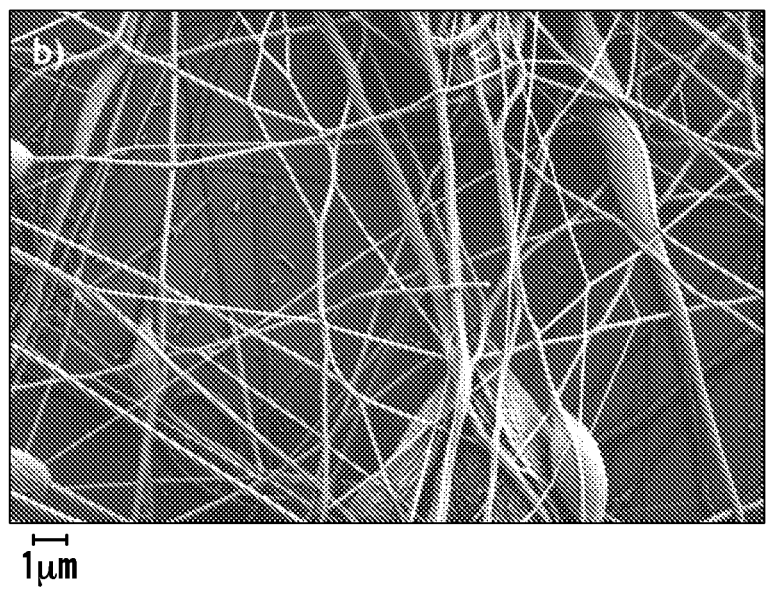
FIG. 24B shows Scanning Electron Micrographs of a continuous nonwoven electrospun polymeric mesh at low and high magnification, respectively. Both the mesh density and the fiber diameter may be controlled independently to vary mesh properties. Current versus voltage curves measured for an uncoated nanopore and two NP-NFM devices (PCL only; 70:30 PCL:PGC). The identical conductance for all conditions indicates that the NFM coating does not alter the electrical properties of the nanopore.
Figure 25A:
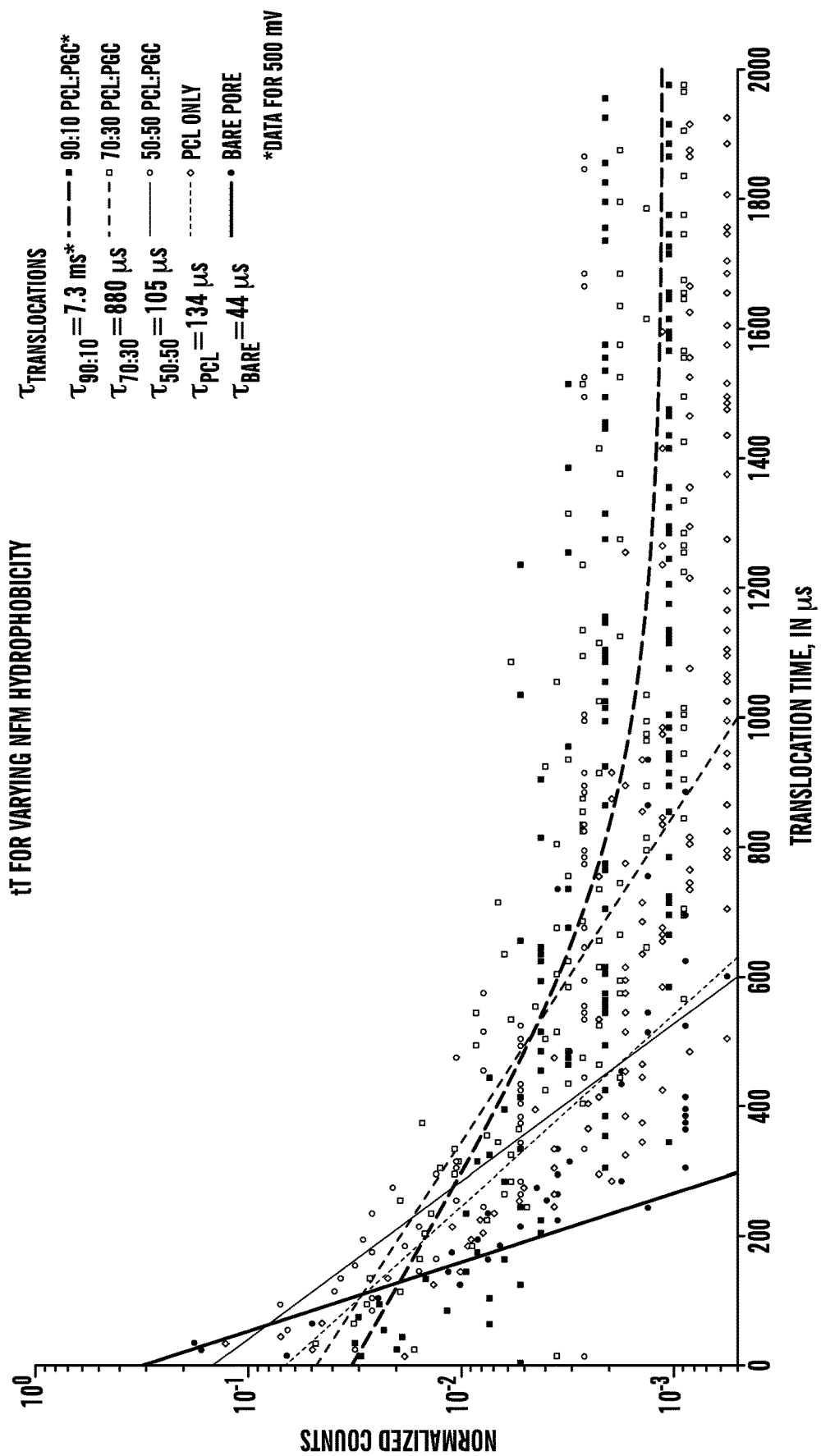
FIG. 25A shows a time of translocation PDF for NP-NFM devices with varying hydrophobicities. Plotted on semilog scale for resolution of decay timescales.
Figure 25B:
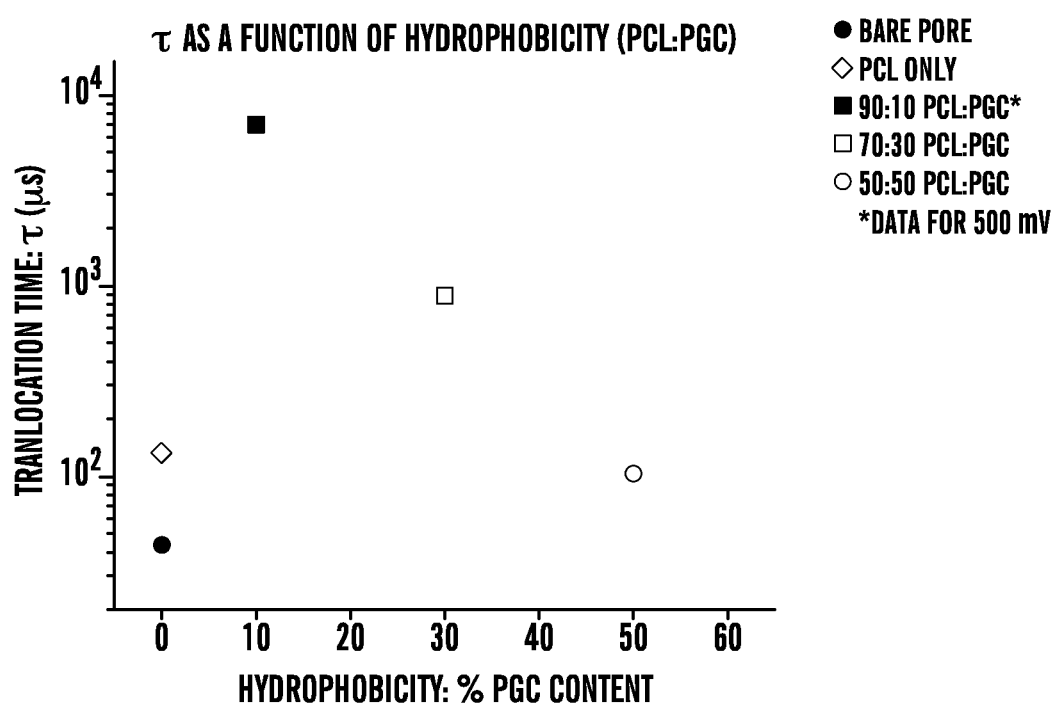
FIG. 25B shows decay timescales for same NP-NFM devices plotted against mesh hydrophobicity. 1000 bp DNA, V=300 mV, dnanopore=4 nm, T=21.0° C. for all data except as noted. 1000+ events are collected for each data set. The 90:10 blend is shown in a 4 nm pore at 500 mV because 300 mV is insufficient to induce translocations at that coating copolymer ratio.
Figure 26:
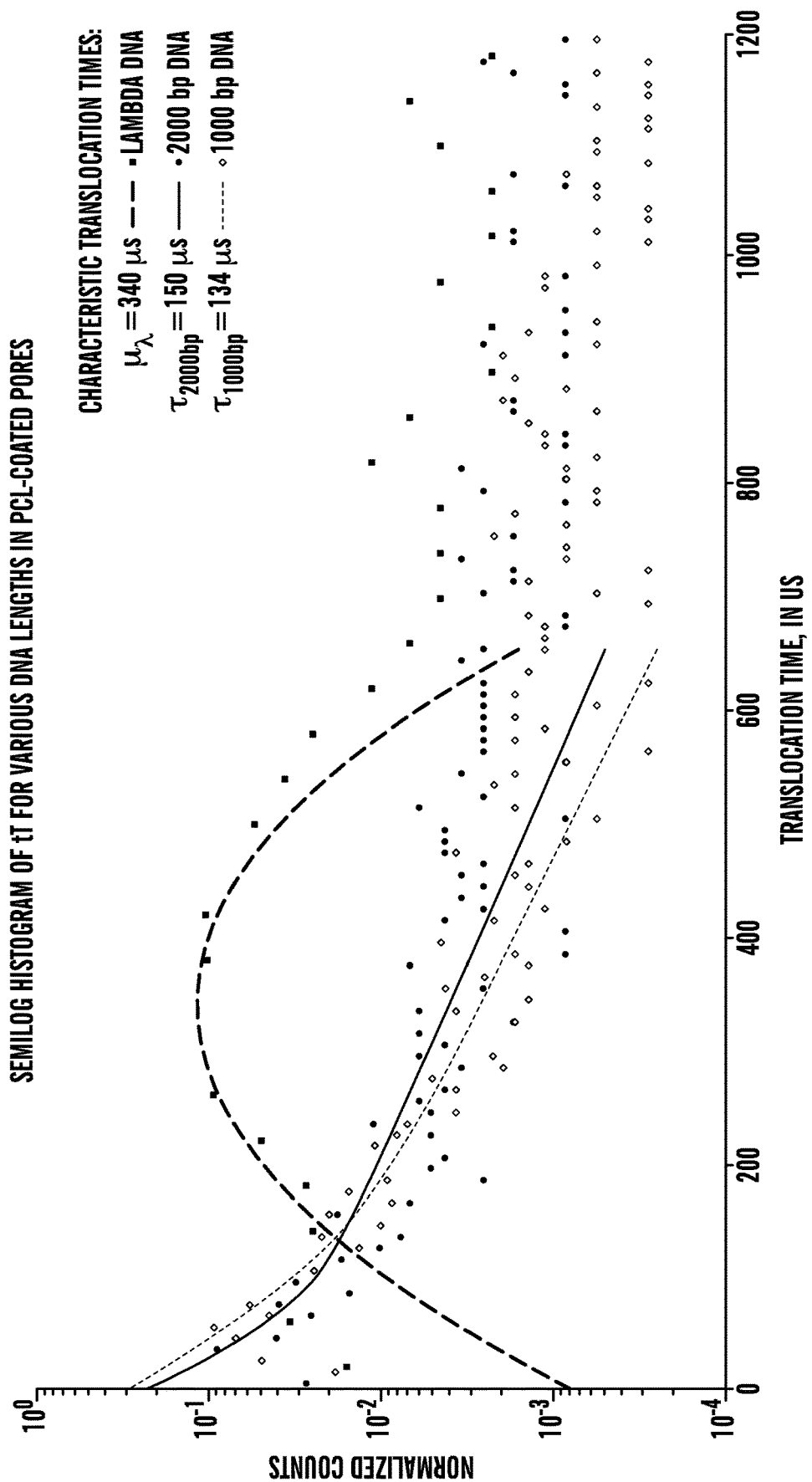
FIG. 26 shows translocation time PDF for varying lengths of DNA in a PCL-coated NP-NFM sensor. For very long DNA, the distribution looks more Gaussian than for shorter DNA, and therefore can be modeled by the actual mean rather than a characteristic decay rate for the distribution tail. Characteristic translocation times of various DNA lengths through a PCL-coated pore as compared to timescales through a bare nanopore.
Figure 27:
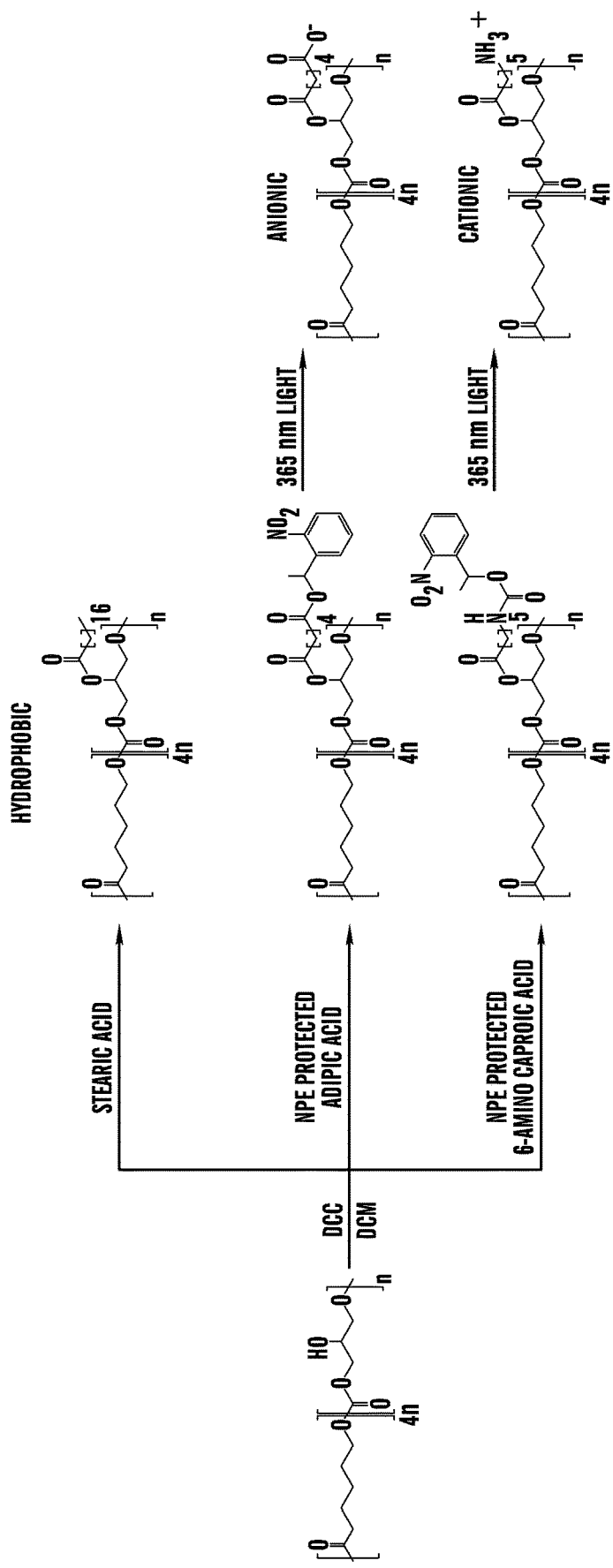
FIG. 27 shows current versus voltage curves measured for an uncoated (blue) and two NP-NFM devices (PCL only, green; 70:30 PCL:PGC, red). The identical conductance for all conditions indicates that the NFM coating does not alter the electrical properties of the nanopore
Figure 27:
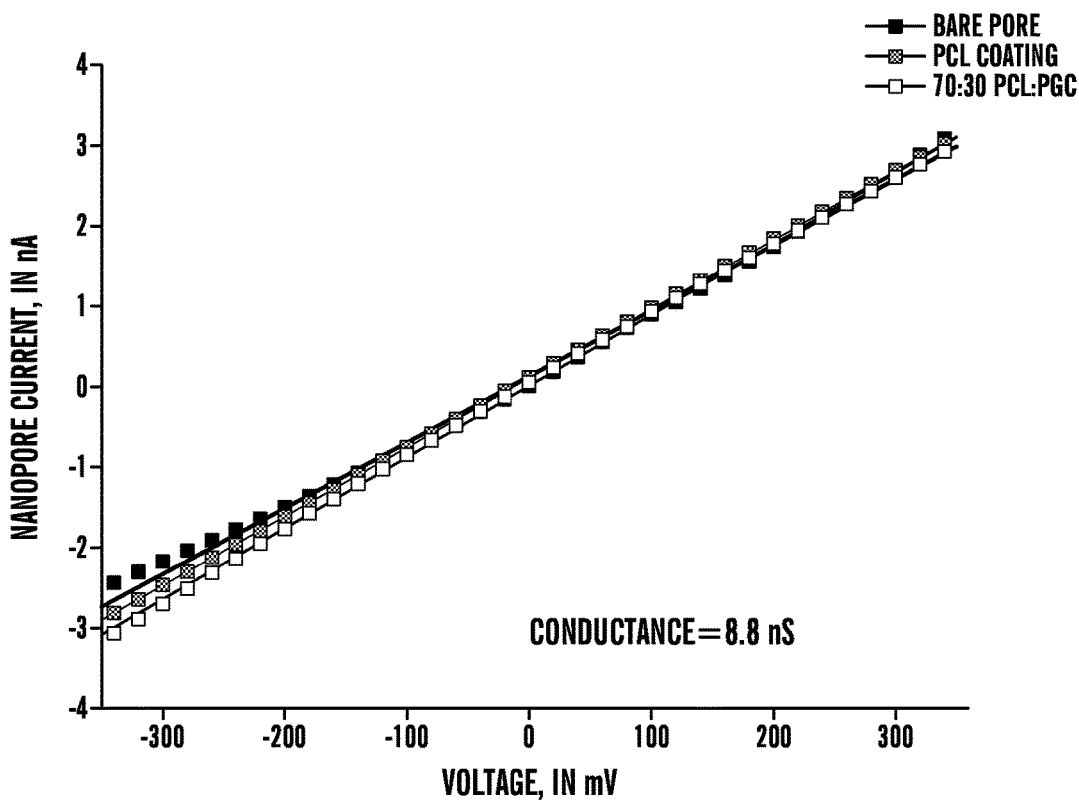
Figure 27:
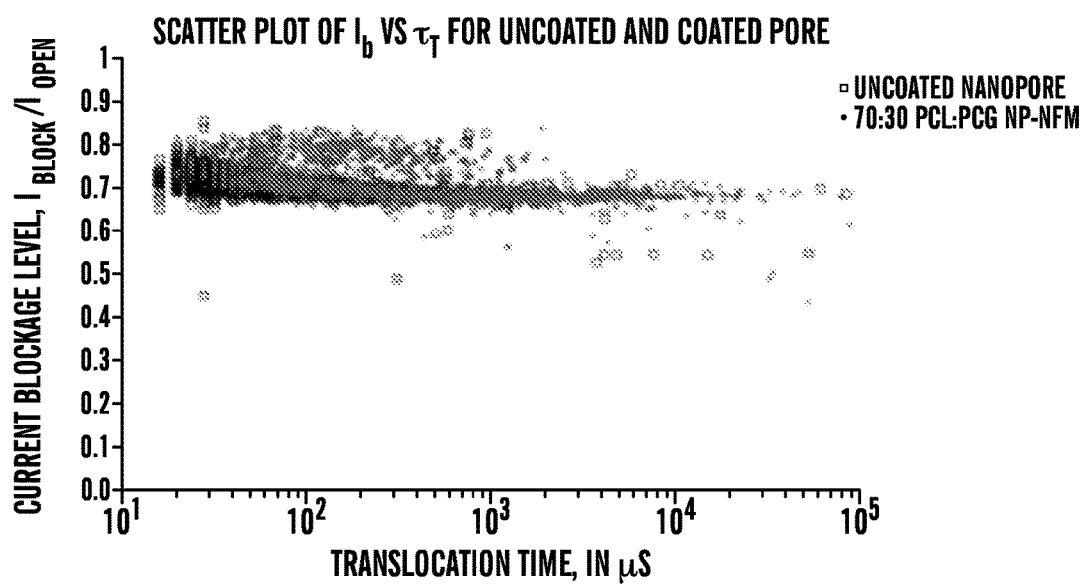
Figure 27:
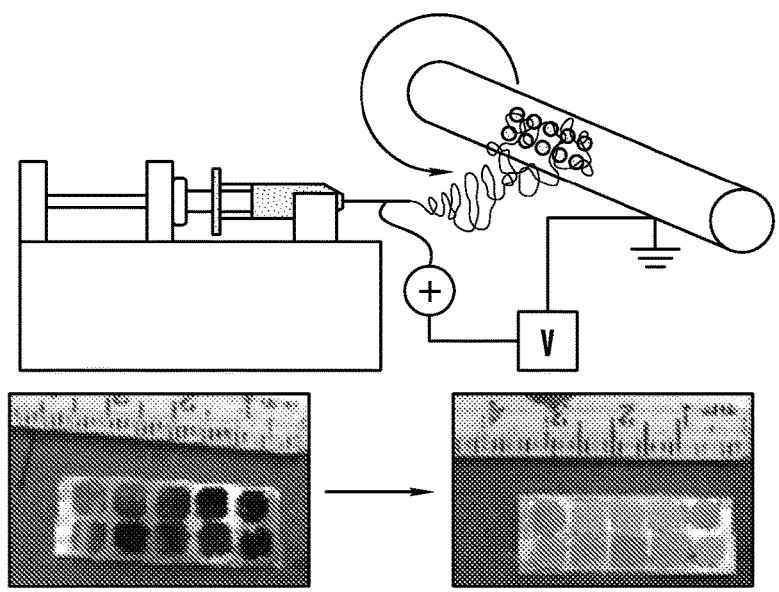

Avidin is the release unit for the protein detection assay which resembles an ELISE assay (NP-ELISA assay). The presence of the analyte is detected by translocations of avidin through the nanopore. The quantity of analyte is directly related to the quantity (concentration) of released avidin, which is detectable from ~10 pM over ~6 orders of magnitude. FIG. 20 depicts a typical calibration curve for avidin in a solid state nanopore. The line is to guide the eye.

Example 33: Target Protein Detection Via Capture of Target Protein onto a Nanofiber Mesh and Controlled Release of a Reporter Molecule for Nanopore Detection Using the Avidin functionalized PGC meshes from example 12, a capture and release nanopore-nanofiber mesh (NP-NFM) was created utilizing the methodology of a traditional ELISA sandwich assay with a novel reporting method. This platform technology can easily be adapted to detect any analyte with commercially available antibodies (NP-ELISA). A model system using a generic mouse antibody as the target analyte was developed as a proof of concept system. The avidin coated fibers capture biotinylated anti-mouse antibodies. The fibers are washed to remove unbound materials and then exposed to excess free-biotin to bind all remaining biotin binding sites on the fibers. The mesh is then washed followed by the addition of the analyte at varying concentrations. The mesh is washed followed by the addition of a second anti-mouse antibody which is tethered to a biotin through the stimuli responsive thiol-ester described in example 15. The mesh is washed and then exposed to excess Avidin which will bind any free biotin tethered to the second anti-mouse antibody. The mesh is washed and then exposed to the stimulus which in this case is 1000 equivalents of cysteine methyl ester which undergoes a thiol-thiolester exchange separating the antibody from the avidin. The free avidin in solution is then free to be detected on the nanopore. See example 32 for avidin detection in a nanopore.

Example 34: Detection of Scale Inhibitors at Low Concentrations

Polyacrylic acid is a common scale inhibitor. Here we show that a nanopore sensing device can detect translocations of polyacrylic acid (20,000 Da MW) down to single nanomolar concentrations, more than an order of magnitude more sensitive than current sensing techniques for scale inhibitors. This technique could be used, for example, to quantify the amount of scale inhibitor present in an oil well and determine the proper timing for performing squeeze treatments.

REFERENCES (1) Wanunu, M.; Sutin, J.; McNally, B.; Chow, A.; Meller, A. DNA translocation governed by interactions with solid state nanopores *Biophys J* 2008, 95, 4716-4725.
(2) Li, J.; Stein, D.; McMullan, C.; Branton, D.; Aziz, M. J.; Golovchenko, J. A. Ion-beam sculpting at nanometre length scales *Nature* 2001, 412, 166-9.
(3) Storm, A. J.; Chen, J. H.; Ling, X. S.; Zandbergen, H. W.; Dekker, C. Fabrication of solid-state nanopores with single-nanometre precision *Nat Mater* 2003, 2, 537-40.
(4) Heng, Z. B.; Ho, C.; Kim, T.; Timp, R.; Aksimentiev, A.; Grinkova, Y. V.; Sligar, S.; Schulten, K.; Timp, G. Sizing DNA using a nanometer-diameter pore *Biophys J* 2004, 87, 2905-11.
(5) Wu, S.; Park, S. R.; Ling, X. S. Lithography-free formation of nanopores in plastic membranes using laser heating *Nano Lett* 2006, 6, 2571-6.

(6) White, R. J.; Ervin, E. N.; Yang, T.; Chen, X.; Daniel, S.; Cremer, P. S.; White, H. S. Single ion-channel recordings using glass nanopore membranes *J Am Chem Soc* 2007, 129, 11766-75.

(7) Kim, M. J.; Wanunu, M.; Bell, D. C.; Meller, A. Rapid fabrication of uniformly sized nanopores and nanopore arrays for parallel DNA analysis *Adv Mater* 2006, 18, 3149-3153.

(8) Schneider, G. F.; Kowalczyk, S. W.; Calado, V. E.; Pandraud, G.; Zandbergen, H. W.; Vandersypen, L. M.; Dekker, C. DNA translocation through graphene nanopores *Nano Lett* 2010, 10, 3163-7.

(9) Merchant, C. A.; Healy, K.; Wanunu, M.; Ray, V.; Peterman, N.; Bartel, J.; Fischbein, M. D.; Venta, K.; Luo, Z.; Johnson, A. T.; Drndic, M. DNA translocation through graphene nanopores *Nano Lett* 2010, 10, 2915-21.

(10) Heins, E. A.; Baker, L. A.; Siwy, Z. S.; Mota, M. O.; Martin, C. R. Effect of crown ether on ion currents through synthetic membranes containing a single conically shaped nanopore *J Phys Chem B* 2005, 109, 18400-7.

(11) Wanunu, M.; Meller, A. Chemically modified solid-state nanopores *Nano Lett* 2007, 7, 1580-1585.

(12) Cockroft, S. L.; Chu, J.; Amorin, M.; Ghadiri, M. R. A single-molecule nanopore device detects DNA polymerase activity with single-nucleotide resolution *J Am Chem Soc* 2008, 130, 818-20.

(13) Olasagasti, F.; Lieberman, K. R.; Benner, S.; Cherf, G. M.; Dahl, J. M.; Deamer, D. W.; Akeson, M. Replication of individual DNA molecules under electronic control using a protein nanopore *Nat Nanotechnol* 2010, 5, 798-806.

(14) Mussi, V.; Fanzio, P.; Repetto, L.; Firpo, G.; Scaruffi, P.; Stigliani, S.; Menotta, M.; Magnani, M.; Tonini, G. P.; Valbusa, U. Electrical characterization of DNA-functionalized solid state nanopores for bio-sensing *Journal of physics. Condensed matter: an Institute of Physics journal* 2010, 22, 454104.

(15) Mussi, V.; Fanzio, P.; Repetto, L.; Firpo, G.; Stigliani, S.; Tonini, G. P.; Valbusa, U. "DNA-Dressed NAnopore" for complementary sequence detection *Biosensors and Bioelectronics* 2011, 29, 125-131.

(16) Howorka, S.; Cheley, S.; Bayley, H. Sequence-specific detection of individual DNA strands using engineered nanopores *Nature biotechnology* 2001, 19, 636-9.

(17) Iqbal, S. M.; Akin, D.; Bashir, R. Solid-state nanopore channels with DNA selectivity *Nature nanotechnology* 2007, 2, 243-8.

(18) Bouchet, A.; Descamps, E.; Mailley, P.; Livache, T.; Haguet, V.; Chatelain, F., METHOD FOR FUNCTIONALISING THE WALL OF A PORE. EP Patent 2,250,122: 2010.

(19) Gyarfas, B.; Abu-Shumays, R.; Wang, H.; Dunbar, W. B. Measuring single-molecule DNA hybridization by active control of DNA in a nanopore *Biophysical journal* 2011, 100, 1509-16.

(20) Moretti, M.; Di Fabrizio, E.; Cabrini, S.; Musetti, R.; De Angelis, F.; Firrao, G. An ON/OFF biosensor based on blockade of ionic current passing through a solid-state nanopore *Biosensors and Bioelectronics* 2008, 24, 141-147.

(21) WANG, Y.; TIAN, K., NANOPORE-FACILITATED SINGLE MOLECULE DETECTION OF NUCLEIC ACIDS. WO Patent 2,012,009,578: 2012.

(22) Merriman, B.; Mola, P., METHOD OF ANALYSIS OF GENETIC MARKERS. US Patent 20,120,214,256: 2012.

(23) Wolinsky, J. B.; Ray, W. I.; Colson, Y. L.; Grinstaff, M. W. Poly (carbonate ester) s based on units of 6-hydroxyhexanoic acid and glycerol *Macromolecules* 2007, 40, 7065-7068.

(24) Yohe, S. T.; Colson, Y. L.; Grinstaff, M. W. Superhydrophobic materials for tunable drug release: using displacement of air to control delivery rates *Journal of the American Chemical Society* 2012, 134, 2016-2019.

(25) Pham, Q. P.; Sharma, U.; Mikos, A. G. Electrospun poly (ε-caprolactone) microfiber and multilayer nanofiber/microfiber scaffolds: characterization of scaffolds and measurement of cellular infiltration *Biomacromolecules* 2006, 7, 2796-2805.

(26) Chen, C. S.; Mrksich, M.; Huang, S.; Whitesides, G. M.; Ingber, D. E. Geometric control of cell life and death *Science* 1997, 276, 1425-1428.

(27) Tan, J. L.; Liu, W.; Nelson, C. M.; Raghavan, S.; Chen, C. S. Simple approach to micropattern cells on common culture substrates by tuning substrate wettability *Tissue Eng.* 2004, 10, 865-872.

(28) Ishizaki, T.; Saito, N.; Takai, O. Correlation of cell adhesive behaviors on superhydrophobic, superhydrophilic, and micropatterned superhydrophobic/superhydrophilic surfaces to their surface chemistry *Langmuir* 2010, 26, 8147-8154.

(29) Ber, S.; Torun Köse, G.; Hasirci, V. Bone tissue engineering on patterned collagen films: an in vitro study *Biomaterials* 2005, 26, 1977-1986.

(30) Falconnet, D.; Csucs, G.; Michelle Grandin, H.; Textor, M. Surface engineering approaches to micropattern surfaces for cell-based assays *Biomaterials* 2006, 27, 3044-3063.

(31) Fernandes, T. G.; Diogo, M. M.; Clark, D. S.; Dordick, J. S.; Cabral, J. High-throughput cellular microarray platforms: applications in drug discovery, toxicology and stem cell research *Trends Biotechnol.* 2009, 27, 342-349.

(32) Kim, D. H.; Lee, H.; Lee, Y. K.; Nam, J. M.; Levchenko, A. Biomimetic nanopatterns as enabling tools for analysis and control of live cells *Adv. Mater.* 2010, 22, 4551-4566.

(33) Kachouie, N. N.; Du, Y.; Bae, H.; Khabiry, M.; Ahari, A. F.; Zamanian, B.; Fukuda, J.; Khademhosseini, A. Directed assembly of cell-laden hydrogels for engineering functional tissues *Organogenesis* 2010, 6, 234-244.

(34) Kim, M. J.; Wanunu, M.; Bell, D. C.; Meller, A. Rapid fabrication of uniformly sized nanopores and nanopore arrays for parallel DNA analysis *Adv. Mater.* 2006, 18, 3149-3153.

(35) Squires, A. H.; Hersey, J. S.; Grinstaff, M. W.; Meller, A. A nanopore-nanofiber mesh biosensor to control DNA translocation *Journal of the American Chemical Society* 2013.

(36) Wanunu, M.; Sutin, J.; McNally, B.; Chow, A.; Meller, A. DNA translocation governed by interactions with solid state nanopores *Biophys. J* 2008, 95, 4716-4725.

(37) Meller, A.; Nivon, L.; Brandin, E.; Golovchenko, J.; Branton, D. Rapid nanopore discrimination between single polynucleotide molecules *Proc. Natl. Acad. Sci.* 2000, 97, 1079-1084.

What is claimed is:

1. An article comprising: (i) a substrate having a first surface and a second surface; (ii) at least one nanopore extending through the substrate, thus forming a channel connecting from the first surface to the second surface of the substrate, wherein the nanopore has a first opening that opens to the first surface of the substrate and a second opening that opens to the second surface of the substrate;

and (iii) a 3D porous coating on at least one of the first or second surface of the substrate, wherein the porous coating comprises oligomer or polymer nanofibers, and wherein the nanopore has a diameter of about 2 nm to about 50 nm, and wherein the 3D porous coating covers at least one of the first opening or the second opening of said at least one nanopore, wherein the oligomer or polymer is a linear, comb, branched, or dendritic oligomer or polymer represented by one of the following formulas:

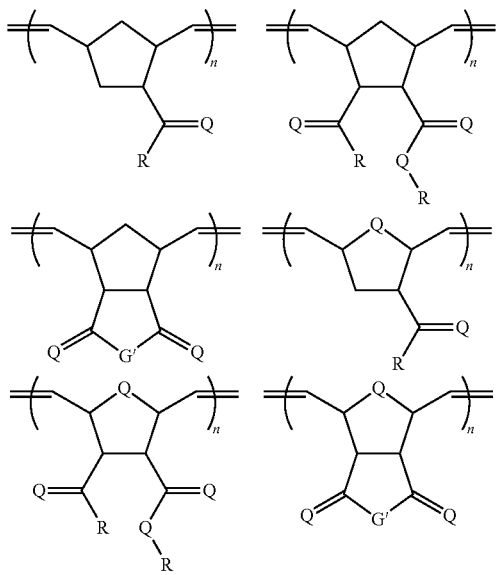

wherein:
  Q is independently selected from among O, S, Se, or NH;
  G' is each independently selected from among the following structures:

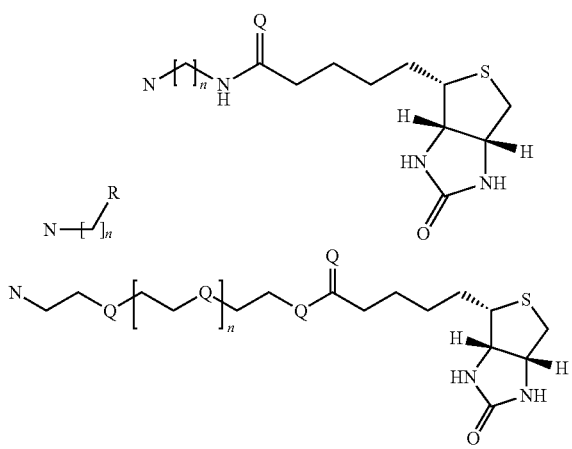

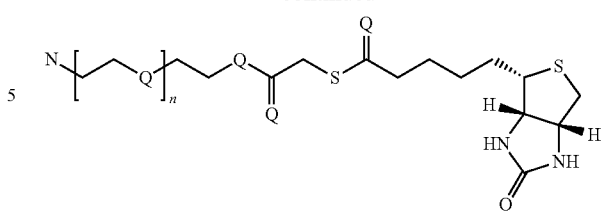

R is selected from among a hydrogen, straight or branched alkyl, cycloalkyl, aryl, olefin, silyl, alkylsilyl, arylsilyl, alkylaryl or arylalkyl chain of 1-50 carbons, wherein each alkyl, cycloalkyl, aryl, olefin, silyl, alkylsilyl, arylsilyl, alkylaryl, fluorocarbon, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; or R is selected from among poly(ethylene glycol), poly (ethylene oxide), poly(hydroxyacid)), a carbohydrate, a protein, a polypeptide, an amino acid, a nucleic acid, a nucleotide, a polynucleotide, any DNA or RNA segment, a lipid, a polysaccharide, an antibody, a pharmaceutical agent, or any epitope for a biological receptor; or R is selected from among a photocrosslinkable or ionically crosslinkable group;

n is independently selected from an integer of 1-1000;

each polymeric terminal group is selected from among amines, thiols, amides, phosphates, sulphates, hydroxides, metals, alkanes, alkenes and alkynes.

2. The article of claim 1, wherein the substrate is a membrane or a solid-state, polymer, or lipid film.

3. The article of claim 1, wherein the 3D porous coating further comprises a target binding moiety.

4. The article of claim 3, wherein the targeting moiety is covalently linked to the 3D porous coating.

5. The article of claim 1, wherein the 3D porous coating further comprises a denaturing agent.

6. The article of claim 1, wherein the oligomer or polymer further comprises a reactive functional group.

7. The article of claim 1, wherein the 3D porous coating comprises a hydrophobic, hydrophilic, cationic and/or anion group.

* * * * *